US012646604B1

(12) United States Patent
Lewis et al.

(10) Patent No.: US 12,646,604 B1
(45) Date of Patent: Jun. 2, 2026

(54) DETECTION OF THE SPEED OF AN OBJECT PASSING THROUGH A GOAL PLANE

(71) Applicant: TOCA Football, Inc., Costa Mesa, CA (US)

(72) Inventors: Edward J. Lewis, Thousand Oaks, CA (US); Wayne Morton Rapp, Irvine, CA (US); Steven Eannarino, Newport Beach, CA (US)

(73) Assignee: TOCA Football, Inc., Costa Mesa, CA (US)

( * ) Notice: Subject to any disclaimer, the term of this patent is extended or adjusted under 35 U.S.C. 154(b) by 527 days.

(21) Appl. No.: 18/191,755

(22) Filed: Mar. 28, 2023

Related U.S. Application Data

(63) Continuation of application No. 16/995,289, filed on Aug. 17, 2020, now Pat. No. 11,657,906, which is a
(Continued)

(51) Int. Cl.
 G16H 20/30 (2018.01)
 A63B 24/00 (2006.01)
 (Continued)

(52) U.S. Cl.
 CPC ......... G16H 20/30 (2018.01); A63B 24/0062 (2013.01); A63B 24/0075 (2013.01);
 (Continued)

(58) Field of Classification Search
 CPC G16H 20/30; A63B 24/0062; A63B 24/0075; A63B 47/002; A63B 69/002;
 (Continued)

(56) References Cited

U.S. PATENT DOCUMENTS 2,918,915 A 12/1959 Doeg
3,028,704 A 4/1962 Rumbaugh
(Continued)

FOREIGN PATENT DOCUMENTS

AU 2005248763 B2 6/2010
AU 2015204422 A1 8/2017
(Continued)

OTHER PUBLICATIONS

C. Spiteri, "Generating A Three-Dimensional Topography Of A Training Environment," filed Jul. 21, 2023, U.S. Appl. No. 18/224,987 including its prosecution history.
(Continued)

*Primary Examiner* — Allen Chan
(74) *Attorney, Agent, or Firm* — Rutan & Tucker, LLP; Kyle M. St. James

(57) ABSTRACT

A computerized method is disclosed that includes operations of detecting a through-beam between first and second sensors of a first sensor pair, the first sensor being located at a first goal post of a goal apparatus, the second sensor being located at a second goal post of the goal apparatus, wherein the first goal post and the second goal post form a goal plane, detecting an interrupt in the through-beam between the first and second sensors, and responsive to detecting the interrupt determining an object has passed through the goal plane, and determining a speed of the object as the objected passed through the goal plane. In some instances, the operations include determining a time duration of the interrupt. In some instances, the operations include correlating the time duration of the interrupt with a known size of the object.

17 Claims, 24 Drawing Sheets

Related U.S. Application Data continuation-in-part of application No. 15/374,984, filed on Dec. 9, 2016, now Pat. No. 10,118,078, which is a continuation of application No. 14/617,599, filed on Feb. 9, 2015, now Pat. No. 9,555,306, which is a continuation of application No. 13/287,749, filed on Nov. 2, 2011, now Pat. No. 9,010,309.

(51) Int. Cl.

| | |
|---|---|
| A63B 47/00 | (2006.01) |
| A63B 69/00 | (2006.01) |
| A63B 69/40 | (2006.01) |
| A63B 71/06 | (2006.01) |
| G06Q 50/00 | (2012.01) |
| G09B 5/02 | (2006.01) |
| G09B 19/00 | (2006.01) |
| A63B 22/00 | (2006.01) |
| A63B 63/00 | (2006.01) |
| A63B 71/00 | (2006.01) |
| A63B 102/02 | (2015.01) |
| A63B 102/06 | (2015.01) |
| A63B 102/14 | (2015.01) |
| A63B 102/18 | (2015.01) |
| A63B 102/20 | (2015.01) |

(52) U.S. Cl.
CPC .......... *A63B 47/002* (2013.01); *A63B 69/002* (2013.01); *A63B 69/40* (2013.01); *A63B 69/406* (2013.01); *A63B 71/0605* (2013.01); *A63B 71/0619* (2013.01); *A63B 71/0622* (2013.01); *G06Q 50/01* (2013.01); *G09B 5/02* (2013.01); *G09B 19/0038* (2013.01); *A63B 2022/0092* (2013.01); *A63B 24/0087* (2013.01); *A63B 63/004* (2013.01); *A63B 2069/402* (2013.01); *A63B 2071/0063* (2013.01); *A63B 2071/0072* (2013.01); *A63B 2071/0081* (2013.01); *A63B 2071/0625* (2013.01); *A63B 2071/063* (2013.01); *A63B 2071/0677* (2013.01); *A63B 2071/068* (2013.01); *A63B 2071/0683* (2013.01); *A63B 2071/0694* (2013.01); *A63B 2102/02* (2015.10); *A63B 2102/06* (2015.10); *A63B 2102/065* (2015.10); *A63B 2102/14* (2015.10); *A63B 2102/18* (2015.10); *A63B 2102/182* (2015.10); *A63B 2102/20* (2015.10); *A63B 2208/12* (2013.01); *A63B 2209/10* (2013.01); *A63B 2210/50* (2013.01); *A63B 2220/17* (2013.01); *A63B 2220/53* (2013.01); *A63B 2220/56* (2013.01); *A63B 2220/801* (2013.01); *A63B 2220/802* (2013.01); *A63B 2220/805* (2013.01); *A63B 2220/806* (2013.01); *A63B 2220/833* (2013.01); *A63B 2220/836* (2013.01); *A63B 2225/20* (2013.01); *A63B 2225/50* (2013.01); *A63B 2225/74* (2020.08); *A63B 2230/00* (2013.01); *A63B 2230/06* (2013.01); *A63B 2230/062* (2013.01); *A63B 2230/75* (2013.01); *A63B 2243/0025* (2013.01); *A63B 2243/0095* (2013.01); *G08C 2201/93* (2013.01)

(58) Field of Classification Search
CPC ... A63B 69/40; A63B 69/406; A63B 71/0605; A63B 71/0619; A63B 71/0622; G06Q 50/01; G09B 5/02; G09B 19/0038
USPC .......................................... 273/410; 473/446
See application file for complete search history.

(56) References Cited

U.S. PATENT DOCUMENTS

| | | | |
|---|---|---|---|
| 3,272,194 | A | 9/1966 | Egbert |
| 3,306,613 | A | 2/1967 | Mainers |
| 3,459,168 | A | 8/1969 | Bruce |
| 3,470,859 | A | 10/1969 | Ponza |
| 3,570,466 | A | 3/1971 | White et al. |
| 3,659,576 | A | 5/1972 | Eade et al. |
| 3,677,544 | A | 7/1972 | Meyers et al. |
| 3,777,732 | A | 12/1973 | Holloway et al. |
| 3,779,227 | A | 12/1973 | Scott |
| 3,785,358 | A | 1/1974 | D'Angelo et al. |
| 3,794,011 | A | 2/1974 | Newgarden, Jr. |
| 3,815,567 | A | 6/1974 | Serra |
| 3,844,267 | A | 10/1974 | Mohr |
| 3,855,988 | A | 12/1974 | Sweeton |
| 3,856,302 | A | 12/1974 | Karkoska |
| 3,892,217 | A | 7/1975 | Raty |
| 3,913,552 | A | 10/1975 | Yarur et al. |
| 3,930,486 | A | 1/1976 | Kahelin |
| 3,990,426 | A | 11/1976 | Stokes |
| 4,025,071 | A | 5/1977 | Hodges |
| 4,029,315 | A | 6/1977 | Bon |
| 4,046,131 | A | 9/1977 | Clark et al. |
| 4,070,018 | A | 1/1978 | Hodges |
| 4,077,386 | A | 3/1978 | Berliner |
| 4,086,903 | A | 5/1978 | Scott |
| 4,094,294 | A | 6/1978 | Speer |
| 4,209,003 | A | 6/1980 | Sainsbury |
| 4,209,004 | A | 6/1980 | Kennedy |
| 4,254,952 | A | 3/1981 | Playter, Jr. |
| 4,262,648 | A | 4/1981 | Wegener et al. |
| 4,280,697 | A | 7/1981 | Yuasa |
| 4,282,848 | A | 8/1981 | Kulesza et al. |
| 4,286,786 | A | 9/1981 | Papadopoulos |
| 4,299,383 | A | 11/1981 | Yuasa |
| 4,323,047 | A | 4/1982 | McIntosh et al. |
| 4,352,348 | A | 10/1982 | Griffith |
| 4,409,953 | A | 10/1983 | Kennedy et al. |
| 4,423,717 | A | 1/1984 | Kahelin |
| 4,442,823 | A | 4/1984 | Floyd et al. |
| 4,524,749 | A | 6/1985 | Giovagnoli |
| 4,531,504 | A | 7/1985 | Gilreath |
| 4,535,992 | A | 8/1985 | Slagle |
| 4,559,918 | A | 12/1985 | Ballerin et al. |
| 4,563,999 | A | 1/1986 | Miehlich |
| 4,596,230 | A | 6/1986 | Griffith |
| 4,632,088 | A | 12/1986 | Bruce |
| 4,646,709 | A | 3/1987 | Kholin |
| 4,655,190 | A | 4/1987 | Harris |
| 4,669,444 | A | 6/1987 | Whitfield et al. |
| 4,714,248 | A | 12/1987 | Koss |
| 4,723,532 | A | 2/1988 | Osojnak |
| 4,765,618 | A | 8/1988 | Daley |
| 4,772,017 | A | 9/1988 | Eriksen |
| 4,814,986 | A | 3/1989 | Spielman |
| 4,823,763 | A | 4/1989 | Ponza |
| 4,834,060 | A | 5/1989 | Greene |
| 4,875,459 | A | 10/1989 | Van Elderen et al. |
| 4,896,646 | A | 1/1990 | Kahelin et al. |
| 4,907,802 | A | 3/1990 | Gatin |
| 4,919,428 | A | 4/1990 | Perkins |
| 4,922,885 | A | 5/1990 | Iwabuchi et al. |
| 4,948,147 | A | 8/1990 | Pallanca |
| 5,012,790 | A | 5/1991 | Bates |
| 5,044,350 | A | 9/1991 | Iwabuchi et al. |
| 5,059,944 | A | 10/1991 | Carmona |
| 5,097,985 | A | 3/1992 | Jones |
| 5,107,820 | A | 4/1992 | Salansky |
| 5,121,735 | A | 6/1992 | Hancock |
| 5,125,653 | A | 6/1992 | Kovacs et al. |
| 5,174,565 | A | 12/1992 | Komori |
| 5,181,501 | A | 1/1993 | Lien |
| 5,181,725 | A | 1/1993 | Leras et al. |
| 5,188,367 | A | 2/1993 | Gipe et al. |
| 5,344,137 | A | 9/1994 | Komori |
| 5,347,975 | A | 9/1994 | Salansky |

(56)                References Cited

U.S. PATENT DOCUMENTS

| 5,359,986 | A |   | 11/1994 | Magrath, III et al. |
| 5,396,876 | A |   | 3/1995 | Liscio et al. |
| 5,438,518 | A |   | 8/1995 | Bianco et al. |
| 5,447,314 | A |   | 9/1995 | Yamazaki et al. |
| 5,464,208 | A |   | 11/1995 | Pierce |
| 5,465,978 | A |   | 11/1995 | Magnone et al. |
| 5,489,099 | A |   | 2/1996 | Rankin et al. |
| 5,490,493 | A |   | 2/1996 | Salansky |
| 5,496,025 | A |   | 3/1996 | Phillips et al. |
| 5,498,000 | A |   | 3/1996 | Cuneo |
| 5,509,650 | A |   | 4/1996 | MacDonald |
| 5,607,151 | A |   | 3/1997 | Daley |
| 5,615,880 | A |   | 4/1997 | Booth et al. |
| 5,649,523 | A |   | 7/1997 | Scott |
| 5,697,791 | A |   | 12/1997 | Nashner et al. |
| 5,707,063 | A |   | 1/1998 | Tzeng et al. |
| 5,722,384 | A |   | 3/1998 | Cox |
| 5,748,073 | A |   | 5/1998 | Crawford |
| 5,768,151 | A |   | 6/1998 | Lowy et al. |
| 5,816,947 | A |   | 10/1998 | Kavitch |
| 5,820,496 | A | * | 10/1998 | Bergeron ............... A63B 63/00 |
|           |   |   |         | 356/28 |
| 5,860,873 | A |   | 1/1999 | Karasavas |
| 5,865,161 | A |   | 2/1999 | Bruce |
| 5,873,797 | A |   | 2/1999 | Garn |
| 5,882,204 | A |   | 3/1999 | Iannazo et al. |
| 5,897,445 | A |   | 4/1999 | Sanders |
| 5,911,214 | A |   | 6/1999 | Andrews |
| 5,938,204 | A |   | 8/1999 | Tzeng et al. |
| 5,938,545 | A |   | 8/1999 | Cooper et al. |
| 5,951,015 | A |   | 9/1999 | Smith et al. |
| 5,979,426 | A |   | 11/1999 | Troklus et al. |
| 6,026,798 | A |   | 2/2000 | Sanders et al. |
| 6,073,489 | A |   | 6/2000 | French et al. |
| 6,098,458 | A |   | 8/2000 | French et al. |
| 6,148,271 | A |   | 11/2000 | Marinelli |
| 6,152,126 | A |   | 11/2000 | Smith et al. |
| 6,179,720 | B1 |   | 1/2001 | Rankin et al. |
| 6,186,132 | B1 |   | 2/2001 | Ko |
| 6,190,271 | B1 |   | 2/2001 | Rappaport et al. |
| 6,224,503 | B1 |   | 5/2001 | Joseph |
| 6,237,583 | B1 |   | 5/2001 | Ripley et al. |
| 6,263,279 | B1 |   | 7/2001 | Bianco et al. |
| 6,308,565 | B1 |   | 10/2001 | French et al. |
| 6,389,368 | B1 |   | 5/2002 | Hampton |
| 6,401,704 | B1 |   | 6/2002 | Caldwell |
| 6,402,640 | B1 |   | 6/2002 | Stuart |
| 6,427,675 | B1 |   | 8/2002 | Caldwell et al. |
| 6,443,859 | B1 |   | 9/2002 | Markin |
| 6,470,873 | B2 |   | 10/2002 | Battersby et al. |
| 6,488,020 | B1 |   | 12/2002 | Rosas-Magallan |
| 6,508,243 | B1 |   | 1/2003 | Long |
| 6,513,512 | B2 |   | 2/2003 | Battersby et al. |
| 6,533,675 | B2 |   | 3/2003 | Funk |
| 6,539,931 | B2 |   | 4/2003 | Trajkovic et al. |
| 6,546,924 | B2 |   | 4/2003 | Battersby et al. |
| 6,551,205 | B1 |   | 4/2003 | Koelzer, Jr. et al. |
| 6,565,448 | B2 |   | 5/2003 | Cameron et al. |
| 6,582,330 | B1 |   | 6/2003 | Rehkemper et al. |
| 6,637,422 | B2 |   | 10/2003 | Wojtkiewicz et al. |
| 6,671,390 | B1 |   | 12/2003 | Barbour et al. |
| 6,707,487 | B1 |   | 3/2004 | Aman et al. |
| 6,757,572 | B1 |   | 6/2004 | Forest |
| 6,774,349 | B2 |   | 8/2004 | Vock et al. |
| 6,816,185 | B2 |   | 11/2004 | Harmath |
| 6,856,934 | B2 |   | 2/2005 | Vock et al. |
| 6,857,424 | B1 |   | 2/2005 | Payne |
| 6,877,501 | B2 |   | 4/2005 | Wojtkiewicz et al. |
| 6,880,542 | B1 |   | 4/2005 | Johndreau et al. |
| 6,918,845 | B2 |   | 7/2005 | Kudla |
| 7,011,084 | B2 |   | 3/2006 | Richard |
| 7,032,585 | B2 |   | 4/2006 | Johndreau et al. |
| 7,040,309 | B2 |   | 5/2006 | Johndreau et al. |
| 7,040,998 | B2 |   | 5/2006 | Jolliffe et al. |
| 7,056,237 | B2 |   | 6/2006 | Slavey et al. |

| 7,066,845 | B2 |   | 6/2006 | Joseph |
| 7,072,789 | B2 |   | 7/2006 | Vock et al. |
| 7,082,938 | B2 |   | 8/2006 | Wilmot |
| 7,092,846 | B2 |   | 8/2006 | Vock et al. |
| 7,100,594 | B2 |   | 9/2006 | Boehner |
| 7,111,620 | B2 |   | 9/2006 | Johndreau et al. |
| 7,162,392 | B2 |   | 1/2007 | Vock et al. |
| 7,192,387 | B2 |   | 3/2007 | Mendel |
| 7,231,913 | B2 |   | 6/2007 | Wilson |
| 7,237,546 | B2 |   | 7/2007 | Nozato |
| 7,258,633 | B2 |   | 8/2007 | Joseph et al. |
| 7,278,934 | B2 |   | 10/2007 | McBride et al. |
| 7,285,061 | B2 |   | 10/2007 | Wagner |
| 7,290,540 | B2 |   | 11/2007 | Lu |
| 7,335,116 | B2 |   | 2/2008 | Petrov |
| 7,445,003 | B2 |   | 11/2008 | Smith |
| 7,510,493 | B2 |   | 3/2009 | Wagner |
| 7,527,568 | B2 |   | 5/2009 | Joseph |
| 7,549,415 | B2 |   | 6/2009 | Karellas |
| 7,553,244 | B2 |   | 6/2009 | York |
| 7,610,909 | B2 |   | 11/2009 | Greene, Jr. |
| 7,625,314 | B2 |   | 12/2009 | Ungari et al. |
| 7,650,256 | B2 | * | 1/2010 | Petrov ...................... G01S 5/16 |
|           |    |   |        | 702/149 |
| 7,661,679 | B2 |   | 2/2010 | Mah et al. |
| 7,691,012 | B2 |   | 4/2010 | Cucjen et al. |
| 7,708,003 | B1 |   | 5/2010 | Gavieres |
| 7,766,770 | B2 |   | 8/2010 | Cucjen et al. |
| 7,795,861 | B2 |   | 9/2010 | Englert et al. |
| 7,806,788 | B1 |   | 10/2010 | Neuman |
| 7,813,821 | B1 |   | 10/2010 | Howell |
| 7,815,525 | B2 |   | 10/2010 | Small |
| 7,850,514 | B2 |   | 12/2010 | Weber |
| 7,850,536 | B1 |   | 12/2010 | Fitzgerald |
| 7,861,699 | B2 |   | 1/2011 | Gowan et al. |
| 7,867,113 | B2 |   | 1/2011 | Petersen |
| 7,882,831 | B2 |   | 2/2011 | Alger |
| 7,887,329 | B2 |   | 2/2011 | Greenshpan et al. |
| 7,891,666 | B2 |   | 2/2011 | Kuenzler et al. |
| 7,920,052 | B2 |   | 4/2011 | Costabile |
| 7,951,045 | B1 |   | 5/2011 | Brader |
| 8,070,654 | B2 |   | 12/2011 | Chapa, Jr. et al. |
| 8,078,478 | B2 |   | 12/2011 | Fleming et al. |
| 8,086,421 | B2 |   | 12/2011 | Case, Jr. et al. |
| 8,109,845 | B2 |   | 2/2012 | Duty |
| 8,109,858 | B2 |   | 2/2012 | Redmann |
| 8,128,410 | B2 |   | 3/2012 | Prstojevich |
| 8,152,695 | B2 |   | 4/2012 | Riley et al. |
| 8,172,722 | B2 |   | 5/2012 | Molyneux et al. |
| 8,206,246 | B2 |   | 6/2012 | Joseph et al. |
| 8,210,959 | B2 |   | 7/2012 | Balardeta et al. |
| 8,231,506 | B2 |   | 7/2012 | Molyneux et al. |
| 8,287,404 | B2 |   | 10/2012 | Cucjen et al. |
| 8,342,162 | B2 |   | 1/2013 | Alger |
| 8,408,553 | B2 |   | 4/2013 | Eskildsen |
| 8,444,499 | B2 |   | 5/2013 | Balardeta et al. |
| 8,480,517 | B2 |   | 7/2013 | Guttler |
| 8,506,370 | B2 |   | 8/2013 | Homsi |
| 8,517,870 | B2 |   | 8/2013 | Crowley et al. |
| 8,540,560 | B2 |   | 9/2013 | Crowley et al. |
| 8,550,063 | B2 |   | 10/2013 | Alger |
| 8,579,632 | B2 |   | 11/2013 | Crowley |
| 8,597,095 | B2 |   | 12/2013 | Crowley et al. |
| 8,597,142 | B2 |   | 12/2013 | Mayles et al. |
| 8,622,843 | B2 |   | 1/2014 | Fuccillo et al. |
| 8,705,799 | B2 |   | 4/2014 | White et al. |
| 8,758,172 | B2 |   | 6/2014 | Creguer |
| 8,840,483 | B1 |   | 9/2014 | Steusloff et al. |
| 8,844,933 | B2 |   | 9/2014 | Eskildsen |
| 8,858,371 | B2 |   | 10/2014 | Rockoff |
| 8,893,698 | B2 |   | 11/2014 | Boehner |
| 8,911,308 | B2 |   | 12/2014 | Daniels |
| 8,951,106 | B2 |   | 2/2015 | Crowley et al. |
| 8,959,555 | B2 |   | 2/2015 | Monari et al. |
| 8,992,346 | B1 |   | 3/2015 | Raposo |
| 9,010,309 | B2 |   | 4/2015 | Lewis et al. |
| 9,017,188 | B2 |   | 4/2015 | Joseph et al. |
| 9,028,346 | B2 |   | 5/2015 | Melin |
| 9,039,547 | B2 |   | 5/2015 | Yeager |

(56) References Cited

U.S. PATENT DOCUMENTS

| | | |
|---|---|---|
| 9,050,519 B1 | 6/2015 | Ehlers et al. |
| 9,199,148 B2 | 12/2015 | Krohl et al. |
| 9,266,002 B2 | 2/2016 | Dunser |
| 9,398,213 B1 | 7/2016 | Cronin et al. |
| 9,415,263 B2 | 8/2016 | DeCarlo |
| 9,433,841 B2 | 9/2016 | Siefker |
| 9,452,339 B1 | 9/2016 | Shah et al. |
| 9,457,249 B2 | 10/2016 | Goldberg |
| 9,555,306 B2 | 1/2017 | Lewis et al. |
| 9,573,035 B2 | 2/2017 | DeCarlo |
| 9,586,099 B2 | 3/2017 | Holthouse |
| 9,625,321 B2 | 4/2017 | Cavallaro et al. |
| 9,700,777 B2 | 7/2017 | Dilz, Jr. |
| 9,724,585 B2 | 8/2017 | Peterson |
| 9,726,479 B2 * | 8/2017 | Rosen .................... G01B 11/14 |
| 9,739,576 B1 | 8/2017 | Venigalla |
| 9,770,638 B2 | 9/2017 | Argiro et al. |
| 9,782,648 B2 | 10/2017 | DeCarlo |
| 9,901,776 B2 | 2/2018 | Mettler |
| 9,901,804 B2 | 2/2018 | Vollbrecht et al. |
| 9,924,108 B2 | 3/2018 | Lindner et al. |
| 9,968,837 B2 | 5/2018 | Johnston |
| 9,999,823 B2 | 6/2018 | Chen et al. |
| 10,092,793 B1 | 10/2018 | Marty et al. |
| 10,118,078 B2 | 11/2018 | Lewis et al. |
| 10,252,128 B2 | 4/2019 | Lewis et al. |
| 10,322,328 B1 | 6/2019 | Hart |
| 10,471,330 B1 | 11/2019 | Hart |
| 10,744,383 B2 | 8/2020 | Lewis et al. |
| 2001/0056000 A1 | 12/2001 | Hori |
| 2002/0042312 A1 | 4/2002 | Decloux |
| 2002/0052255 A1 | 5/2002 | Trevino |
| 2002/0148455 A1 | 10/2002 | Trajkovic et al. |
| 2003/0008731 A1 | 1/2003 | Anderson et al. |
| 2003/0092497 A1 | 5/2003 | Holcomb |
| 2003/0109322 A1 | 6/2003 | Funk et al. |
| 2003/0142210 A1 | 7/2003 | Carlbom et al. |
| 2003/0195052 A1 | 10/2003 | Cohen et al. |
| 2003/0207718 A1 | 11/2003 | Perlmutter |
| 2004/0058749 A1 | 3/2004 | Pirritano et al. |
| 2004/0061324 A1 | 4/2004 | Howard |
| 2004/0063521 A1 | 4/2004 | Oister et al. |
| 2004/0171388 A1 | 9/2004 | Couronne et al. |
| 2004/0176192 A1 | 9/2004 | Slavey et al. |
| 2004/0185952 A1 | 9/2004 | Marshall |
| 2005/0069853 A1 | 3/2005 | Tyson et al. |
| 2005/0085320 A1 | 4/2005 | Joseph et al. |
| 2005/0143199 A1 | 6/2005 | Saroyan |
| 2005/0197198 A1 | 9/2005 | Otten et al. |
| 2005/0209027 A1 | 9/2005 | Joseph |
| 2005/0227792 A1 | 10/2005 | McCreary et al. |
| 2005/0242508 A1 | 11/2005 | Meichner |
| 2005/0272517 A1 | 12/2005 | Funk et al. |
| 2005/0288119 A1 | 12/2005 | Wang et al. |
| 2005/0288133 A1 | 12/2005 | Rudell |
| 2006/0025282 A1 | 2/2006 | Redmann |
| 2006/0042611 A1 | 3/2006 | Karellas |
| 2006/0118096 A1 | 6/2006 | Cucjen et al. |
| 2006/0135290 A1 | 6/2006 | Lin |
| 2006/0135297 A1 | 6/2006 | Cruciani |
| 2006/0148594 A1 | 7/2006 | Saintoyant et al. |
| 2006/0231082 A1 | 10/2006 | Soberg |
| 2006/0236993 A1 | 10/2006 | Cucjen et al. |
| 2006/0247070 A1 | 11/2006 | Funk et al. |
| 2006/0273522 A1 | 12/2006 | Marshall et al. |
| 2006/0281061 A1 | 12/2006 | Hightower et al. |
| 2007/0004539 A1 | 1/2007 | Meichner |
| 2007/0021226 A1 | 1/2007 | Tyroler |
| 2007/0026975 A1 | 2/2007 | Marty et al. |
| 2008/0026877 A1 | 1/2008 | Neel |
| 2008/0032826 A1 | 2/2008 | Mubarak et al. |
| 2008/0032828 A1 | 2/2008 | Alger |
| 2008/0058128 A1 | 3/2008 | Joseph |
| 2008/0085790 A1 | 4/2008 | Englert |
| 2008/0146365 A1 | 6/2008 | Miesak |

| | | |
|---|---|---|
| 2008/0192116 A1 | 8/2008 | Tamir et al. |
| 2008/0246221 A1 | 10/2008 | O'Sullivan |
| 2008/0252015 A1 * | 10/2008 | Eskildsen ............ A63B 43/004<br>273/371 |
| 2008/0287207 A1 | 11/2008 | Manwaring |
| 2009/0029754 A1 | 1/2009 | Slocum et al. |
| 2009/0047645 A1 | 2/2009 | Dibenedetto et al. |
| 2009/0048039 A1 | 2/2009 | Holthouse et al. |
| 2009/0048044 A1 | 2/2009 | Oleson et al. |
| 2009/0048070 A1 | 2/2009 | Vincent et al. |
| 2009/0095273 A1 | 4/2009 | Paulson et al. |
| 2009/0210078 A1 | 8/2009 | Crowley |
| 2009/0298650 A1 | 12/2009 | Kutliroff |
| 2009/0325739 A1 | 12/2009 | Gold |
| 2010/0151955 A1 | 6/2010 | Holden |
| 2010/0184496 A1 * | 7/2010 | Nicora ................... A63B 69/36<br>463/5 |
| 2010/0184534 A1 | 7/2010 | Chan et al. |
| 2010/0184563 A1 | 7/2010 | Molyneux et al. |
| 2010/0204616 A1 | 8/2010 | Shears et al. |
| 2010/0210377 A1 | 8/2010 | Lock |
| 2010/0252015 A1 | 10/2010 | Cucjen et al. |
| 2010/0261557 A1 | 10/2010 | Joseph et al. |
| 2010/0285905 A1 | 11/2010 | Guttler |
| 2011/0028230 A1 | 2/2011 | Balardeta et al. |
| 2011/0073091 A1 | 3/2011 | Gowan et al. |
| 2011/0118062 A1 | 5/2011 | Krysiak et al. |
| 2011/0143848 A1 | 6/2011 | Balardeta et al. |
| 2011/0143849 A1 | 6/2011 | Balardeta et al. |
| 2011/0151986 A1 | 6/2011 | Denton et al. |
| 2011/0224025 A1 | 9/2011 | Balardeta et al. |
| 2011/0230273 A1 | 9/2011 | Niegowski et al. |
| 2011/0303207 A1 | 12/2011 | Shober et al. |
| 2012/0015753 A1 | 1/2012 | Denton et al. |
| 2012/0015754 A1 | 1/2012 | Balardeta et al. |
| 2012/0029666 A1 | 2/2012 | Crowley et al. |
| 2012/0058845 A1 | 3/2012 | Crowley et al. |
| 2012/0129138 A1 | 5/2012 | Redmann |
| 2012/0152790 A1 | 6/2012 | Houvener et al. |
| 2012/0172148 A1 | 7/2012 | Freeman |
| 2012/0231906 A1 | 9/2012 | Barry et al. |
| 2012/0238381 A1 | 9/2012 | Denton et al. |
| 2012/0303207 A1 | 11/2012 | Reindl |
| 2012/0309554 A1 | 12/2012 | Gibbs et al. |
| 2012/0322568 A1 | 12/2012 | Lindeman |
| 2013/0005512 A1 | 1/2013 | Joseph et al. |
| 2013/0018494 A1 | 1/2013 | Amini |
| 2013/0023362 A1 | 1/2013 | Siefker |
| 2013/0079906 A1 | 3/2013 | Crowley et al. |
| 2013/0104869 A1 | 5/2013 | Lewis et al. |
| 2013/0104870 A1 | 5/2013 | Rizzo et al. |
| 2013/0157786 A1 | 6/2013 | Joseph et al. |
| 2013/0210563 A1 | 8/2013 | Hollinger |
| 2013/0225305 A1 | 8/2013 | Yang et al. |
| 2013/0317634 A1 | 11/2013 | French et al. |
| 2013/0324310 A1 | 12/2013 | Leech et al. |
| 2014/0031151 A1 | 1/2014 | Crowley et al. |
| 2014/0039651 A1 | 2/2014 | Crowley |
| 2014/0081436 A1 | 3/2014 | Crowley et al. |
| 2014/0128171 A1 | 5/2014 | Anderson |
| 2014/0369695 A1 | 12/2014 | D'Andrade et al. |
| 2015/0202508 A1 | 7/2015 | Wise, Jr. |
| 2015/0246275 A1 | 9/2015 | Goldberg |
| 2015/0283443 A1 | 10/2015 | Dunser |
| 2015/0352425 A1 | 12/2015 | Lewis et al. |
| 2016/0008662 A1 | 1/2016 | Cronin et al. |
| 2016/0016059 A1 | 1/2016 | Martinez |
| 2016/0023042 A1 | 1/2016 | Cherry |
| 2016/0023083 A1 | 1/2016 | Tawwater et al. |
| 2016/0074735 A1 | 3/2016 | Dawe et al. |
| 2016/0136504 A1 | 5/2016 | Cuttino |
| 2016/0158626 A1 | 6/2016 | Dolige et al. |
| 2016/0354664 A1 | 12/2016 | DeCarlo |
| 2017/0021259 A1 | 1/2017 | Dismuke |
| 2017/0095716 A1 | 4/2017 | Lewis et al. |
| 2017/0120132 A1 | 5/2017 | Shin et al. |
| 2017/0157482 A1 | 6/2017 | DeCarlo |
| 2017/0182361 A1 | 6/2017 | Tuxen et al. |
| 2017/0189753 A1 | 7/2017 | Polifka |

(56) References Cited

U.S. PATENT DOCUMENTS

| | | |
|---|---|---|
| 2017/0189773 A1 | 7/2017 | Cho |
| 2017/0189794 A1 | 7/2017 | Hatton et al. |
| 2017/0197126 A1 | 7/2017 | Richter |
| 2017/0203177 A1 | 7/2017 | Chiu |
| 2017/0203182 A1 | 7/2017 | Spelman et al. |
| 2017/0209748 A1 | 7/2017 | Kim |
| 2017/0216695 A1 | 8/2017 | Schlagenhauf |
| 2017/0232316 A1 | 8/2017 | Chu |
| 2017/0239542 A1 | 8/2017 | Seto |
| 2017/0239543 A1 | 8/2017 | Seto |
| 2017/0239544 A1 | 8/2017 | Scott |
| 2017/0259144 A1 | 9/2017 | Eddie |
| 2017/0259145 A1 | 9/2017 | Kline |
| 2017/0266525 A1 | 9/2017 | Mems-McNair et al. |
| 2017/0274247 A1 | 9/2017 | Miyasaka et al. |
| 2017/0274262 A1 | 9/2017 | Sanchez et al. |
| 2017/0291093 A1 | 10/2017 | Janssen |
| 2017/0304705 A1 | 10/2017 | Hermandorfer |
| 2017/0319930 A1 | 11/2017 | Lewis et al. |
| 2017/0333777 A1 | 11/2017 | Spivak et al. |
| 2017/0340943 A1 | 11/2017 | Pierotti et al. |
| 2018/0036590 A1 | 2/2018 | DeAngelis et al. |
| 2018/0036616 A1 | 2/2018 | McKenney |
| 2018/0056124 A1 | 3/2018 | Marty et al. |
| 2018/0071577 A1 | 3/2018 | Swartz et al. |
| 2018/0093133 A1 | 4/2018 | Decarlo |
| 2018/0140917 A1 | 5/2018 | Song et al. |
| 2019/0060728 A1 | 2/2019 | Lewis et al. |
| 2019/0091535 A1 | 3/2019 | DeCarlo |
| 2021/0031081 A1 | 2/2021 | Lewis et al. |

FOREIGN PATENT DOCUMENTS

| | | | |
|---|---|---|---|
| AU | 2017101162 | A4 | 9/2017 |
| CA | 2476010 | A1 | 1/2005 |
| CA | 2676348 | A1 | 2/2011 |
| CA | 2931744 | A1 | 12/2014 |
| CN | 2892188 | Y | 4/2007 |
| CN | 1824352 | B | 4/2010 |
| CN | 102389634 | A | 3/2012 |
| CN | 202223857 | U | 5/2012 |
| CN | 103706088 | A | 4/2014 |
| CN | 205964896 | U | 2/2017 |
| CN | 104504694 | B | 7/2017 |
| CN | 105582659 | B | 9/2017 |
| DE | 19938761 | A1 | 2/2001 |
| DE | 203 05 276 | U1 | 6/2003 |
| DE | 102015225776 | A1 | 6/2017 |
| DK | 177133 | B1 | 1/2012 |
| EP | 0400325 | A2 | 12/1990 |
| EP | 1477825 | A1 | 11/2004 |
| EP | 1897599 | A2 | 3/2008 |
| EP | 1457236 | B1 | 6/2008 |
| EP | 2227299 | A2 | 9/2010 |
| EP | 2218483 | B1 | 3/2017 |
| EP | 3188810 | A1 | 7/2017 |
| EP | 3242728 | A1 | 11/2017 |
| FR | 3012743 | A1 | 5/2015 |
| GB | 2142546 | A | 1/1985 |
| GB | 2196859 | B | 5/1991 |
| GB | 2337385 | A | 11/1999 |
| GB | 2475833 | A | 6/2011 |
| GB | 2487047 | A | 7/2012 |
| GB | 2487209 | A | 7/2012 |
| GB | 2505417 | A | 3/2014 |
| GB | 2539837 | A | 12/2016 |
| GB | 2544561 | A | 5/2017 |
| GB | 2546112 | A | 7/2017 |
| GB | 2526338 | B | 9/2017 |
| JP | 2010112956 | A | 5/2010 |
| KR | 101579382 | B1 | 12/2015 |
| KR | 20160124254 | A | 10/2016 |
| KR | 1020170077969 | | 7/2017 |
| KR | 20170104700 | A | 9/2017 |
| KR | 1020170105192 | | 9/2017 |
| RU | 2626804 | C1 | 8/2017 |
| RU | 2628857 | C2 | 8/2017 |
| TW | M353032 | U | 3/2009 |
| TW | M551080 | U | 11/2017 |
| WO | 95/21661 | A1 | 8/1995 |
| WO | 2003032006 | A1 | 4/2003 |
| WO | 2006/081702 | A1 | 8/2006 |
| WO | 2007037705 | A1 | 4/2007 |
| WO | 2009/053848 | A2 | 4/2009 |
| WO | 2009138929 | A1 | 11/2009 |
| WO | 2010102037 | A2 | 9/2010 |
| WO | 2011106888 | A1 | 9/2011 |
| WO | 2012/138528 | A2 | 10/2012 |
| WO | 2014021549 | A1 | 2/2014 |
| WO | 2015112646 | A1 | 7/2015 |
| WO | 2016206412 | A1 | 12/2016 |
| WO | 2017116241 | A1 | 7/2017 |
| WO | 2017131262 | A1 | 8/2017 |

OTHER PUBLICATIONS

C. Spiteri, "System And Method For Object Tracking And Metric Generation," filed Aug. 13, 2020, U.S. Appl. No. 16/993,035 including its prosecution history.

C. Spiteri, "System And Method For Object Tracking Using A Subsection Of A Sequence Of Images," filed Jul. 14, 2023, U.S. Appl. No. 18/222,283 including its prosecution history.

C. Spiteri, "System And Method For Object Tracking," filed Aug. 13, 2020, U.S. Appl. No. 16/993,030 Including its prosecution history.

C. Spiteri, "System, Method And Apparatus For Object Tracking And Human Pose Estimation," filed Nov. 28, 2022, U.S. Appl. No. 17/994,834 including its prosecution history .

E. J. Lewis et al., "Ball Throwing Machine And Method," filed Feb. 9, 2015, U.S. Appl. No. 14/617,599 Including its prosecution history.

E. J. Lewis et al., "Ball Throwing Machine And Method," filed Jul. 27, 2017, U.S. Appl. No. 15/662,150 Including its prosecution history.

E. J. Lewis et al., "Ball Throwing Machine And Method," filed Nov. 2, 2011, U.S. Appl. No. 13/287,749 including its prosecution history.

E. J. Lewis et al., "Goal Apparatus," filed Sep. 19, 2018, U.S. Appl. No. 29/663,886 including its prosecution history.

E. J. Lewis et al., "System And Method For A User Adaptive Training And Gaming Platform," filed Dec. 27, 2021, U.S. Appl. No. 17/562,270 including its prosecution history.

E. J. Lewis et al., "System And Method For A User Adaptive Training And Gaming Platform," filed Nov. 15, 2019, U.S. Appl. No. 16/686,003 including its prosecution history.

E. J. Lewis et al., "System And Method For Object Tracking In Coordination With A Ball-Throwing Machine," filed Aug. 17, 2020, U.S. Appl. No. 16/995,289 including its prosecution history.

E. J. Lewis et al., "System, Apparatus And Method For An Intelligent Goal," filed Oct. 25, 2018, U.S. Appl. No. 16/171,127 including its prosecution history.

E. J. Lewis et al., "System, Apparatus And Method For Ball Throwing Machine And Intelligent Goal," filed Dec. 9, 2016, U.S. Appl. No. 15/374,984 including its prosecution history.

S. Plumer et al., "System And Method For Altering The Motion Of A Foosball," filed March, 7, 2023, U.S. Appl. No. 18/180,109 including its prosecution history.

S. Plumer et al., "System And Method For Foosball Table Implementing Playing Obstacles," filed March, 4, 2021, U.S. Appl. No. 17/192,766 including its prosecution history.

"Borussia Dortmund showcase The Footbonaut", https://www.youtube.com/watch?v=WhAyX81zP2M, dated Sep. 26, 2012.

"Kick-Point electronic soccer goal", https://www.youtube.com/watch?v=fjAVax966X0, dated May 8, 2014.

Anon., "Epipolar geometry" https://en.wikipedia.org/wiki/Epipolar_geometry, last accessed May 4, 2020.

EP 13883409.8 filed Nov. 24, 2015 European Search Report dated Nov. 17, 2016.

(56)        References Cited

OTHER PUBLICATIONS

EP 13883409.8 filed Nov. 24, 2015 Office Action dated Nov. 14, 2017.
Fitlight Trainer, https://www.fitlighttraining.com/ last accessed Mar. 30, 2023.
PCT/US2013/039143 filed May 1, 2013 International Search Report and Written Opinion dated Nov. 1, 2013.
Sensiwall—"Sensiwall develops field training systems for professional sports", https://www.dealmarket.com/#!/dealflows/755679/deals/1612053/details/internal, last accessed Sep. 11, 2016.
Slash Gear webpage, Adidas miCoach Smart Ball connects soccer to smartphone, http://www.slashgear.com/adidas-micoach-smart-ball-connects-soccer-to-sma-rtphone-27330732/, last accessed on Jun. 3, 2014.
U.S. Appl. No. 13/287,749, filed Nov. 2, 2011 Non-Final Office Action dated Jul. 11, 2014.
U.S. Appl. No. 13/287,749, filed Nov. 2, 2011 Notice of Allowance dated Dec. 2, 2014.
U.S. Appl. No. 14/617,599, filed Feb. 9, 2015 Final Office Action dated May 20, 2016.
U.S. Appl. No. 14/617,599, filed Feb. 9, 2015 Non-Final Office Action dated Sep. 23, 2015.
U.S. Appl. No. 14/617,599, filed Feb. 9, 2015 Notice of Allowance dated Sep. 22, 2016.
U.S. Appl. No. 15/374,984, filed Dec. 9, 2016 Non-Final Office Action dated Feb. 14, 2018.
U.S. Appl. No. 15/374,984, filed Dec. 9, 2016 Notice of Allowance dated Jul. 18, 2018.
U.S. Appl. No. 15/662,150, filed Jul. 27, 2017 Final Office Action dated Aug. 13, 2018.
U.S. Appl. No. 15/662,150, filed Jul. 27, 2017 Non-Final Office Action dated Jan. 16, 2018.
U.S. Appl. No. 16/171,127, filed Oct. 25, 2018 Noitice of Allowance dated Mar. 30, 2020.
U.S. Appl. No. 16/171,127, filed Oct. 25, 2018 Non-Final Office Action dated Oct. 11, 2019.
U.S. Appl. No. 16/995,289, filed Aug. 17, 2020, Advisory Action dated Aug. 22, 2022.
U.S. Appl. No. 16/995,289, filed Aug. 17, 2020, Final Office Action dated May 13, 2022.
U.S. Appl. No. 16/995,289, filed Aug. 17, 2020, Non-Final Office Action dated Dec. 6, 2021.
U.S. Appl. No. 16/995,289, filed Aug. 17, 2020, Notice of Allowance dated Oct. 5, 2022.
EP 251902474 filed Mar. 7, 2018 Extended European Search Report dated Sep. 19, 2025.

* cited by examiner

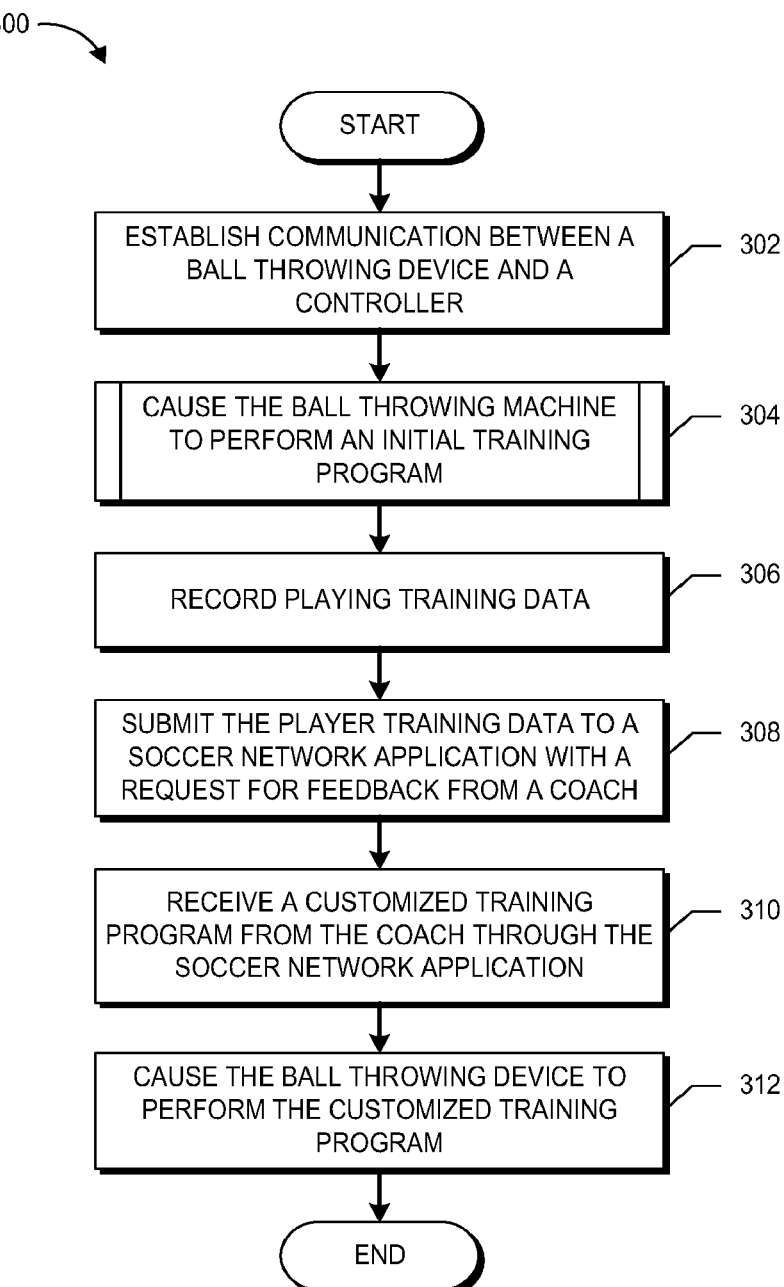

BALL MACHINE CONTROL PROCESS

300

START

ESTABLISH COMMUNICATION BETWEEN A BALL THROWING DEVICE AND A CONTROLLER — 302

CAUSE THE BALL THROWING MACHINE TO PERFORM AN INITIAL TRAINING PROGRAM — 304

RECORD PLAYING TRAINING DATA — 306

SUBMIT THE PLAYER TRAINING DATA TO A SOCCER NETWORK APPLICATION WITH A REQUEST FOR FEEDBACK FROM A COACH — 308

RECEIVE A CUSTOMIZED TRAINING PROGRAM FROM THE COACH THROUGH THE SOCCER NETWORK APPLICATION — 310

CAUSE THE BALL THROWING DEVICE TO PERFORM THE CUSTOMIZED TRAINING PROGRAM — 312

END

FIG. 8

TRAINING PROCESS

COACHING PROCESS

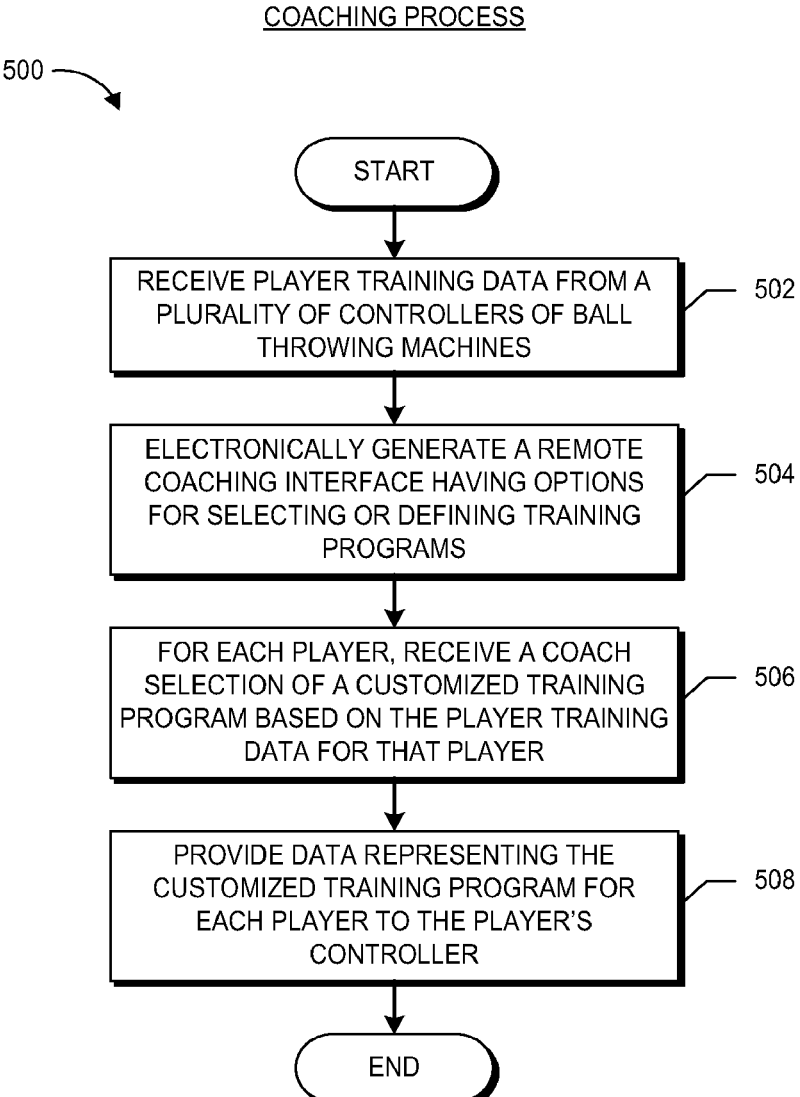

500

START

RECEIVE PLAYER TRAINING DATA FROM A PLURALITY OF CONTROLLERS OF BALL THROWING MACHINES — 502

ELECTRONICALLY GENERATE A REMOTE COACHING INTERFACE HAVING OPTIONS FOR SELECTING OR DEFINING TRAINING PROGRAMS — 504

FOR EACH PLAYER, RECEIVE A COACH SELECTION OF A CUSTOMIZED TRAINING PROGRAM BASED ON THE PLAYER TRAINING DATA FOR THAT PLAYER — 506

PROVIDE DATA REPRESENTING THE CUSTOMIZED TRAINING PROGRAM FOR EACH PLAYER TO THE PLAYER'S CONTROLLER — 508

END

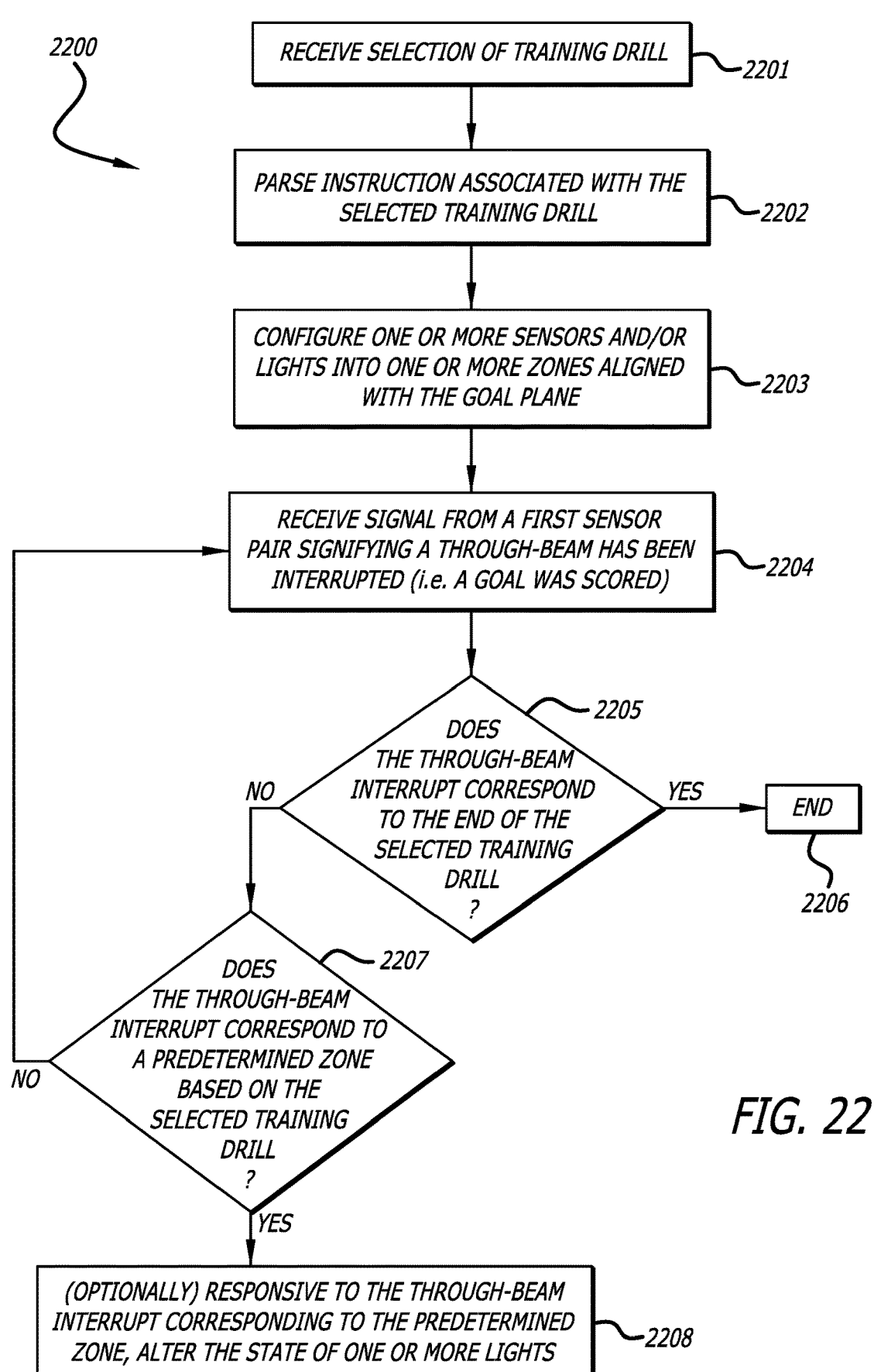

2200

RECEIVE SELECTION OF TRAINING DRILL ~2201

PARSE INSTRUCTION ASSOCIATED WITH THE SELECTED TRAINING DRILL ~2202

CONFIGURE ONE OR MORE SENSORS AND/OR LIGHTS INTO ONE OR MORE ZONES ALIGNED WITH THE GOAL PLANE ~2203

RECEIVE SIGNAL FROM A FIRST SENSOR PAIR SIGNIFYING A THROUGH-BEAM HAS BEEN INTERRUPTED (i.e. A GOAL WAS SCORED) ~2204

DOES THE THROUGH-BEAM INTERRUPT CORRESPOND TO THE END OF THE SELECTED TRAINING DRILL ? ~2205

NO          YES

END ~2206

DOES THE THROUGH-BEAM INTERRUPT CORRESPOND TO A PREDETERMINED ZONE BASED ON THE SELECTED TRAINING DRILL ? ~2207

NO

YES (OPTIONALLY) RESPONSIVE TO THE THROUGH-BEAM INTERRUPT CORRESPONDING TO THE PREDETERMINED ZONE, ALTER THE STATE OF ONE OR MORE LIGHTS ~2208

FIG. 22

DETECTION OF THE SPEED OF AN OBJECT PASSING THROUGH A GOAL PLANE

CROSS-REFERENCE TO RELATED APPLICATIONS

This application is a continuation of U.S. application Ser. No. 16/995,289 filed on Aug. 17, 2020, which is a continuation of U.S. application Ser. No. 16/171,127 filed on Oct. 25, 2018, now U.S. Pat. No. 10,744,383 issued on Aug. 18, 2020, which is a continuation of U.S. application Ser. No. 15/374,984, filed Dec. 9, 2016, now U.S. Pat. No. 10,118, 078 issued Nov. 6, 2018, which is a continuation-in-part of U.S. application Ser. No. 14/617,599, filed Feb. 9, 2015, now U.S. Pat. No. 9,555,306 issued Jan. 31, 2017, which is a continuation of U.S. application Ser. No. 13/287,749, filed Nov. 2, 2011, now U.S. Pat. No. 9,010,309, issued Apr. 21, 2015, the entire contents of each are incorporated by reference herein.

FIELD

Embodiments of the disclosure relate to the field of soccer goals and soccer ball-providing machines. More specifically, one embodiment of the disclosure relates to a system and apparatus of a soccer goal that includes a plurality of sensors to detect when a ball breaks the plane of the goal line.

BACKGROUND

In soccer, to be in control of the ball is of importance to every level of player. The ability to control an awkward bouncing ball quickly and effectively gives the player with the ball the immediate advantage. First touch is often the difference between success and failure in most situations during the match. Additionally, accuracy in passing and shooting a ball is essential in developing a well-rounded game.

As players get older, the game gets faster and demands more speed. Consequently, there is a greater need for accurate shooting and passing. Often, players cannot always place a ball, either to score a goal or even to place a shot within a specific location of the goal—e.g., out of the reach of the goalie; therefore, a player may miss out on an opportunity to score a goal.

Players can improve the accuracy of their shooting and passing by performing shooting and passing drills. Often, however, a player is unable to concentrate on keeping track of the location of each pass or shot within a goal or other area during drills involving several balls. Therefore, by the end of the drill, a player typically does not remember his/her accuracy and cannot determine whether he/she is improving based on results of previous drills.

SUMMARY

Certain aspects, advantages and novel features of the inventions are described herein. It is to be understood that not necessarily all such advantages may be achieved in accordance with any particular embodiment of the inventions disclosed herein. Thus, the inventions disclosed herein may be embodied or carried out in a manner that achieves or selects one advantage or group of advantages as taught herein without necessarily achieving other advantages as may be taught or suggested herein.

BRIEF DESCRIPTION OF THE DRAWINGS

The features disclosed herein are described below with reference to the drawings. Throughout the drawings, reference numbers are re-used to indicate correspondence between referenced elements. The drawings are provided to illustrate embodiments of the inventions described herein and not to limit the scope thereof.

FIG. 8 illustrates an embodiment of a ball machine control process that may be implemented by the controller of FIG. 6.

FIG. 10 illustrates an embodiment of a coaching process that may be implemented at least in part by the soccer network application of FIG. 7.

FIG. 22 is a flowchart illustrating an exemplary method for configuring and operating the intelligent goal according to a selected training drill.

DETAILED DESCRIPTION

I. Introduction

Figure 1:
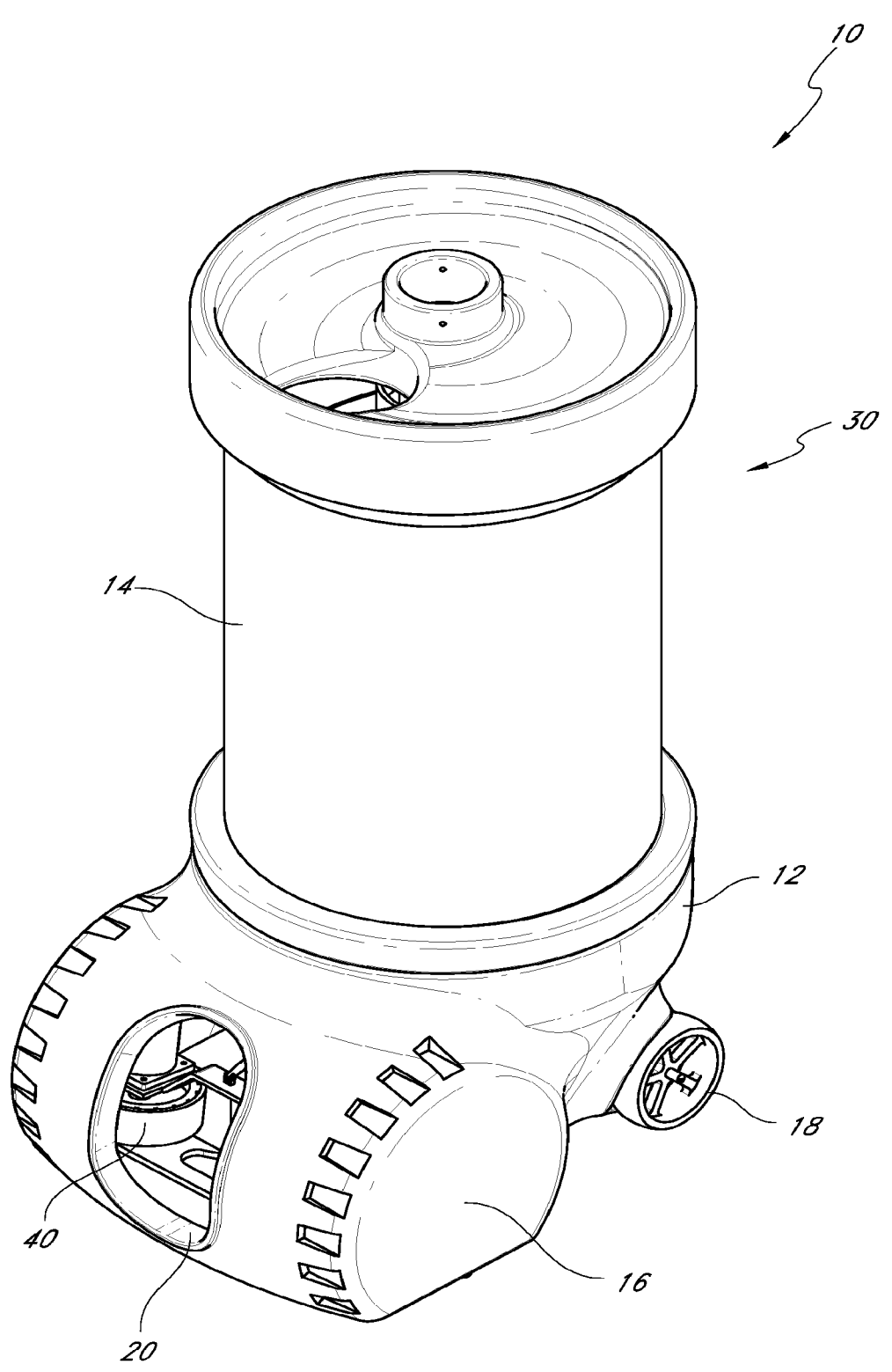
FIG. 1 is a perspective view of a ball-throwing machine.

As described above, a soccer player's first touch of the ball is an important core skill to develop. A touch can be as simple as receiving a slow pass on the ground or as difficult as taking a top speed knuckling ball out of the air and straight down onto one's foot. First touch development is a continual process; youth and professionals alike perpetually train to ever improve their first touch and ball handling skills. The skill of touch is typically trained by players forming pairs and passing the ball to one another. This training method can produce results but tends to fall short in providing a disciplined approach to training that enables progress measurement and goal-oriented improvement. Further, this technique requires a player to find another individual with which to practice, which is not always practical, particularly for serious athletes who devote significant time to their training.

This disclosure describes a specialized ball-throwing machine that can be used to improve a player's first touch and ball control, among other benefits. The ball-throwing machine can be designed to throw, lob, pitch, or otherwise eject soccer balls toward a player, who can trap the balls or practice other ball control skills. The ball-throwing machine may be controlled using a controller in the form of a handheld computing device or the like. The controller can include software and hardware that enables the player to remotely control the machine, for example, wirelessly. The controller can include functionality for recording a player's progress with ball training, and the player can upload this progress information to a software network application, which may be a web site or the like. The soccer network application can provide functionality for a remote coach to analyze the player's progress and provide a customized training program to the player based on the player's progress. As a result, the ball-throwing machine can enable the player to track progress and receive remote coaching to improve that progress. These and other features of the ball throwing machine, controller, and associated soccer network application are described in detail below. In addition, this disclosure describes an "intelligent goal" that combines a traditional soccer goal with at least a plurality of sensors and logic to determine when a goal was scored and the placement of the ball as the goal was scored. Additionally, the intelligent goal may include one or more lights and/or one or more speakers. The sensors, lights and speakers may be integrated in the side posts or crossbar of the intelligent goal. The intelligent goal may include a plurality of sensor pairs such that a first sensor of the sensor pair is integrated in a first side post and a second sensor of the sensor pair is integrated in a second side post and aligned horizontal to the first sensor. A beam (e.g., a light beam) may be transmitted from the first sensor to the second sensor such that a goal is detected when a ball interrupts the light beam. Based on the location of the sensor pair along the side posts, the placement of the ball while scoring the goal is known. One or more lights may be integrated within the side posts and/or cross bar and, controlled by logic of the intelligent goal, be turned on or off according to aspects of a drill for which the intelligent goal is being used. Further, one or more speakers may be coupled to or integrated in the cross bar or side posts and, controlled by logic of the intelligent goal, provided audible cues according to aspects of a drill for which the intelligent goal is being used.

The game of soccer is commonly known in some countries as "football" or "association football." For convenience, this specification refers solely to the term "soccer," although such usage should be considered synonymous with "football" and "association football." Further, embodiments of the ball throwing machine, controller, and soccer network application described herein can be used or adapted for sports other than soccer, some examples of which are described below.

It should also be noted that although this specification refers primarily to using a ball-throwing machine to train ball trapping skills, the ball-throwing machine can be used to train other skills. For example, the ball throwing machine can be used to train passing, shooting, and stopping a soccer ball, among other ball skills.

II. Example Ball Throwing Machine

A ball throwing machine 10 is shown in FIG. 1. The ball throwing machine 10 can be used to pitch a ball, such as to deliver a ball to a user. For example, the ball throwing machine 10 can be used to deliver a soccer ball or a specialized soccer-type ball to a user. The ball throwing machine 10 can also be used with various other balls for various other sports.

The illustrated ball throwing machine 10 includes an outer housing 12 with an upper section 14 and a lower section 16. The ball throwing machine 10 can be that can be easily movable. For example, the ball throwing machine can include one or more motorized wheels 18. Some embodiments may also include one or more handles for securing the ball throwing machine while moving the same.

Figure 2:
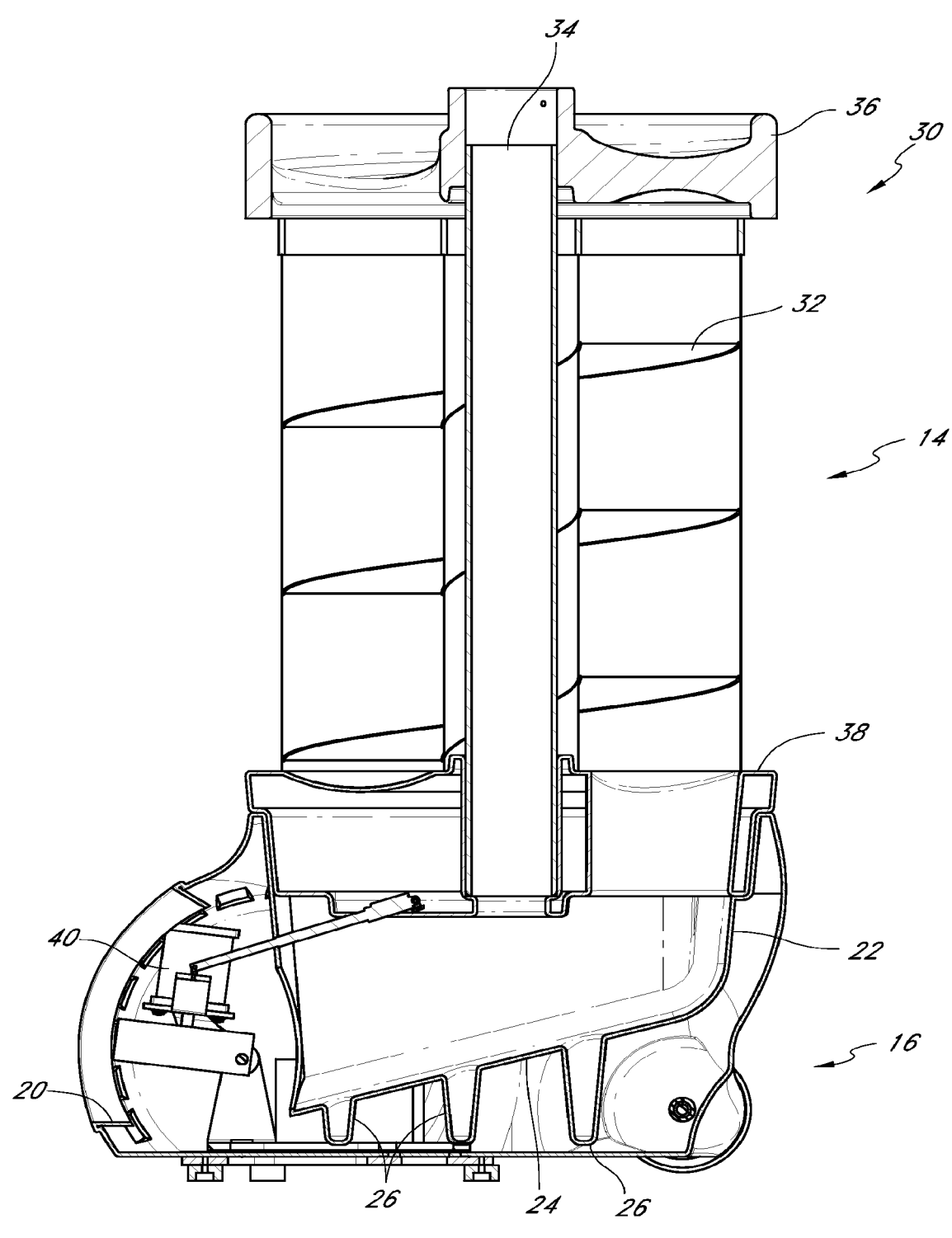
FIG. 2 is a cross-section of the ball-throwing machine of FIG. 1.

As can be seen in FIGS. 1 and 2, the upper section 14 includes a hopper 30. The hopper 30 can be used to receive and/or store balls to later be ejected or thrown by the ball throwing machine 10. The illustrated embodiment includes a high-volume or large storage-type hopper 30. In some embodiments, the hopper can store as many as 25 balls. Of course, it will be understood that the hopper could hold more or less balls, as necessary or desired.

Many different styles and types of hoppers can be used. As shown, the hopper 30 is a gravity-type hopper with a spiraling ramp 32 located around and internal tube 34. The tube 34 can be used to impart structural strength to the hopper and can also provide appropriate spacing such that balls within the hopper are able to properly rotate and move downward in the hopper. Alternatively, the tube 34 is not included in some embodiments. Rather, the hopper 30 merely includes the spiraling ramp 32. In another embodiment, the spiraling ramp 32 is omitted and the hopper 30 includes a tube 34 that holds a plurality of balls.

In some embodiments, the hopper 30 can be transparent. For example, the outer material of the hopper may be clear Plexiglas or plastic, or a thin mesh-like fabric. This transparency can allow the user to view the balls in the hopper 30 and identify when the hopper 30 needs to be reloaded. The hopper 30 can have a top portion 36 and a bottom portion 38. The top portion 36 can be configured for receiving one or more balls into the hopper 30 and in some embodiments, can hold additional balls. The bottom portion can be configured to transition balls from the hopper 30 into a ball staging area 42.

The hopper 30 can be used for storing balls when the ball throwing machine 10 is in use and/or when the ball throwing machine 10 is not in use. In some embodiments, the hopper 30 can be collapsible or detachable to decrease the size of the ball throwing machine 10, such as when the ball throwing machine is not in use. In some embodiments, the tube 34 can be a telescoping tube and the outer material of the hopper 30 can be fabric, such that the hopper 30 can increase or decrease in size. In some embodiments with the collapsible hopper 30, the top portion 36 can be collapsed to sit on top of the bottom portion 38. Alternatively, the tube 34 can be configured to be removable to remove structural support separating the top portion 36 from the bottom portion 38.

Advantageously, in certain embodiments, the ball throwing machine 10 is designed to deliver soccer balls that are smaller than adult regulation size soccer balls to thereby enable more effective training of ball trapping skills. The smaller surface area of such balls can make the smaller balls harder to trap than regulation size balls (such as size "5" soccer balls). Training with smaller balls can therefore benefit a player using a larger, regulation-size ball in a match because the player may have obtained skills that transfer over to the easier-to-trap, larger ball. In some embodiments, the balls used with the ball throwing machine 10 are about half the size of regulation size 5 balls, about a third of the size of regulation size 5 balls, about a quarter of the size of regulation size balls 5, or some other size. For youth players who may already be using a smaller ball than an adult ball in matches, the ball throwing machine 10 can employ even smaller balls than the youth players use in their matches. For instance, if youth player is used to using size 4 soccer balls, the ball throwing machine can throw size 3 soccer balls or smaller, etc. However, in other embodiments, regulation size balls are used instead of smaller balls.

The size of the balls used by the ball throwing machine 10 can be smaller than a regulation size 3 ball, even for older youth and adult players. For example, in one embodiment, the balls are preferably about 152 mm in diameter. However, in other embodiments the balls can range in size from about 132 mm to about 172 mm in diameter while still providing some or all of the benefits of the balls described herein. In still other embodiments, the balls can range in size from about 115 mm to 215 mm in diameter while still providing at least some of the benefits described herein.

A ball that may be used herein may have any of the following characteristics: a rubber construction, a butyl bladder, one or more nylon plys (such as 1, 2, 3, or 4 or more nylon plys), spiral winding of the nylon plys, and the like. These and other characteristics of the balls, among others (including size, texture, weight, cover type, etc.) can be selected to achieve a desired liveliness or bounciness of the ball. Different balls may be provided with different liveliness for different levels of difficulty. For instance, a ball that has more bounce may be harder to trap and thus appropriate for a higher level of difficulty, while a ball with less bounce may be easier to trap and thus appropriate for a lower level of difficulty.

Moreover, the colors of the balls can be selected to target foot-eye coordination. For example, the balls may be blue, green, or red, or a combination of the same, as these colors can be the easier to see than other colors. Alternatively, colors may be selected that are less easy to see so as to increase the difficulty of training. Different colors may be provided for boys and girls, who may perceive colors slightly differently.

In one embodiment, the balls are not actual soccer balls. For example, a ball having a smaller size than a regulation size ball can be considered to be a ball other than a soccer ball. Counterintuitively, it can be beneficial to train soccer skills (such as trapping) using balls that are not soccer balls, such as any of the balls described herein. Balls used in other sports can also be thrown by the ball throwing machine 10 for the purposes of training soccer skills. Tennis balls, racquet balls, and squash balls, for instance, can be beneficially used to train trapping skills.

Moving now to the bottom portion 16 of the outer housing 12, the bottom portion 16 is shown housing the ball staging area 42, as well as the ball delivery device 40. As can be seen in FIG. 2, the ball staging area 42 can include a ramp 24 that can hold one or more balls. The ramp 24 can include one or more ball stops 26. The ball stops can be used to stop individual balls or the balls collectively.

For example, as shown, the ball staging area 42 includes three ball stops 26. In some embodiments, the ball stops 26 can include a solenoid configured to advance and/or retract a rod or other member in front of a ball. The three balls stops 26 can allow the ball throwing machine 10 to control the projection of the ball completely with the ball delivery device 40. For example, separating the balls with multiple ball stops 26 can allow the ball delivery device 40 to pitch a ball without the influence of other balls acting or pushing upon the ball. It will be understood that the balls in the hopper may be pressing down on one another by gravity and could have an influencing effect on the trajectory of the ball, if allowed to contact the ball being pitched. However, fewer than three ball stops 26 may be included in the machine 10 instead.

As is shown, the bottom portion 16 of the outer housing also includes at least one opening 20. The opening 20 can provide space for the ball to be thrown through to the user. The opening 20 can be one of many different shapes, such as oval, elliptical, rectangular, triangular, or any other desired shape. In some embodiments, the bottom portion 16 of the outer housing 12 includes a minimal amount of material, such that a majority, or at least a substantial portion, of the ball delivery device 40 is exposed and not enclosed. In such embodiments, little to no portion of the outer housing may be between the ball delivery device 40 and the user.

Figure 3:
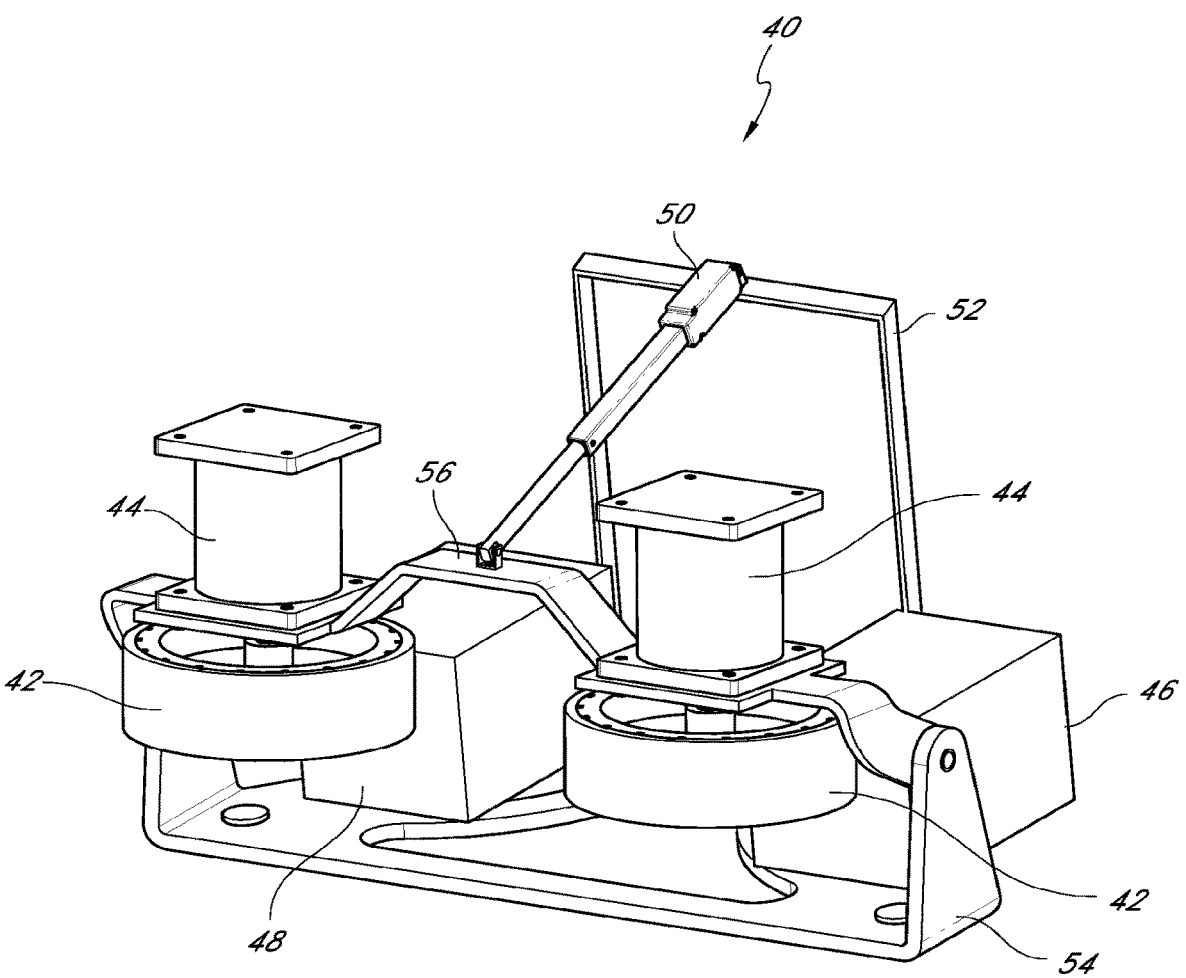
FIG. 3 shows some of the internal components of the ball-throwing machine including portions of a ball delivery device.

Turning now to FIG. 3, an embodiment of a ball delivery device 40 is shown. A ball delivery device 40 can include any number of various components. The ball delivery device 40 can be used to impart motion to a ball. In some embodiments, the ball delivery device 40 can be used to control the trajectory of the ball, including the speed and angle at which the ball leaves the ball throwing machine 10. The ball delivery device 40 can perform these functions in various different manners including those described below. It is to be understood that the ball delivery device 40 also encompasses various other systems and methods of performing the above functions, as well as, other, additional and/or alternative functions.

As illustrated, the ball delivery device 40 includes one or more wheels or balls 42 which are used to impart speed, spin, and/or other features of trajectory to a ball. The ball delivery device 40 can also include one or more motors 44 which are connected to the wheels 42 to thereby deliver speed and direction to the wheels 42. The ball delivery device 40 can also include a control unit 46 and a power source 48, such as batteries. The control unit 46 can include various features that can be used to control the ball delivery device 40. For example, the control unit 46 can include electronic circuitry, a processor, and memory having program instructions stored thereon for controlling the various electrical features of the ball delivery device 40, such as the motorized wheels 18 and actuators (described below). Further, the control unit 46 can include a wireless network interface card (NIC) and antenna or wired NIC for communicating with a controller device that sends commands to the ball throwing machine 10, as described below with respect to FIG. 6.

The ball delivery device 40 may also include one or more actuators 50. The actuator 50 can be used to control an angle of the ball delivery device, including the wheels 42. The ball delivery device 40 can include a frame having one or more brackets 52, 54. The brackets 52, 54 can be positioned in fixed relationship with one another. As shown, the actuator 50 is connected to at one end to bracket 52 and at an opposite end to bracket 56. The bracket 56 can be attached to the wheels and in some embodiments, the motors 44. The bracket 56 can also be hingedly attached to bracket 54. The actuator 50 can move to increase or decrease the length of the actuator.

In the illustrated position of FIG. 3, the longitudinal axis of each wheel 42, about which the wheel rotates, is generally vertical. Moving the actuator 50 can change this position and orientation of the axis and wheel 42 as changing the length of the actuator 50 can change the angle or positional relationship between the bracket 56 and the frame, including brackets 52 and 54. When the actuator 50 is lengthened, the distance between the bracket 52 and parts of the bracket 56 is increased. When the actuator 50 is shortened, parts of the bracket 56 are moved closer to the bracket 52. This can result in the axis moving either upward or downward towards a horizontal orientation. It will be understood that changing the angle of the wheels 42 can change the trajectory of the ball when it is ejected.

Moving now to FIGS. 4 and 5, another feature of the ball delivery device 40 will be described. The ball delivery device 40 can also include features to change the side-to-side trajectory of the ball. As can be seen, an actuator 50 can be located on the bottom of the ball throwing machine 10. Such an actuator can be located either internally or externally of the outer housing 12. A bracket 58 can be connected to the bracket 54 through a turntable 60. Such a connection can allow the bracket 54 to move with respect to the bracket 58. The actuator 50 can be connected to both brackets 54, 58 such that movement of the actuator 50 can change the positional relationship of portions of the bracket 54 with the bracket 58.

Figure 4:
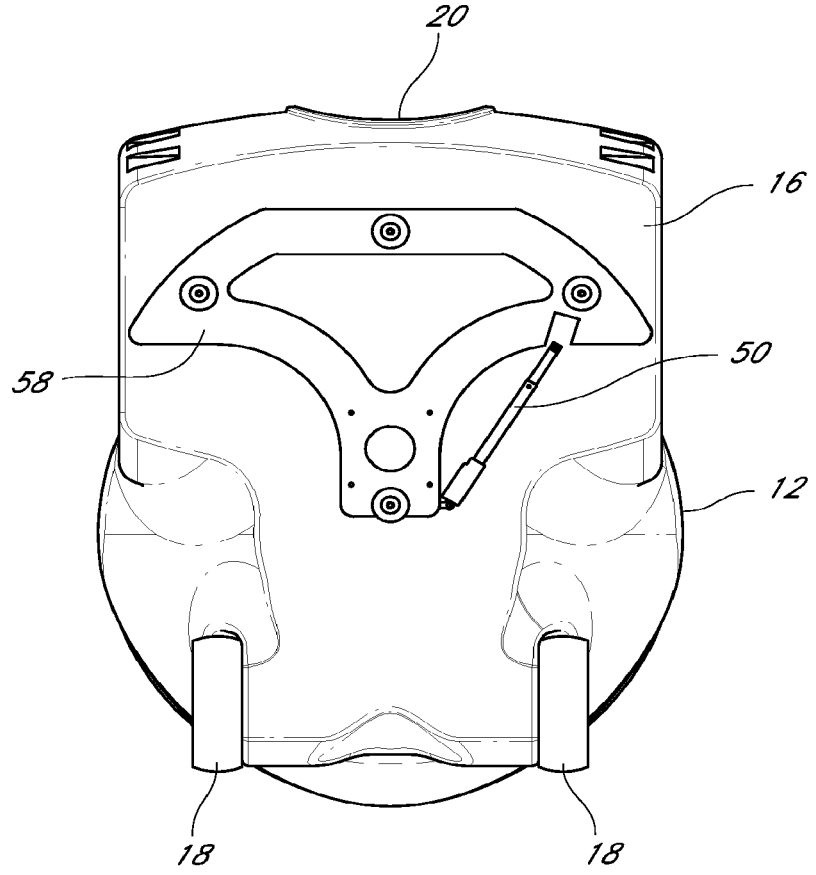
FIG. 4 illustrates the bottom of the ball-throwing machine.
Figure 5:
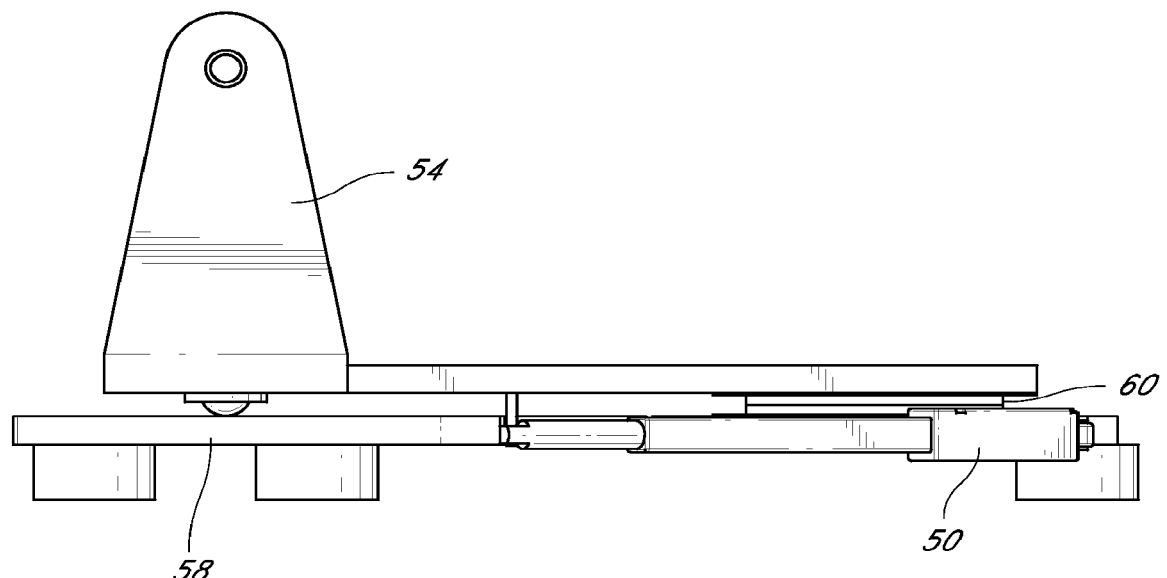
FIG. 5 shows portions of a ball delivery device.

Moving the actuator 50 illustrated in FIGS. 4 and 5 can change the relationship of a portion of the ball delivery device 40 with the opening 20. Thus, the ball delivery device can pitch the ball out the opening within a range of angles from the straight on position. For example, the ball delivery device can pitch the ball within +10% or +20% (or some other angle) of the straight-on position.

It will be understood that the ball delivery device 40 can function in many different ways, including ways different from those described herein. For example, rather than including an actuator, the ball delivery device 40 can be moved or positioned with one or more stepper motors connected directly between two rotating brackets. Further, although described as being primarily used for pitching soccer balls, the ball delivery device 40 can also be adapted to pitch other types of balls, such as baseballs, softballs, tennis balls, racquet balls, squash balls, cricket balls, lacrosse balls, volleyballs, and the like.

III. Example Training and Computing Environments

Figure 6:
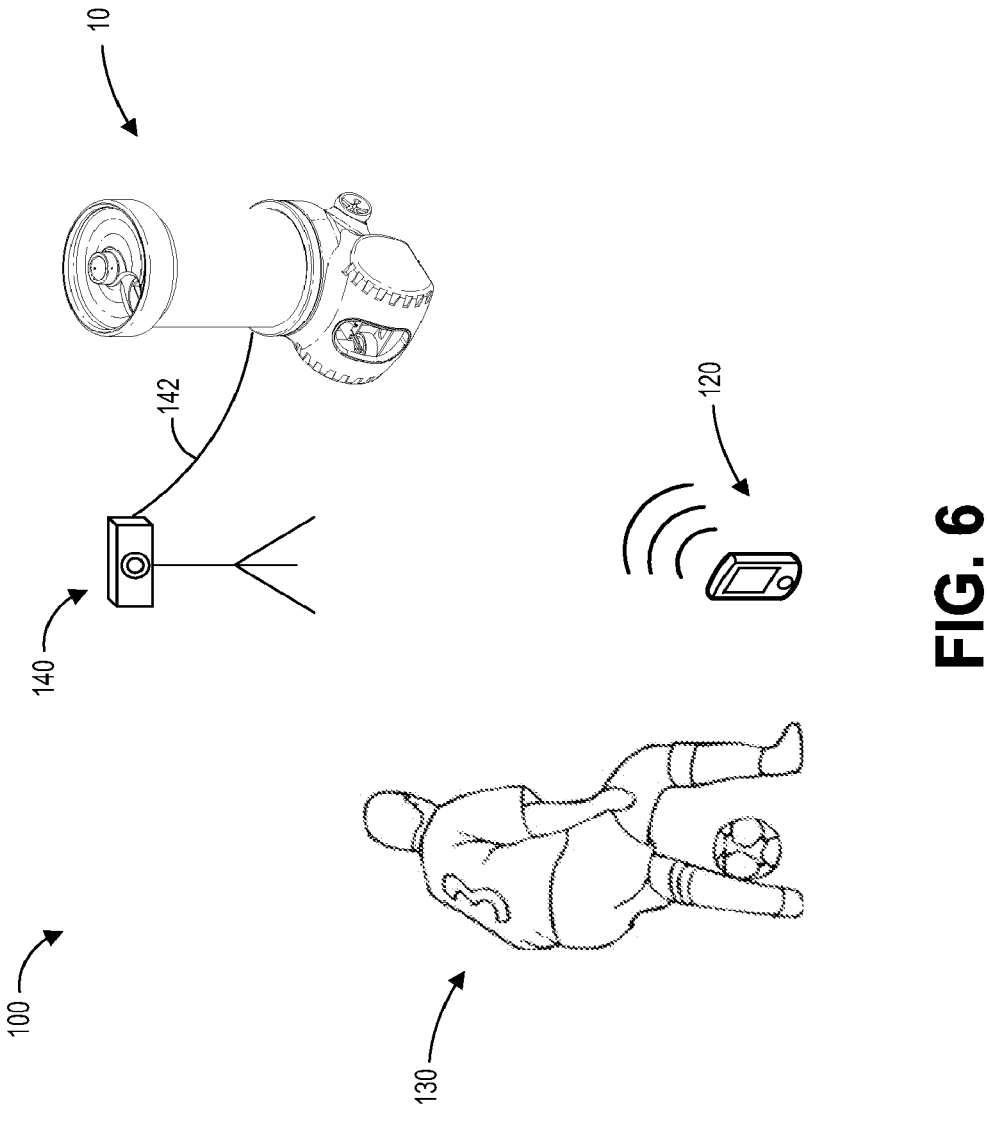
FIG. 6 illustrates an example training scenario using the ball-throwing machine in conjunction with a controller.

FIG. 6 illustrates an example training scenario 100 for using the ball throwing machine 10 in conjunction with a controller 120. In the training scenario 100, a player 130 is training trapping or other ball control skills with the ball throwing machine 10. The player 130 may be any age or gender, and the ball throwing machine 10 can include settings that are appropriate for children, youth, and adults.

A controller 120 is also shown and is in wireless communication with the ball throwing machine 10. The controller 120 can be a computing device of the player 130 (or the player's coach or parent), and may be, for example, a smart phone, tablet, laptop, personal digital assistant (PDA), or other wireless handheld device, or even a desktop in some embodiments. The controller 120 can communicate wirelessly with a wireless module in the ball throwing machine 10 (e.g., in the control unit 46). Alternatively, the controller 120 can be coupled with the ball throwing machine 10 using a cable or a docking station installed in the ball throwing machine 10.

The controller 120 can include functionality for controlling the training programs that run on the ball throwing machine 10. For example, the controller 120 can include functionality for a user thereof, such as the player 130, coach, or a parent, to select training programs to be communicated to the ball throwing machine 10. Each training program can include a set of drills, commands, or instructions to be executed by the ball throwing machine 10, such as how many balls to throw in a given period of time, how fast, and with what trajectory. The training programs can be selected and customized by the player 130, a coach, or a parent.

An optional camera 140 is shown in communication with the ball throwing machine 10 via a cable 142. The camera 140 can take pictures or video of the player 130 during training sessions. The camera 140 can transmit the pictures and/or video to the ball throwing machine 10 over the cable 142 (or a wireless link). In turn, the ball throwing machine 10 can provide the pictures and/or video to the controller 120 wirelessly. Alternatively, the camera 140 can communicate directly with the controller 120, for example, by wirelessly sending pictures and video to the controller 120. Further, in some embodiments, images or video can be taken of the player 130 using a camera in the controller 120 or a built-in camera in the ball throwing machine 10 (not shown) instead of or in addition to the camera 140. In addition, in some embodiments, the camera 140 can communicate with player recognition software running in a processor or controller of the ball throwing machine 10. This player recognition software can locate a player and cause the ball throwing machine 10 to automatically throw a ball to the player. The player recognition software can include facial recognition software but may also detect a player from features of the player other than the face.

Advantageously, in some embodiments, the player 130 can use the controller 120 to submit pictures, video, or other player training data to a remote web site or network application (described below with respect to FIG. 7). The web site or network application may provide functionality for a coach to evaluate the player training data and provide feedback, including customized training programs that can be executed by the ball throwing machine 10.

Figure 7:
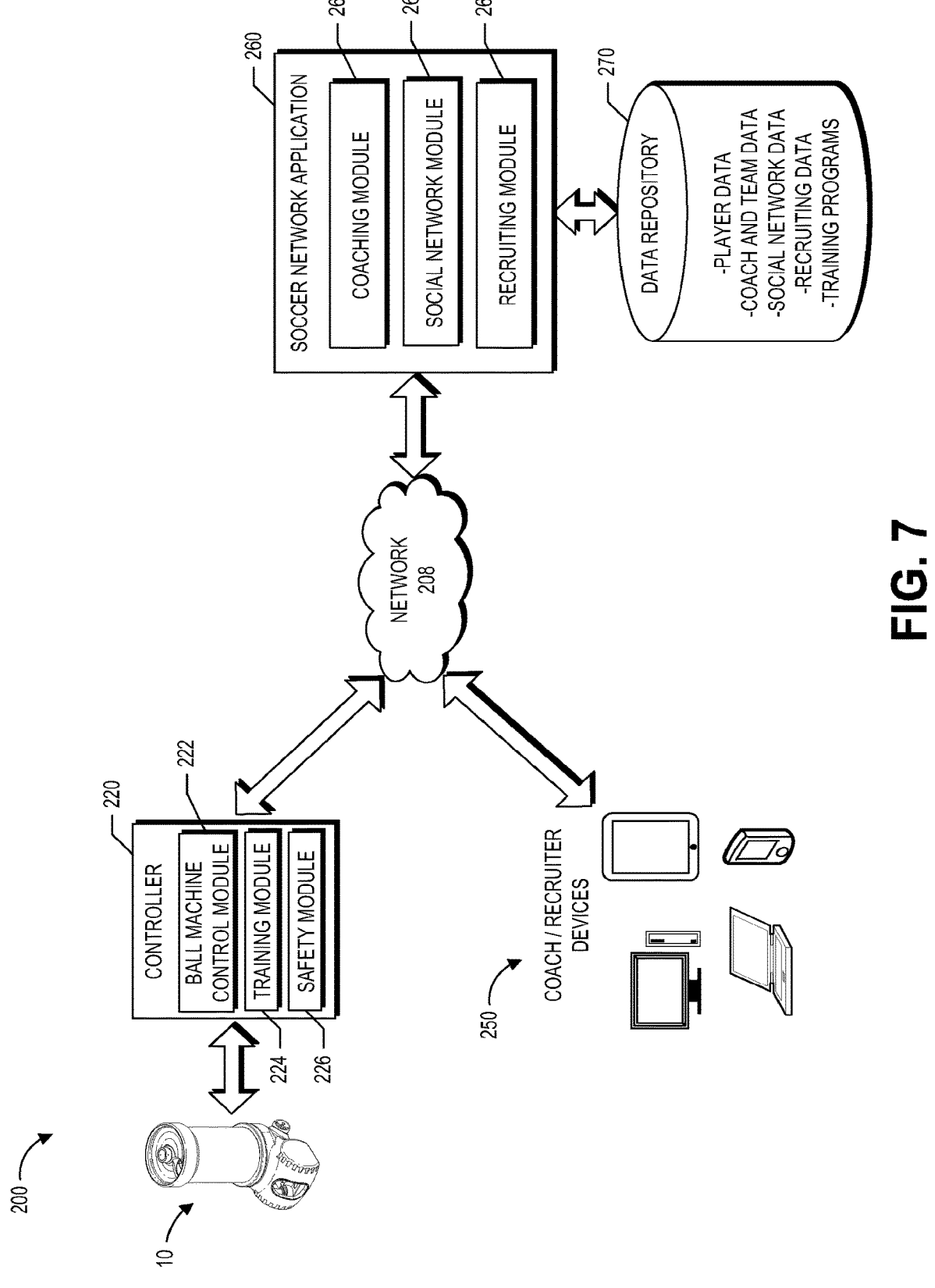
FIG. 7 illustrates an embodiment of a computing environment for facilitating communications between the controller of FIG. 6 and a soccer network application.

FIG. 7 illustrates an embodiment of a computing environment 200 for facilitating communications between the ball throwing machine 10, a controller 220, and a soccer network application 260. Advantageously, in certain embodiments, the computing environment 200 enables players to track player training data regarding training sessions with the ball throwing machine 10 and provide the player training data to a coach via the soccer network application

260. The coach can use the soccer network application 260 to provide feedback to the player, including customized training programs, based on the players' progress with the ball throwing machine 10.

By way of overview, the ball throwing machine 10 communicates with the controller 220, for example, wirelessly using WiFi (IEEE 802.11x), Bluetooth, Zigbee, or any other standard protocol(s). The controller 220 is a more detailed example of the controller 120 of FIG. 6 and can have all the features of the controller 120 described above. The controller 220 can communicate with the soccer network application 260 over a network 208, which may be a LAN, a WAN, the Internet, or combinations of the same. Devices 250 operated by coaches and/or recruiters may also communicate with the soccer network application 260 (or directly with the controller 220 or machine 10) over the network 208.

In the depicted embodiment, the controller 220 includes a ball machine control module 222, a training module 224, and a safety module 226. Each of these components can be implemented with hardware and/or software. In one embodiment, the modules 222, 224, 226 are part of a controller application installed on the controller 220. The controller application may be obtained for installation on the controller 220 from an application store (such as the iTunes™ application store or Android™ Market application store), via computer-readable media (such as a USB key or DVD), or the like. In some embodiments, the controller 220 is sold or otherwise provided together with the ball throwing machine 10 with the controller application preinstalled. Other functionality may also be provided with the controller 220 in some implementations.

The ball machine control module 222 of the controller 220 can provide functionality for a user (such as a player, coach, or parent etc.) to control the ball machine 10. For instance, the ball machine control module 222 can output a user interface that provides options for a user to select different types of training programs or individual ball throwing characteristics to be implemented by the ball throwing machine 10. This user interface can be implemented on a touch screen display of the controller 220 in some devices, although other types of controller 220 displays may also be used. In response to receiving user input regarding a desired training program or throwing pattern, the ball machine control module 222 can send instructions or commands to the ball throwing machine 10. A processor or other circuitry in the ball throwing machine 10 (such as the control unit 46) can receive and execute these instructions. The ball machine control module 222 can therefore enable a user to control any functions of the ball throwing machine 10, including but not limited to ball velocity, ball delivery (e.g., air, ground, line, lob, or bounce), ball trajectory (e.g., angled, curved, or straight), ball oscillation (e.g., side-to-side or middle-to-side), ball throwing frequency (e.g., every user-specified number of seconds), and the like.

The training module 224 can provide functionality for a user to record data regarding the player's usage of the ball throwing machine 10. For example, the training module 224 may provide a training user interface that enables a user to record this player training data (see, e.g., FIG. 13). This player training data can include a log of the commands sent to the machine 10, the commands executed by the machine 10, the user's success with traps or goals or other ball-control drills, video data, and the like. In one example implementation, the training module 224 provides user interface controls (such as touch-screen controls) that enable a user to input whether a trap is successful. The training module 224 may also include voice recognition functionality, using any commercially available voice recognition software. A user can therefore dictate verbal training results to the training module 224, such as "successful trap" or "missed trap," or simply just "success" or "miss," or the like. The training module 224 can interpret the voice commands and record the interpretation (e.g., a success or miss) in the player training data. The training module 224 can supply the player training data to the soccer network application 260 (described below) over the network 208.

The safety module 226 can provide a user interface that enables users to manage safe use of the ball throwing machine 10. For instance, the safety module 226 can provide parental controls or the like that enable a parent, coach, or other responsible person to manage access to the ball throwing machine 10 or features thereof. It can be desirable to have such features to prevent accidents that can occur, for example, from setting the ball velocity or throwing frequency too high for younger players. These parental controls can include an authentication mechanism (such as a username/password or other credential) for enabling access to the machine 10, control over ball-throwing parameters such as velocity, and an idle or timeout feature that can shut down the controller 220 and/or ball throwing machine 10 after a timeout period of inactivity (such as 30 seconds, a minute, or some other time). Any of these safety features can also be implemented directly in the electronics of the ball throwing machine 10, rather than in the controller 220.

The soccer network application 260 can store player training data received from the training module 224 in a data repository 270. The data repository 270 can include any form of physical computer data storage, as well as logical computer storage. For instance, the data repository 270 can include one or more databases, associated physical storage media, and the like. The soccer network application 260 can include hardware and/or software for providing players (via the controllers 220 or other devices), coaches, and recruiters with access to the player training data, among optionally other data and features. The soccer network application 260 includes, in the depicted embodiment, a coaching module 262, a social network module 264, and a recruiting module 266. These modules represent at least some of the functionality that the soccer network application 260 may provide to players, coaches, recruiters, and others.

Each of the modules 262, 264, 266 can provide user interfaces for users to access features of the modules 262, 264, 266. For instance, the coaching module 262 can provide one or more user interfaces that enable a coach to access and analyze player training data for a plurality of players associated with that coach. If the player training data includes video, for instance, the coaching module 262 can provide functionality for the coach to view videos of players. The coaching module 262 can also provide functionality through one or more user interfaces for a coach to provide feedback to players. This feedback may be in the form of textual feedback, video feedback, or training program feedback. A coach may, for instance, respond to the uploading of a player's training data with comments on the player's form and suggest adjustments to the player's training program. Beneficially, in some embodiments, the coaching module 262 also enables a coach to select or create a training program to provide to a player as homework or the like. The coaching module 262 may provide a user interface for creating a custom training program for a specific player (see FIG. 16).

Moreover, the coaching module 262 can enable a coach to better leverage his or her time when training players. In the past, a coach has typically spent a few hours per week with an entire team of players, and the coach's ability to provide individual attention to those players has been limited. Further, a coach is typically not present when a player is practicing at home or with friends. However, with the soccer network application 260, a coach can evaluate player training data for several players and provide individualized feedback and training program recommendations to those players, without leaving his or her home. Thus, the soccer network application 260 can enable coaches to focus more individual attention on the development of players' ball control and trapping skills.

The social networking module 264 can provide functionality for different players, coaches, and the like to interact together in an online soccer community. For example, the social networking module 264 can provide user interfaces for creating player or coach pages, discussing soccer training with teammates and friends, uploading pictures and video, linking to web sites regarding soccer or other topics, and other features that may be found in any social network. Generally, the social network provided by the social networking module 264 can enable users to keep track of each other's progress in training with the ball throwing machine 10 and encourage each other in their progress. The social network module 264 may also provide an event user interface that enables users to coordinate events, such as impromptu soccer games, among other features.

The recruiting module 266 can provide a recruiting user interface that enables recruiters to examine player data and/or for players or coaches to upload player data to recruiters. Some examples of recruiters that can use such features include high school recruiters, college recruiters, and professional recruiters. In one embodiment, the recruiting user interface enables recruiters to view player training data obtained with respect to the ball throwing machine 10. Advantageously, in certain embodiments, player training data obtained in conjunction with the ball throwing machine 10 can provide a standardized approach to reviewing player performance. Other player data may also be stored in the data repository 270 and made available to recruiters via the recruiting user interfaces, such as in-game data, coach reviews, scout reports, and the like.

It should be noted that the soccer network application 260 can be implemented as one or more physical servers. These servers may be geographically dispersed or co-located. In addition, in some embodiments, the soccer network application 260 is implemented as a cloud-computing platform. For example, the soccer network application 260 can be implemented as one of a plurality of virtual machines executing on a hypervisor, which can be a thin layer of software executing on a physical machine. Accordingly, the modules 262, 264, 266 of the soccer network application 260 can be implemented in hardware and/or software.

Further, it should be noted that although the features of FIGS. 6 and 7 as well as the features in subsequent FIGURES can be implemented in conjunction with the ball throwing machine 10, other ball throwing machines than the one explicitly described may also be used. For example, a throwing machine designed for a different sport can be controlled by the controller 120 or 220, or a different soccer-ball throwing machine can be used with the controller 120 or 220.

IV. Example Training Processes

FIG. 8 illustrates an embodiment of a ball machine control process 300 that may be implemented by the controller 220

(or 120). The ball machine control process 300 can enable a player to run customized training programs on a ball throwing machine, such as the ball throwing machine 10. Advantageously, these customized training programs can be designed by a remote coach who creates or selects the programs based on the player's progress with the ball throwing machine.

The process 300 begins at block 302, where the ball machine control module 222 of the controller 220 establishes communication with a ball throwing device. The ball machine control module 222 can establish communication in one embodiment according to a wireless or other network protocol. At block 304, the ball machine control module 222 causes the ball throwing machine to perform an initial training program. The performance of this initial training program is described in more detail below with respect to FIG. 9. As an overview, however, the initial training program can include one or more drills, which may include user-defined ball throwing commands or stored ball-throwing commands (which may have been stored by the player or coach).

At block 306, the training module 224 of the controller 220 records playing training data. There are many ways that this training data may be recorded, and many possible forms that the training data may take. Player training data can be recorded by the training module 224 automatically in one embodiment. For example, the training module 224 can log the commands issued by the controller 220 to the ball throwing machine, or may log the commands actually executed by the machine. For instance, the machine can report to the controller 220 which commands executed successfully and which did not execute successfully. Successful execution of a command can mean, in one embodiment, that the ball throwing machine performed a throw. The amount of data that the training module 224 collects regarding issued or executed commands can vary as well. This data can include characteristics of a throw, such as the ball's velocity (or desired velocity), delivery (or desired delivery), trajectory (or desired trajectory), oscillation (or desired oscillation), and/or frequency (or desired frequency). Any subset of this information may be collected and stored by the training module 224 in computer storage. Alternatively, the training module 224 merely records that a throw command was issued or occurred. In yet another implementation, the training module 224 records the target area or target zone on the player's body that the throw is aimed at (see FIG. 12).

As described above, the training module 224 may provide a user interface or voice recognition that enables a user to record whether a trap was successful. The player training data may include this success/lack of success information in addition to, or instead of, the more detailed throw or ball characteristics described above. In some embodiments, the training module 224 obtains an electronic indication of whether a player successfully trapped a ball or at least came in contact with the ball. This electronic indication can come from one or more sensors embedded in or placed on a players' clothing. Sensors can be placed or embedded anywhere on or in a player's clothing or on a player's person. Some example areas where sensors may be placed include the chest area, legs, thighs, feet, on the player's head, or any other location on the player's clothing or body. The sensors can be pressure sensors, contact sensors, or any other form of sensor that can produce an electronic output responsive to contact with a ball. For example, a player's shoe may have sensors embedded in one or more surfaces of the shoe to track whether the ball came into contact with such surfaces. Further, in some implementations sensors may be placed in a goal net (and/or on the posts) to determine whether the player has shot a ball in the goal. The sensors may communicate wirelessly with the controller 220 and/or ball throwing machine to provide sensor data to the training module 224. The training module 224 can incorporate the raw sensor data or processed versions thereof into the player training data. Accordingly, the player training data can include automatic indications of whether a trap was successful, or at least whether the ball came into contact with a player. One or more sensors can also be embedded in any of the balls described herein to track trapping, shooting, and other soccer skills.

The player training data may also include video data as described above. Further, the training module 224 can record any subset of the training data described herein. At block 308, the training module 224 submits the player training data to the soccer network application 260 with a request for feedback from a coach. This request for feedback may be explicit or implicit. For instance, a player can access a feature of the training module 224 that enables submission of player training data to the soccer network application 260. The soccer network application 260 may in turn make this player training data available to a coach of the player, or to a pool of coaches from which one is assigned or who picks the player training data for analysis. In another example scenario, the player can explicitly request the feedback of a particular coach when submitting the player training data to the soccer network application 260.

At block 310, the training module 224 receives a customized training program from the coach through the soccer network application 260. The customized training program can have any characteristics of any of the training programs herein. In one embodiment, the customized training program received includes a set of commands that the ball machine control module 222 can transmit to the ball control machine. In another embodiment, the coach can provide textual, verbal, or video instructions to the player regarding how to customize the player's training. The coach may also provide both an actual training program (including drills or machine commands) and textual, verbal, and/or video feedback. It should be understood, however, that the coach may not actually provide machine-level commands to the controller 220 (although this can be done in some embodiments). Rather, the soccer network application 260 can provide one or more user interfaces that enable a coach to select or define a training program having one or more drills. In response to that selection or definition, the soccer network application 260 can generate the appropriate commands that can be executed on the ball throwing machine.

At block 312, the ball machine control module 222 causes the ball throwing device to perform the customized training program. Thus, the ball machine control process 300 can enable a player to receive individualized attention from a remote coach on ball trapping skills or other soccer skills.

Figure 9:
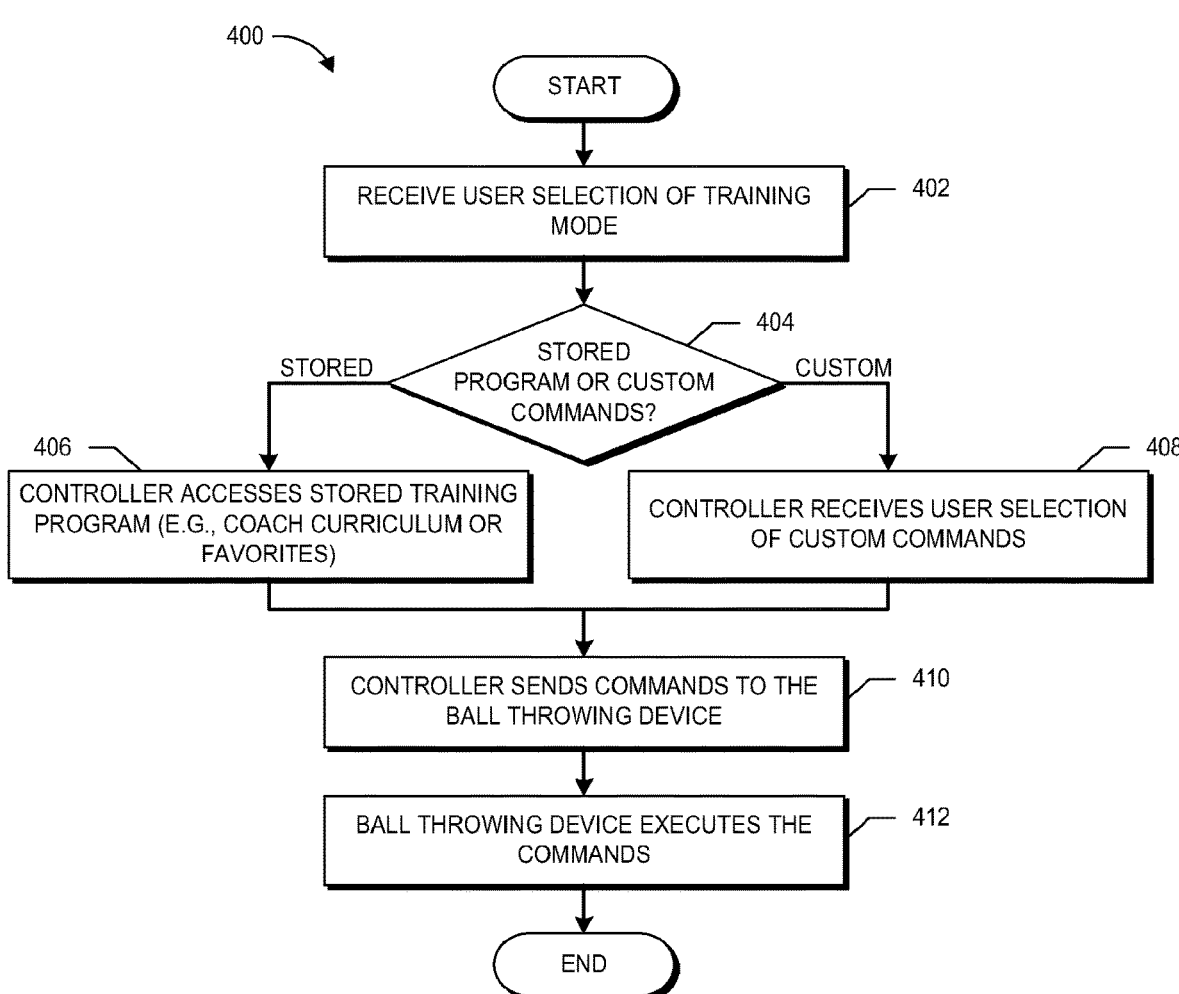
FIG. 9 illustrates an embodiment of a training process that may be implemented using the ball throwing machine and the controller of FIG. 6.

FIG. 9 illustrates an embodiment of a training process 400 that may be implemented using the ball throwing machine 10 and the controller 120 or 220. The training process 400 is a more detailed example implementation of the initial training program block 304 described above with respect to FIG. 8. The training process 400 may be implemented, for example, by the ball machine control module 222 of the controller 220.

At block 402, the ball machine control module 222 receives a user selection of training mode. A variety of training modes may be provided. These training modes may include, for example, the ability to access a stored program (or a program over a network), and the ability to perform custom training. This custom training can be a "free-play" type of training, where a user can define each ball's throwing characteristics as they are thrown. Although not shown, a random play mode is also available in some implementations, enabling a user to select a random series of throws having random characteristics (such as random velocity, angle, trajectory, and so forth). The custom training can also involve the user creating his or her own training program, which the user may subsequently store in memory of the controller 220 or ball throwing machine. The controller 220 may also provide functionality (such as a user interface or user interface control) for users to uploads custom training programs created with the controller 220 to the soccer network application 260, where other players or coaches can download the custom training programs. Further, the soccer network application 260 can provide user interface options to comment on and/or rate custom training programs, thereby enabling users to better decide which custom training programs to download.

At decision block 402, the ball machine control module 222 determines whether the user selection is for a stored program or custom commands. If the selection was for a stored program, the ball machine control module 222 accesses the stored program at block 406. The stored program may be a program created by the user and saved as a "favorite" program or the like. Alternatively, the stored program can be a training program provided by a coach. If the user selection was for a custom program, the ball machine control module 222 receives a user selection of custom commands at block 408. The ball machine control module 222 of the controller 220 sends the commands to the ball throwing device at block 410, which executes the commands at block 412.

FIG. 10 illustrates an embodiment of a coaching process 500 that may be implemented at least in part by the soccer network application 260. In particular, the coaching process 500 can be implemented at least in part by the coaching module 262. The coaching process 500 can advantageously enable a coach to leverage his or her time to customize training for multiple players without having to be physically present with each of those players.

At block 502, the coaching module 262 receives player training data from a plurality of controllers of ball throwing machines, such as any of the controllers or machines described above. At block 504, the coaching module 262 electronically generates a remote coaching interface having options for selecting or defining training programs (see FIG. 16, described below). For each player, at block 506 the coaching module receives a coach selection of a customized training program based on the player training data for that player. In one embodiment, the coach selects or creates the training program. In another embodiment, the soccer network application 260 recommends the training program based on an automated analysis of the player training data. For example, the network application 260 can recommend a training program that is automatically customized to a player based on any of the following: previous drills performed by the player, age of the player, skill level of the player, a player's position, a past or recommended heart rate target for the player, combinations of the same, or the like. At block 508, the coaching module 262 provides data representing the customized training program for each player to the player's controller.

V. Example User Interfaces

Figure 14:
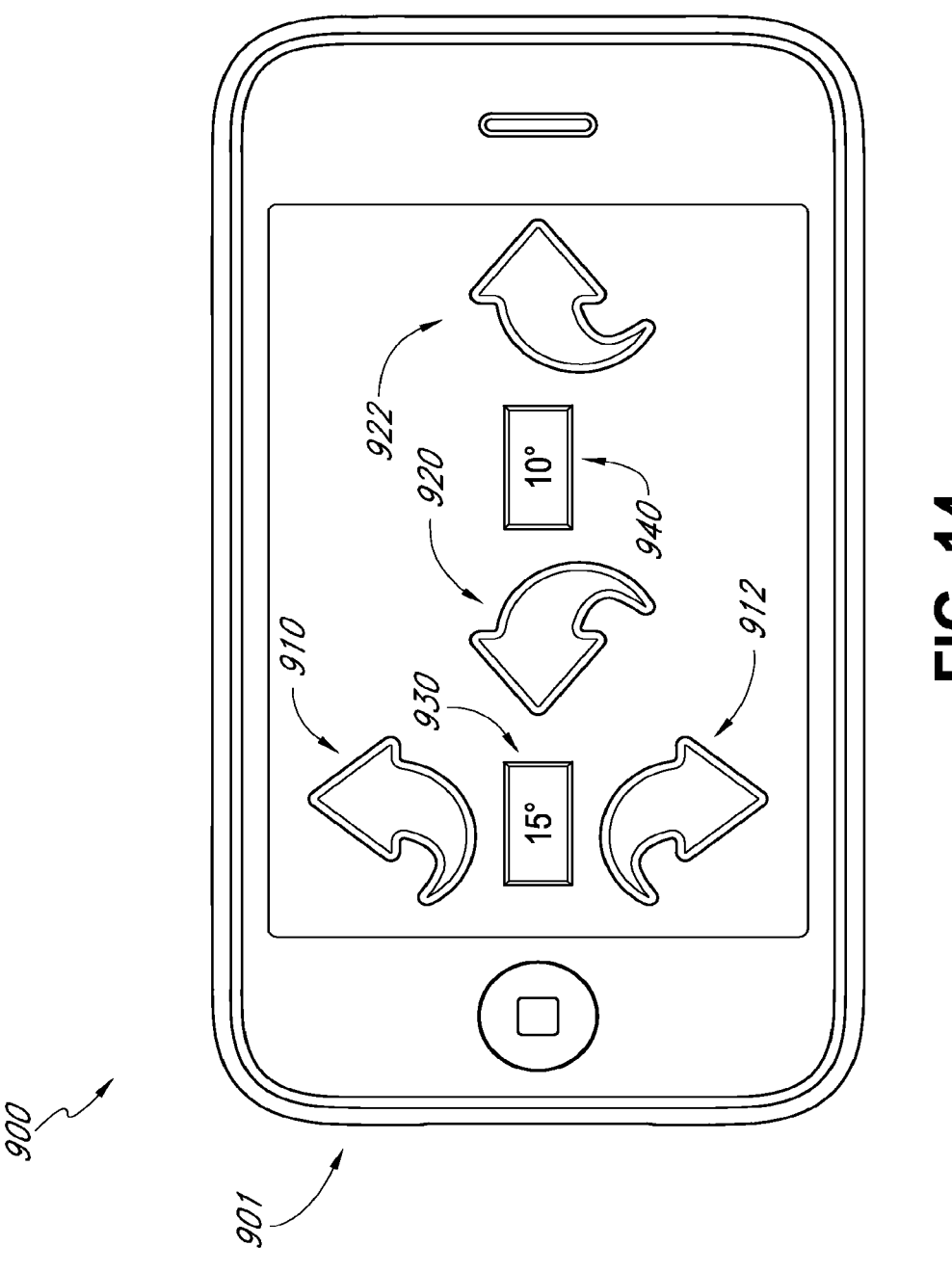
Figure 15:
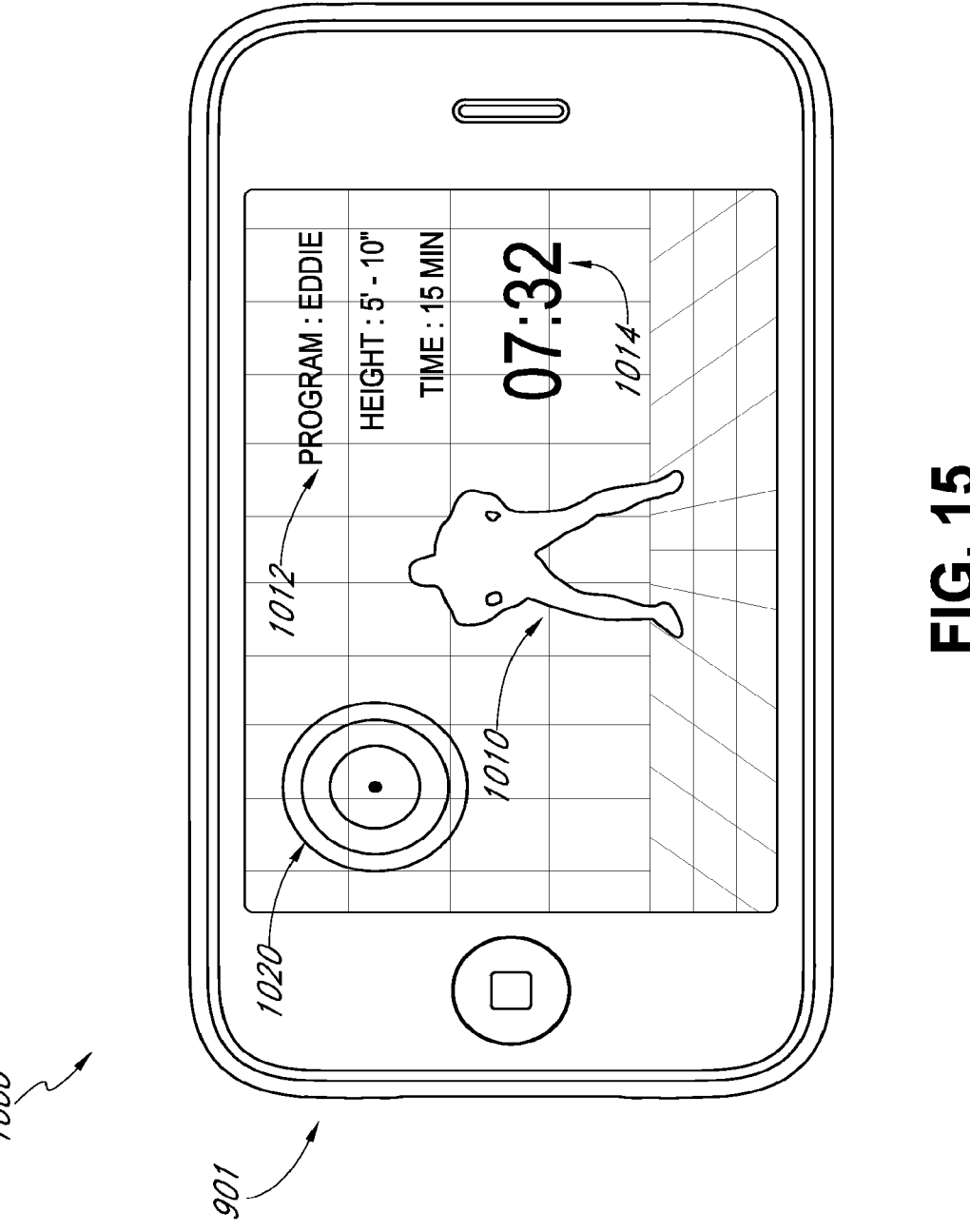
Figure 16:
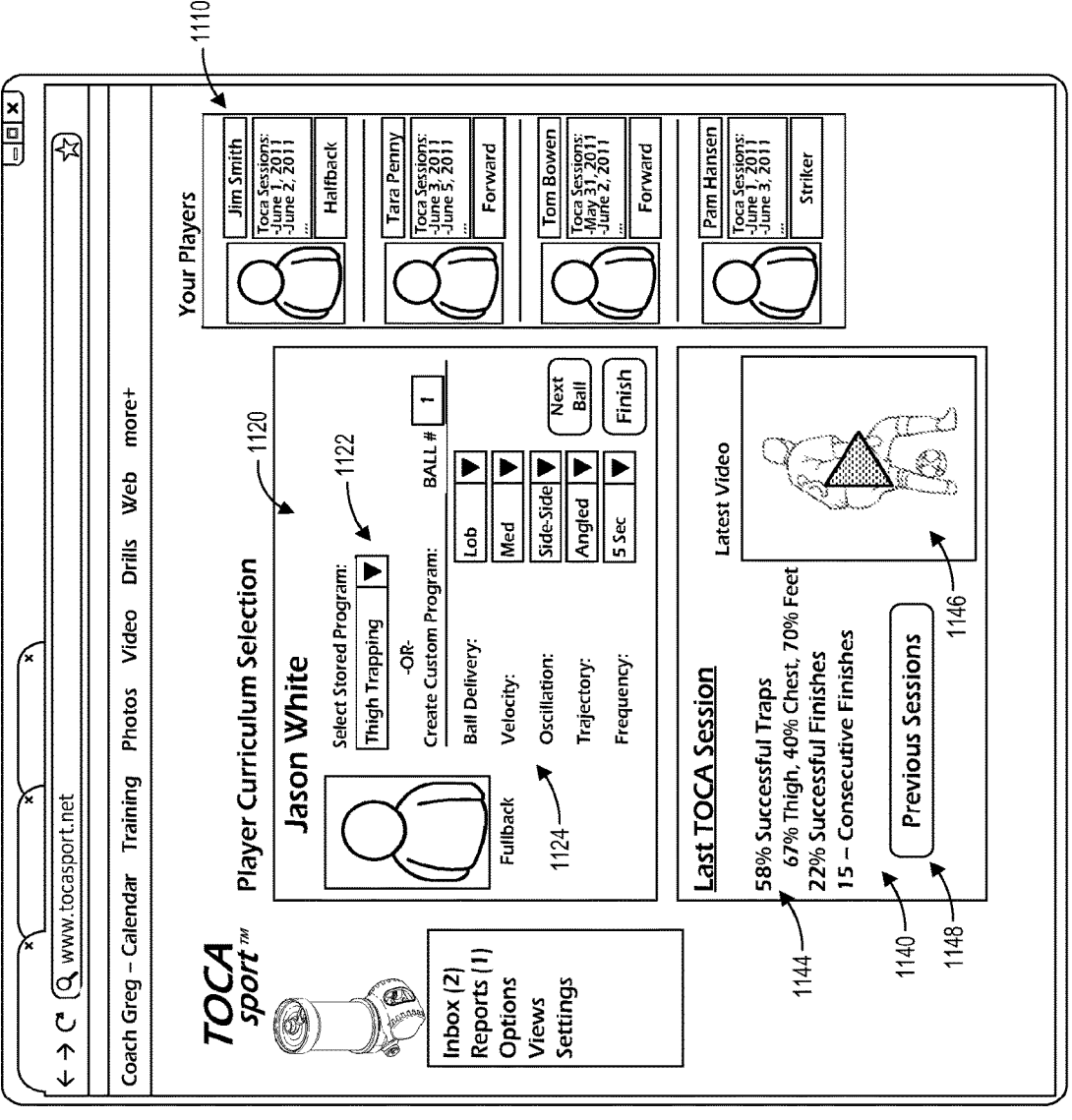
FIGS. 16 and 17 illustrate embodiments of user interfaces that may be generated by the soccer network application of FIG. 7.
Figure 17:
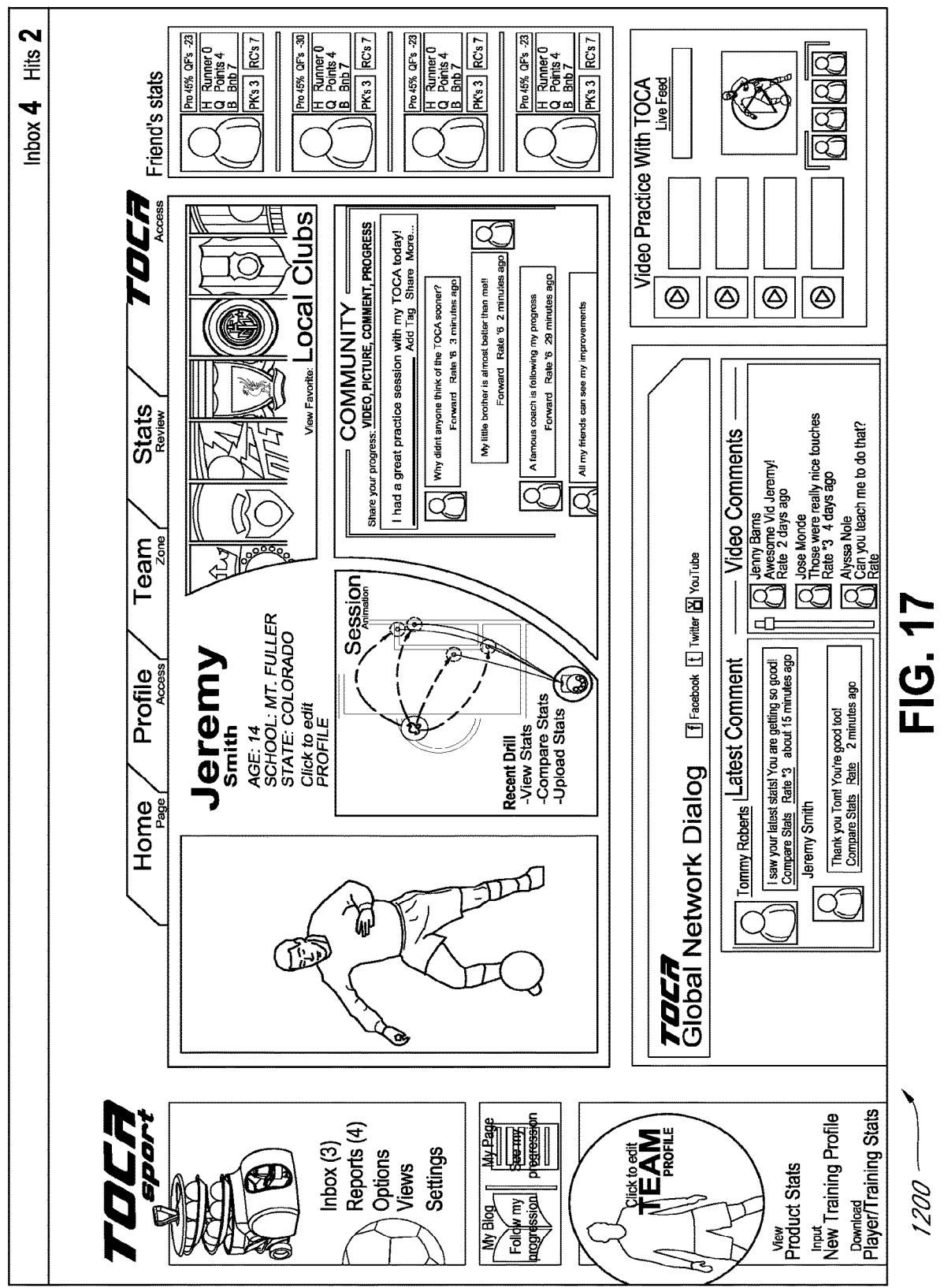

FIGS. 11 through 17 illustrate embodiments of controller user interfaces 600-1200 that may be generated by the controller 120 or 220. Each of these user interfaces 600-1200 may be generated by an application on a handheld computing device, such as a tablet or smartphone. In addition, the user interfaces 600-1200 may also be generated on another computing device, such as a laptop or desktop, as part of a web page rendered by a browser or by other software. In the example embodiments shown, FIGS. 11 through 15 illustrate example aspects of a controller application, while FIGS. 16 and 17 illustrate example aspects of a soccer network application.

Figure 11:
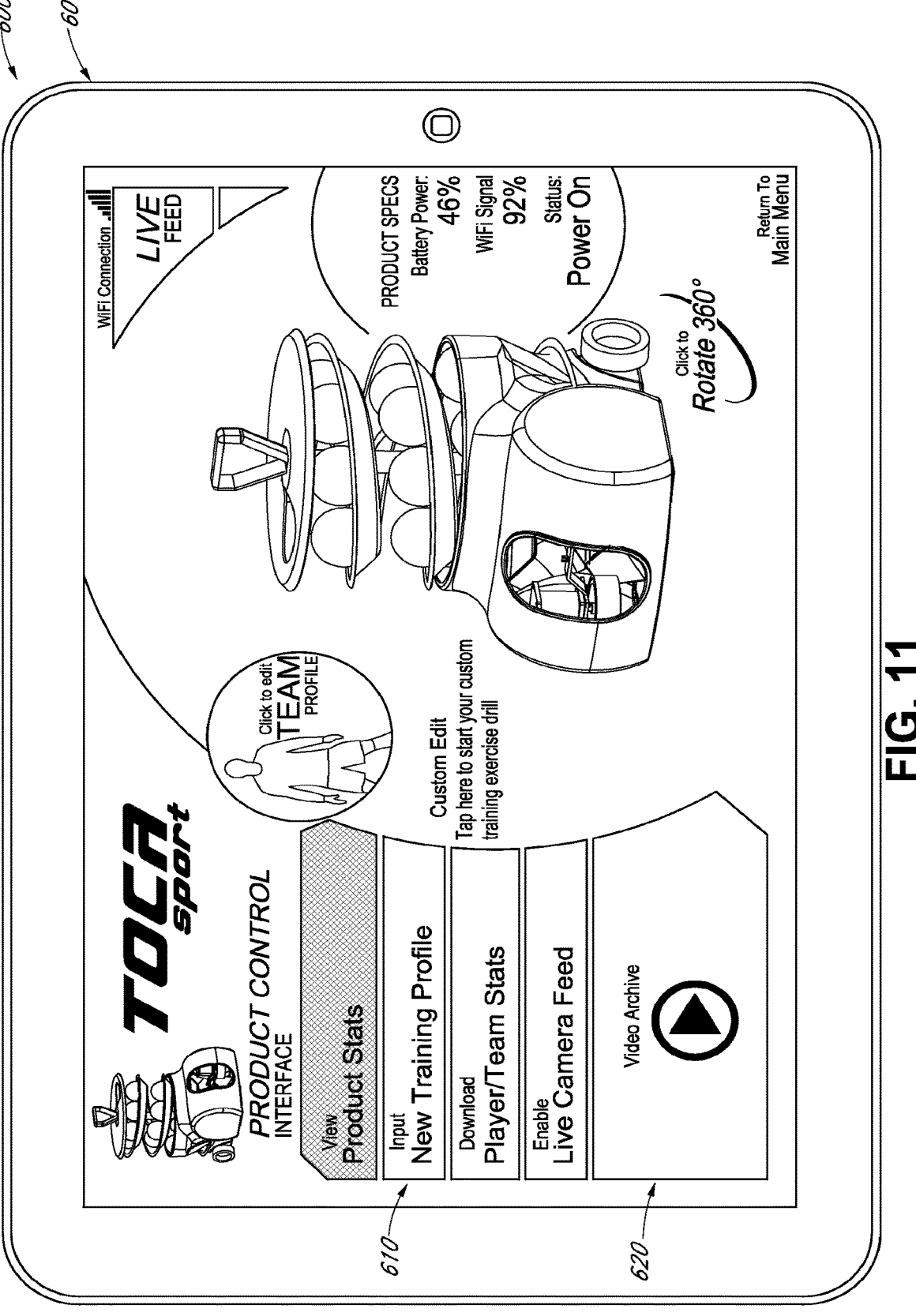
FIGS. 11 through 15 illustrate embodiments of controller user interfaces that may be generated by the controller of FIG. 6.

Referring specifically to FIG. 11, a controller user interface 600 is shown on a tablet device 601 for illustrative purposes, although other devices may be used to render the controller user interface 600. The controller user interface 600 includes controls 610 for accessing various options and may be generated by the ball machine control module 222. Example options shown include options to view product (ball machine) stats, create a new training profile to begin training, download player or team stats (from the soccer network application), and enabling a live camera feed. An addition control 620 is provided for viewing stored videos. These videos can be videos of the player, training videos on how to use the machine, or tutorials on how to improve soccer skills, to name a few.

Figure 12:
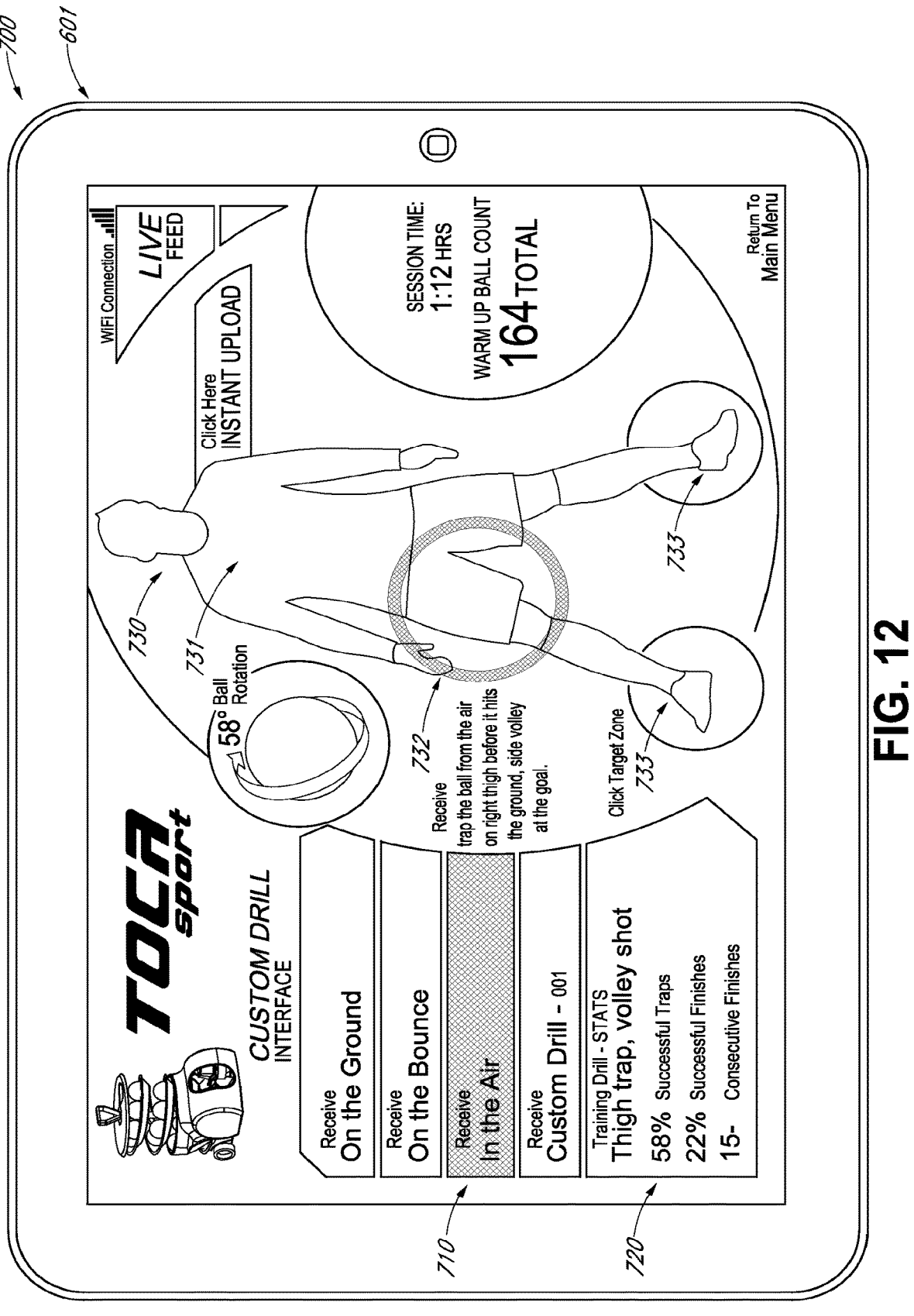

FIG. 12 illustrates another controller user interface 700, shown on the example tablet device 601 for illustrative purposes. The user interface 700 may be generated by the ball machine control module 222. The controller user interface 700 includes controls 710 for controlling various ball-delivery options, which enable a user to select whether to receive a ball on the ground, on the bounce, or in the air, or some other custom setting. Statistics 720 regarding the player's training drills are also shown, which indicate that for thigh traps, the player has made 58% successful traps, 22% successful finishes (e.g., shots on goal after trapping the ball), and 15 consecutive finishes. A graphic 730 illustrates a part of the player's body on which the ball should be trapped for a particular drill. In the embodiment shown, the graphic 730 highlights the player's thigh as the target zone 732 to which the ball will be thrown and trapped. In one embodiment, the user may select a target zone 731, 732, or 733 on the graphic 730 (using a finger, mouse, or the other input mechanism) to cause balls to be thrown to a different area of the player's body. For example, selection of a foot target zone 733 can cause the ball throwing machine to throw balls toward the player's feet.

More particularly, in one embodiment, selection of a foot target zone can cause the machine to throw a ball along the ground or lob the ball toward the player's feet. The distance or approximate distance of the player to the machine may be input by a user into the controller 220 to thereby enable the machine to make such a lob. Similarly, selection of a thigh or chest target zone can cause the controller 220 can cause the machine to lob, bounce, or line drive the ball to a player's thigh or chest. The controller 220 may also provide functionality for other target zones to be selected, such as the head or the hands (for goalies). For example, the controller 220 can enable a player to select a spot away from the player where the player is to dive and catch the ball with his or her hands.

Figure 13:
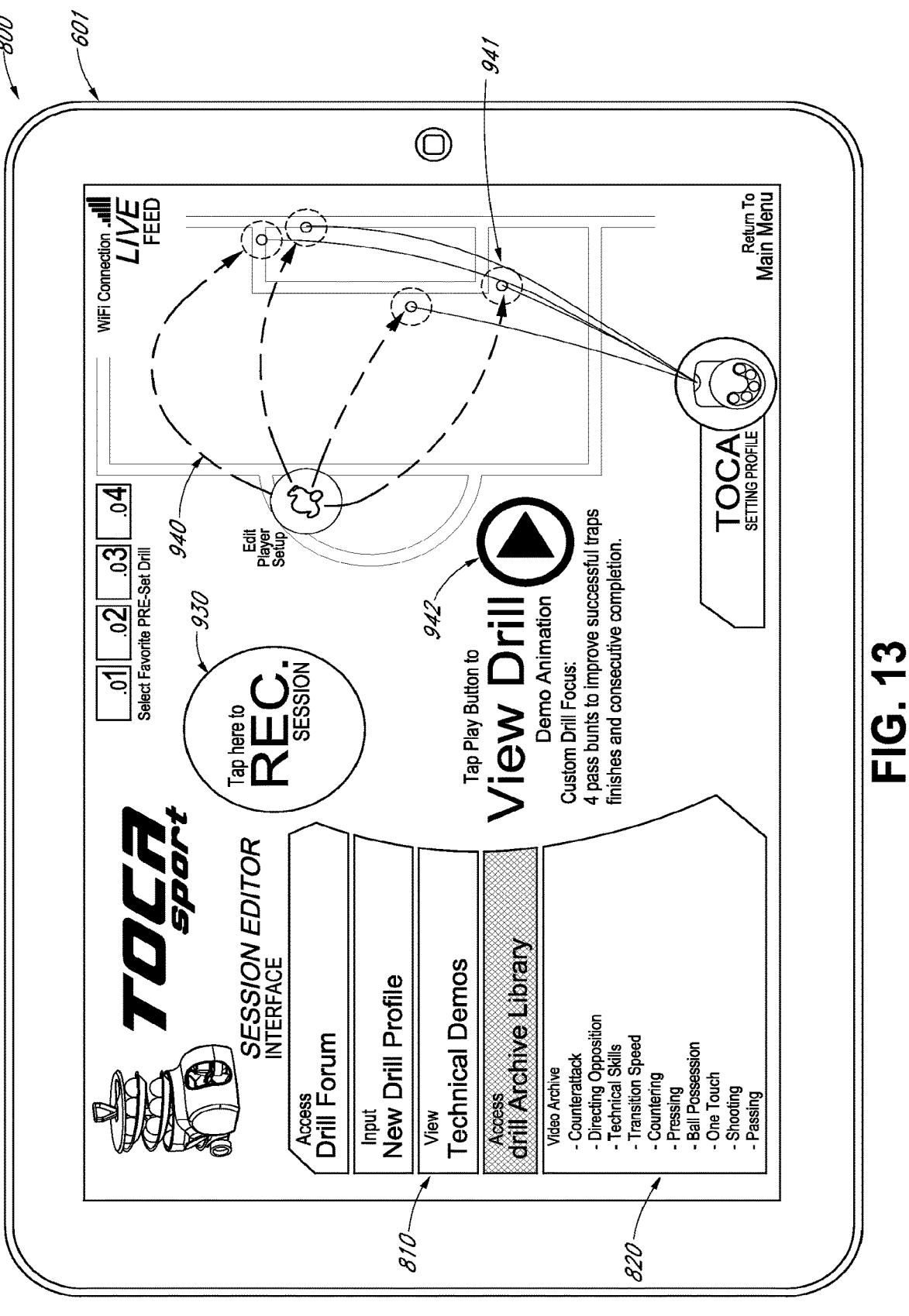

In FIG. 13, another controller user interface 800 is shown, also illustrated on the table device 601. The controller user interface 800 includes controls for a user to edit a training session by accessing a drill forum, inputting a new drill profile, viewing technical demos, or accessing a drill training library from which to select new drills. The drill forum can allow players to share drills and training ideas and can be implemented in a web site or other network application. Another control 820 is provided for accessing a video archive of drills. The user may record a training session using any of the recording techniques described above by selecting a record control 930. The record control 930 is an example of a control that may be provided by the training module 224 to record player training data. A specific selected drill 940 is also shown, which includes a series of projected ball trajectories 941. A demo control 942 is provided to enable a user to view a demo animation (or video) of how the drill 940 is to be performed.

FIGS. 14 and 15 illustrate additional example controller user interfaces 900, 1000 implemented in the context of a smartphone 901. It should be understood, however, that the user interfaces 900, 1000 may be implemented in other devices. Likewise, the other user interfaces described herein may be implemented on a smart phone. In FIG. 14, the user interface 900 includes arrow controls 910, 912, 920, 922 and angle controls 930, 940 to select a ball to be thrown in a specific direction. For example, selection of the up control 910 or down control 912 at an angle 930 of 15 degrees can cause the ball to be thrown up or down at an angle of 15 degrees from a horizontal plane (e.g., the ground). Similarly, selection of the left control 920 or right control 922 at an angle 940 of 10 degrees can cause the ball to be thrown left or right at an angle of 10 degrees from the vertical plane (e.g., perpendicular to the ground and intersecting the machine and the player). Multiple ones of the controls may be selected for any given throw. For instance, the up arrow 910 and the left arrow 920 may be selected simultaneously to cause a ball to be thrown to the upper left of the player at specified angles 930, 940.

In FIG. 15, the controller user interface 1000 includes a target zone 1020 that can be selected by a user, to which the ball machine will attempt to throw a ball. This target zone 1020 is shown relative to a graphic image of a player 1010. Thus, in the depicted embodiment, the target zone 1020 is to the right of the player's 1010 head, enabling the player to practice heading the ball. Statistics 1012 regarding the player, such as the player's name, height, and the time of the training program are shown as illustrative example statistics. Similarly, the time remaining 1014 in the program is also shown.

Referring to FIG. 16, an example coaching user interface 1100 is depicted as being in a web browser. A coach may access the coaching user interface via a web browser or other application software. The coaching user interface 1100 includes selectable controls 1110 that represent the coach's players, which include information such as their names, positions, their player training data, and so forth. Coach-selection of one of the player controls 1110 can cause a curriculum selection display 1120 to be produced on the user interface 1100 as well as player training data 1140 for a particular player. In an alternative embodiment, the user interface 1100 can enable the coach to create training programs without first selecting a player. The coach can save such training programs for subsequent selection by a player. Further, in some embodiments, the user interface 1100 may be used by a player to create a custom training program or modify another user's custom training program online. The player can then use the user interface 1100 to send the custom training program to a controller (220).

The example player training data 1140 shown includes data regarding the most recent session the player had with the ball throwing machine. This data includes trap completion data 1144 and video 1146. A button link 1148 to previous sessions is also provided. The curriculum selection display 1120 includes various controls 1122, 1124 that enable a coach to define a training program. These controls include a selection control 1122 for selecting a stored (e.g., previously created) program and creation controls 1124 for creating a custom program. Some example parameters for creating a custom program are depicted with respect to the controls 1124, enabling a coach to define for each ball in a program its various characteristics (such as ball delivery type, velocity, oscillation, etc.). These characteristics are merely examples. In other embodiments, for instance, the coaching user interface 1100 may provide functionality for a coach to input the types of target zones each ball is directed to, such as the thigh, chest, foot, etc., in addition to or instead of the characteristics shown.

FIG. 17 illustrates an example social networking user interface 1200 that may be generated by the soccer network application 260. The social networking user interface 1200 includes profile information for a player, community features for discussing training progress, videos, and other related social networking features. For example, some potential features of the social networking user interface 1200 or other such user interfaces can include, among others, depicting of results of training or games, providing of tips and training advice, biogs, videos, player ratings, player rankings (including possibly highlight rankings for ranking impressive video-recorded training sessions), help request functionality for asking an expert or coach for help, comments from a professional, online webinars and training, contests, event organizations, recruiting tips, other recruiting features, general fitness training, and the like.

VI. Additional Embodiments

In certain embodiments, a soccer ball throwing device includes a hopper that can hold a plurality of soccer balls and a ball delivery device that can receive the soccer balls from the hopper. The ball delivery device can include one or more wheels that can impart motion to one of the soccer balls and a frame attached to the one or more wheels. The frame can be positionable to control a trajectory of the ball. The soccer ball throwing device may also include a ball delivery control circuit that can control the position of the frame and the speed of the one or more wheels. Further, the ball throwing device can include a controller in communication with the ball delivery control circuit. The controller can include one or more processors that can at least: cause the soccer ball throwing device to perform an initial training program that includes a set of one or more ball trapping drills, where the controller causes the soccer ball throwing device to pitch one or more of the soccer balls to a player during said one or more ball trapping drills, enabling the player to practice trapping the ball and thereby improve ball control skills; record player training data that includes information regarding training of the player performed during the initial training program; submit the player training data from the controller over a network to a soccer network application along with a request for feedback from a remote coach through the soccer network application; and in response to submission of the training session data, receive a customized training program from the coach via the soccer network application. The customized training program can include one or more second drills to be executed by the soccer ball throwing device.

In various embodiments, a method of controlling a soccer ball throwing device includes providing a soccer ball throwing device having a hopper that can hold a plurality of soccer balls, a ball delivery device that can receive the soccer balls from the hopper, where the ball delivery device has one or more wheels that can impart motion to one of the soccer balls, and a frame attached to the one or more wheels, where the frame is positionable to control a trajectory of the ball, and a ball delivery control circuit that can control the position of the frame and the speed of the one or more wheels. The method can also include communicating with the soccer ball throwing device via a controller including computer hardware. The method may also include causing the soccer ball throwing device, with the controller, to perform an initial training program that comprises a set of one or more ball trapping drills, where the controller causes the soccer ball throwing device to pitch one or more balls to a player during said one or more ball trapping drills, enabling the player to practice trapping the ball and thereby improve ball control skills. Moreover, the method can include recording player training data that includes information regarding training of the player performed during the initial training program, submitting the player training data from the controller over a network to a soccer network application along with a request for feedback from a remote coach through the soccer network application, and in response to said submitting the training session data, receiving a customized training program from the coach via the soccer network application. The customized training program can include one or more second drills to be executed by the soccer ball throwing device. The method can be implemented by one or more physical processors.

A method of controlling a soccer ball throwing device can include, in various embodiments, establishing communication between a soccer ball throwing device and a controller having computer hardware. The method can also include causing the soccer ball throwing device, with the controller, to perform an initial training program that comprises a set of one or more ball trapping drills, where the controller causes the soccer ball throwing device to pitch one or more balls to a player during said one or more ball trapping drills, enabling the player to practice trapping the ball and thereby improve ball control skills. The method can also include recording player training data that includes information regarding training of the player performed during the initial training program. Further, the method can include submitting the player training data from the controller over a network to a soccer network application along with a request for feedback from a remote coach through the soccer network application, and in response to submitting the training session data, receiving a customized training program from the coach via the soccer network application. The customized training program can include one or more second drills to be executed by the soccer ball throwing device. The method can also be implemented by one or more physical processors.

A system for controlling a ball throwing device can include a ball machine control module that can cause a soccer ball throwing device to perform an initial training program that includes a set of one or more ball trapping drills. The ball machine control module causes the soccer ball throwing device to pitch one or more balls to a player during said one or more ball trapping drills in certain embodiments, enabling the player to practice trapping the ball and thereby improve ball control skills. The system can also include a training module implemented in one or more processors. The training module can record player training data that includes information regarding training of the player performed during the initial training program, submit the player training data over a network to a soccer network application along with a request for feedback from a remote coach through the soccer network application, and in response to said submitting the training session data, receive a customized training program from the coach via the soccer network application. The customized training program can include one or more second drills to be executed by the soccer ball throwing device.

In some embodiments, non-transitory physical computer storage is provided that includes instructions stored therein for implementing, in one or more processors, a system for controlling a ball throwing device. The system can include a ball machine control module that can cause a soccer ball throwing device to perform an initial training program that includes a set of one or more ball trapping drills. The ball machine control module can cause the soccer ball throwing device to pitch one or more balls to a player during said one or more ball trapping drills, enabling the player to practice trapping the ball and thereby improve ball control skills. The system can also include a training module that can record player training data that includes information regarding training of the player performed during the initial training program, submit the player training data over a network to a soccer network application along with a request for feedback from a remote coach through the soccer network application, and in response to submitting the training session data, receive a customized training program from the coach via the soccer network application. The customized training program can include one or more second drills to be executed by the soccer ball throwing device.

A method of controlling ball throwing devices can include, in some embodiments, receiving player training data from a plurality of controllers of ball throwing machines. The player training data can correspond to a plurality of players. In addition, the player training data can reflect usage by the players of the ball throwing machines. The method may also include electronically generating a remote coaching user interface by a computer system including computer hardware. The remote coaching user interface can include options for the coach to select recommended training programs for the players based on the player training data. The method can also include receiving, from the remote coaching user interface, coach-selected training programs to be sent to the plurality of controllers. Moreover, the method can include providing data representing the selected training programs to the plurality of controllers, thereby enabling the players to implement the selected training programs in the respective ball throwing machines of the players.

VII. Intelligent Goal System a. Intelligent Goal Structure

An "Intelligent Goal" ("goal") takes the concept of a traditional soccer goal and adds a plurality of sensors and, optionally, one or more lights and/or one or more speakers. In one embodiment, a miniaturized soccer goal may be utilized (e.g., have a height and width smaller than 24'×8'). Examples of sizes a goal may have include, but are not limited or restricted to, 24'×8', 12'×6', 6'×4', 4'×4', 4'×3', etc. The goal may include two side posts and a crossbar among other supporting posts. In one embodiment, the side posts, crossbar and supporting posts (collectively referred to as "posts") may be comprised of, for example, powder coated silver steel tubing. The posts may be comprised of alternative materials such as plastic tubes. In one or more embodiments, the posts may fold or be easily disassembled for convenient storage. A net (e.g., mesh or other material) may be attached to the posts to receive a soccer ball kicked between the posts.

Figure 21:
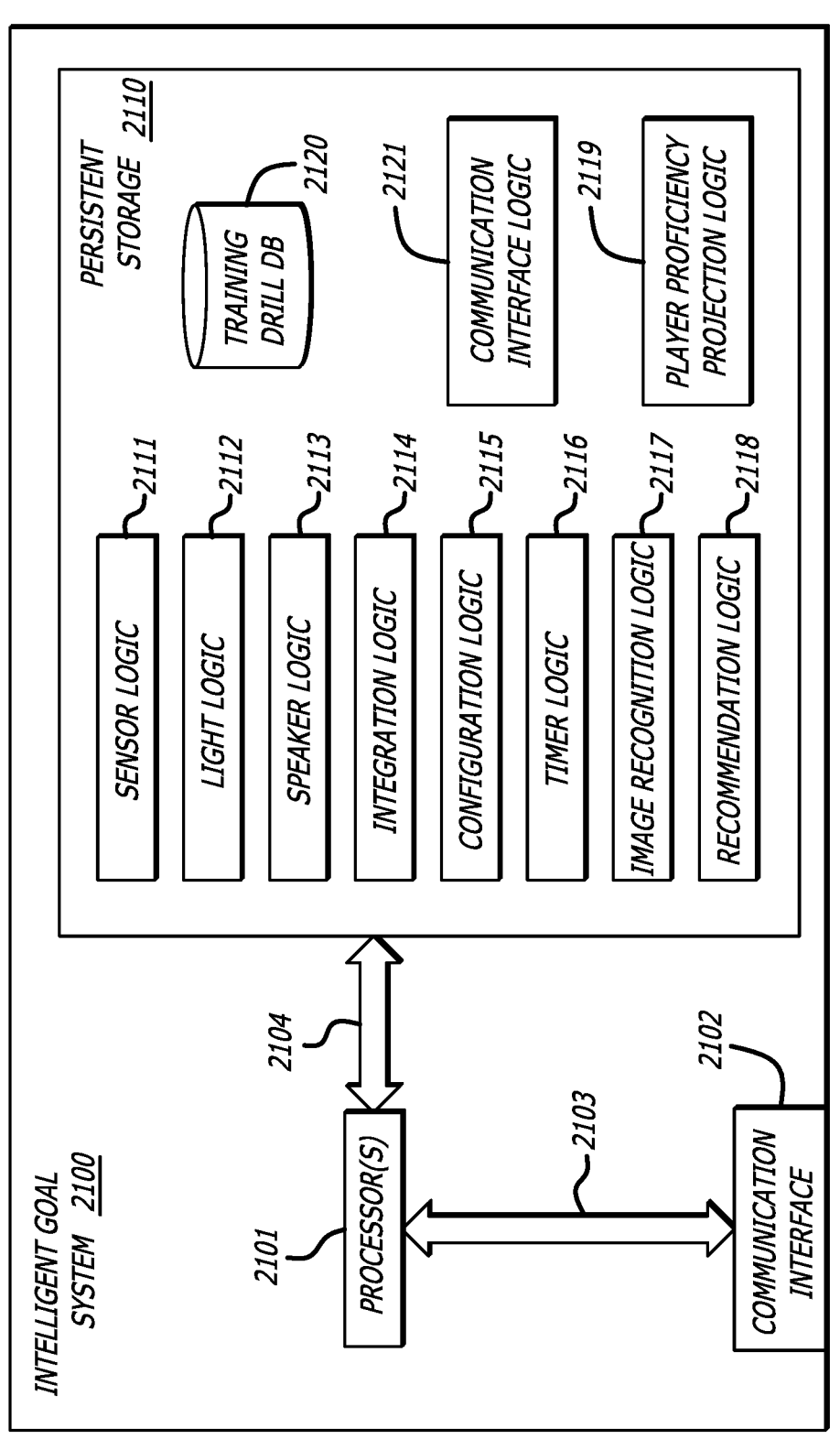
FIG. 21 is an exemplary embodiment of a logical representation of the intelligent goal logic.

In one embodiment, the side posts may include one or more sensors that are configured to detect the presence of a soccer ball crossing the plane created by the side posts and crossbar (referred to herein as the "goal plane"). In one embodiment, the plurality of sensors may include photoelectric sensor pairs (e.g., single-beam or dual-beam), wherein a pair includes two sensors (e.g., a transmitter and a receiver, or two sensors that act as both a transmitter and a receiver). In a first embodiment, a first transmitter of a first photoelectric sensor pair is attached to a first side post and a first receiver of the first photoelectric sensor pair is attached to a second side post, the first receiver and first transmitter aligned horizontally such that a through-beam of emitted light is transmitted from the first transmitter is received by the first receiver. The emitted light transmitted from the first transmitter to the first receiver is aligned with the goal plane. Therefore, when a soccer ball breaks the beam of emitted light, the first photoelectric sensor pair detects that the soccer ball has broken the goal plane (e.g., a goal was scored). In a second embodiment, the plurality of sensors may include a line of light emitting diodes (LEDs) coupled to a first side post and a line of detectors on the second side post. In one example, the number of LEDs included in the line of LEDs may be greater than the number of detectors in the line of detectors. In an alternative embodiment, a line of lasers may be used instead of, or in addition to, a line of LEDs. Other embodiments contemplated include the use of one or more cameras to record a ball breaking the goal plane. In such an embodiment, image recognition logic 2117, as seen in FIG. 21, would be utilized to determine when a ball breaks the goal plane and what portion of the goal plane (e.g., which zone) was broken. Alternatively, an ultrasonic system or a laser inferometry system may be used to detect when a ball breaks the goal plane. In yet another embodiment, the photoelectric sensor pair may comprise a retroreflective sensor pair that includes a first sensor being an emitter and a receiver in a single housing and a second sensor being a reflector that reflects the output from the first sensor back to the first sensor. In order to avoid the scenario in which a ball breaks the goal plane thereby triggering a through-beam interrupt and then bounces out of the goal, causing a second through-beam interrupt for the same ball (referred to herein as "double-counting"), it has been contemplated that the sensors may be turned off for a predetermined amount of time immediately following the first through-beam interrupt. It has also been contemplated that the sensors may remain on (e.g., detecting through-beam interrupts) but that the sensor logic, discussed below, may discard, or ignore a second through-beam interrupt that is detected within a predetermined amount of time following a first through-beam interrupt.

In some embodiments, a plurality of photoelectric sensor pairs is attached to the side posts such that a soccer ball crossing the goal plane will be detected. More particularly, the plurality of photoelectric sensor pairs is spaced apart vertically along the side posts such that a soccer ball cannot break the goal plane without interrupting at least one beam of emitted light. In one embodiment, the photoelectric sensor pairs are spaced apart to account for a soccer ball having a size "5" (e.g., having a circumference of 27-28 inches). Other embodiments may account for soccer balls of other sizes (e.g., a smaller gap between the photoelectric sensor pairs to account for smaller soccer balls), such as size "4," size "3," size "2," or size "1." Additionally, an embodiment may account for a custom-sized ball (e.g., having a diameter of 18 cm).

In one embodiment, the sensors may be built into the side posts. For example, the receivers of a first photoelectric sensor pair may be located within opposing side posts and an opening in each side post at the position of each receiver enables the beam of emitted light to be transmitted from the first transmitter to the first receiver. In an alternative embodiment, the sensors may be attached via an attachment mechanism (e.g., a Velcro strap or plastic mounting component) that enables the location of the sensors to be dynamic. In such an embodiment, the sensors may be adjusted according to a specific ball size (e.g., size "5") and at a later time, adjusted according to a second specific ball size (e.g., size "4"). In yet another embodiment, as will be shown below in FIG. 19C, a goal may include multiple sets of side posts such that a front set of side posts includes a plurality of lights integrated therein and a back set of side posts includes a plurality of sensors integrated therein.

Figure 18:
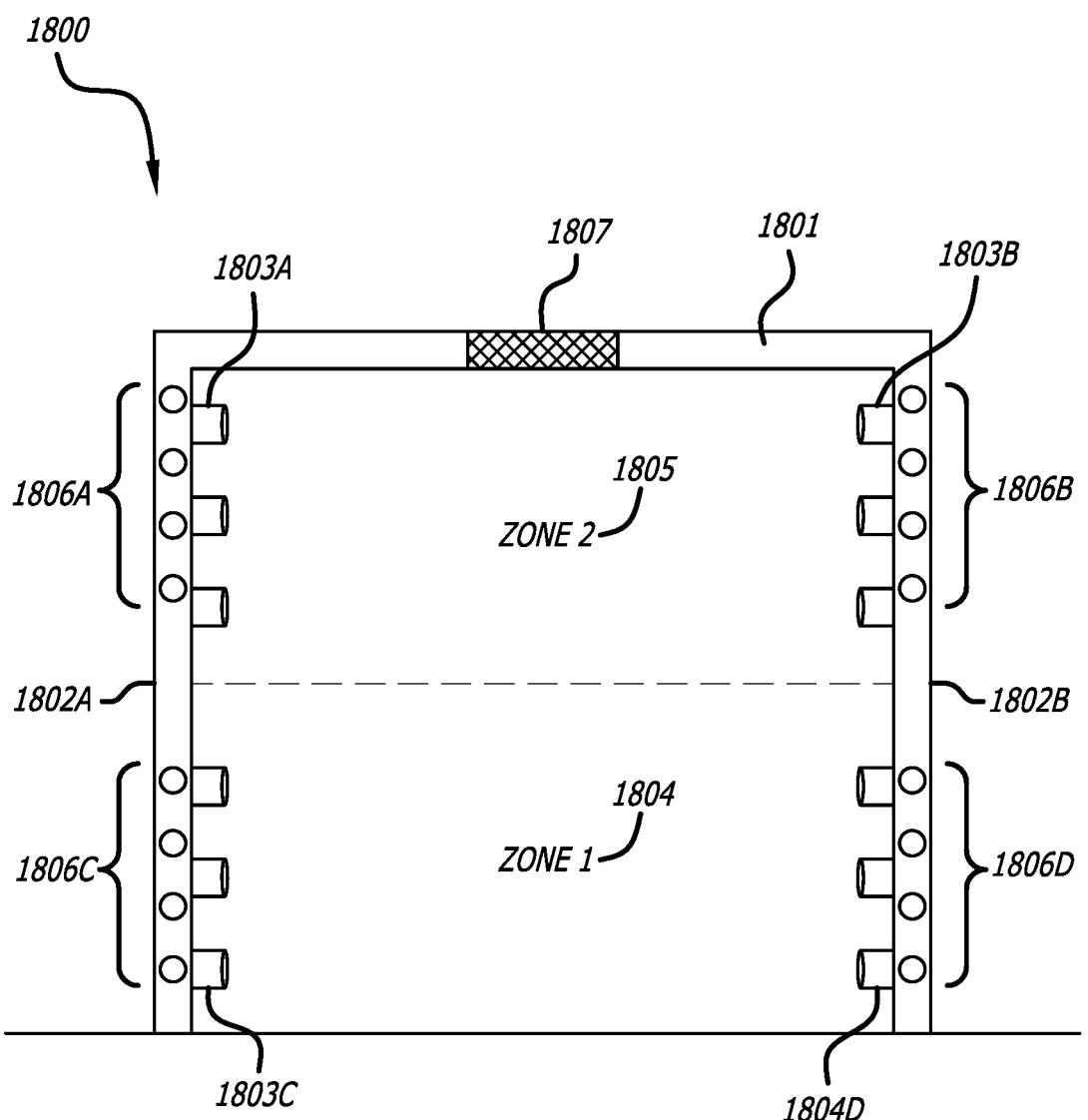
FIG. 18 is an embodiment of an intelligent goal having a plurality of sensors establishing multiple zones within the plane of the goal line and a plurality of lights.

Referring now to FIG. 18, an embodiment of an intelligent goal having a plurality of sensors establishing multiple zones within the plane of the goal line and a plurality of lights is shown. In one embodiment, as shown in FIG. 18, a goal 1800 may be formed by a crossbar 1801 and side posts 1802A-1802B, wherein a plane is created by the crossbar 1801 and the side posts 1802A-1802B (a "goal plane"). Additionally, the goal 1800 may include a plurality of sensors, wherein the plurality of sensors may be comprised of a plurality of subsections, e.g., sensors 1803A-1803D, wherein the sensors 1803A are paired with the 1803B, and the sensors 1803C are paired with the 1803D. For example, the sensors 1803A may transmit a through-beam (e.g., an infrared beam) to the sensors 1803B. In one embodiment, the sensors 1803B may comprise a reflector that reflects the through-beam back to the sensors 1803A. A goal is sensed when a ball interrupts the through-beam (e.g., breaks the goal plane). In the embodiment shown in FIG. 18, the sensors 1803C and 1803D create a first sensor pair, which creates a first zone 1804 within the goal plane, and the sensors 1803A and 1803B create a second sensor pair, which creates a second zone 1805 within the goal plane. In such an embodiment, the sensors of the goal 1800 are able to detect when a soccer ball crosses the goal plane and further distinguish as to whether the soccer ball broke the goal plane in the first zone 1804 or in the second zone 1805. It has been envisioned that additional zones may be created. In one embodiment, the first zone 1804 may be interpreted as a "passing zone" (e.g., a lower portion of the goal plane that incentives a player to pass a ball along the ground) such that a first training drill may require a predetermined number of balls to pass through the passing zone in order to complete or progress in the training. Additionally, in such an embodiment, the second zone 1805 may be interpreted as a "shooting zone" (e.g., an upper portion of the goal plane that incentives a player to shoot a ball above a predetermined height threshold). However, it is contemplated that for many users, a single zone will be established and that as users and better develop their skills, multiple zones may be established during one or more drills to increase the difficultly in the drill. It should be noted that the terms "user" and "player" are herein used interchangeably.

As will be discussed below in detail, the sensors 1803A-1803D may be dynamically configurable such that the size and number of zones formed by the sensors 1803A-1803D within the goal plane may be configurable based on a selected training drill. For example, a first training drill may result in the dynamic configuration of the sensors 1803A-1803D wherein two zones are formed (e.g., the first zone 1804 and the second zone 1805, as illustrated in FIG. 18). Continuing the example, a second training drill may result in the dynamic configuration of the sensors 1803A-1803D wherein three or more zones are formed. It is contemplated that the number of zones formed may equal to, or less than, the number of sensor pairs included within, or attached to, the goal (e.g., four sensor pairs may form one, two, three or four zones). It should be understood that a soccer ball may cross the goal plane in a plurality of zones. Dynamic configuration of a goal with multiple zones enables the location of a soccer ball crossing the goal plane to be detected at varying granularities that may be advantageous according to the skill level of the user (e.g., higher granularity useful for detecting precise placement of soccer balls by users with a high level of skill). As will be discussed below, the number of zones and/or the size of one or more zones may be dynamically reconfigured during a training drill. In yet additional embodiments, the size and number of zones formed by the sensors 1803A-1803D within the goal plane may be dynamically configurable based on one or more of: (i) a selected training drill, (ii) a skill level of a user, (iii) an age level of a user, and/or (iv) prior training records and/or training results of a player.

It is further contemplated that one embodiment of the goal may include a plurality of lights (e.g., LEDs lights) attached to, or located within, the side posts and/or the crossbar. The lights may be coupled with a timer and aid in timing. For example, four lights illuminated may indicate two minutes remaining; three lights illuminated may indicate one minute and thirty seconds remaining, etc. Alternatively, or in addition, the lights may be coupled to sensors (e.g., the sensors 1803A-1803D of FIG. 18) such that one light is turned on, or off, according to the number of goals scored (in total or in a particular zone).

Still referring to FIG. 18, the plurality of lights 1806A-1806D may be designated according to the zones discussed above, wherein the plurality of lights 1806A-1806D may be configured, e.g., controlled with software or firmware, to indicate to a user to kick the soccer ball through a specific zone. For example, one or more of the plurality of lights, e.g., 1806C and 1806D, may correspond to the first zone 1804 and may be illuminated to indicate a current training program requires the user to kick the soccer ball through the first zone 1804 of the goal 1800. In a second embodiment, each of the plurality of lights corresponding to the first zone 1804 (e.g., lights 1806C-1806D) may be illuminated and, as a soccer ball crosses the plane of the goal 1800 through the first zone 1804, a light may be turned off. A predetermined soccer drill may utilize such a configuration of the plurality of the lights 1806A-1806D (e.g., communicatively coupled to the sensors 1803A-1803D) in order to instruct a user though which zone of the goal 1800 to kick the ball. As mentioned above, the plurality of lights 1806A-1806D, communicatively coupled to the sensors 1803A-1803D, may also aid in score keeping and/or aid in timing.

In one embodiment, the plurality of lights 1806A-1806D may comprise a plurality of colored LEDs wherein the colored LEDs are illuminated according to a predetermined drill. As discussed below, logic may store instructions corresponding to the predetermined drill such that predetermined colored LEDs are illuminated according to a predetermined timing scheme or a predetermined scoring scheme (e.g., based on input received from the sensors). In addition, the logic may include instructions to randomize the illumination of the colored LEDs where different colored LEDs correspond to different drills to be performed or zones of the goal to kick a ball through.

As discussed above with respect to the sensors 1803A-1803D, the plurality of lights 1806A-1806D may be dynamically configurable according to the configuration of the number of zones. For example, referring to FIG. 18, the sensors 1803A-1803D may be dynamically configured into two zones at the start of a training drill. Further, the plurality of lights 1806A-1806D may be dynamically configured into subsections corresponding to the two zones. For example, the sensors 1803A-1803B may correspond to the second zone 1805 and the sensors 1803C-1803D may correspond to the first zone 1804. The plurality of lights 1806A-1806D may be dynamically configured in a different manner (e.g., configured into subsections corresponding to three zones) according to a second training drill.

Some embodiments of the goal 1800 may include one or more speakers 1807 ("speakers") such that audible cues may be provided to the user, in addition or as an alternative to, the lights 1806A-1806D discussed above. For example, predetermined instructions or messages may be included within a drill such that the speakers may alert the user of a current training drill to perform, a method of performing the training drill (e.g., which foot to use), scoring and/or timing. The speakers 1807, communicatively coupled to a memory and/or processor, may also provide audible congratulatory messages (e.g., scoring milestones within a drill), which may be combined with a visual congratulatory message (e.g., via a scoreboard, via lights coupled to the intelligent goal, etc.). As discussed above with respect to the sensors 1803A-1803D, the speakers 1807 may be built into the posts or may be attached via an attachment mechanism (e.g., a Velcro strap or plastic mounting component) that enables the location of the speakers 1807 to be dynamic. In an alternative embodiment, illustrated in FIG. 19E, the speakers may be located on the backside of the goal (e.g., in a housing). For example, the housing may include the speaker and may be adjacent, or coupled to, a supporting post of the goal. It should be understood that the term speaker as used herein may also refer to headphones (e.g., Bluetooth® Low-Energy (BLE) wireless headphones or wired headphones that are coupled to an electronic device worn or carried by the user while participating in the one or more drills).

Figure 19A:
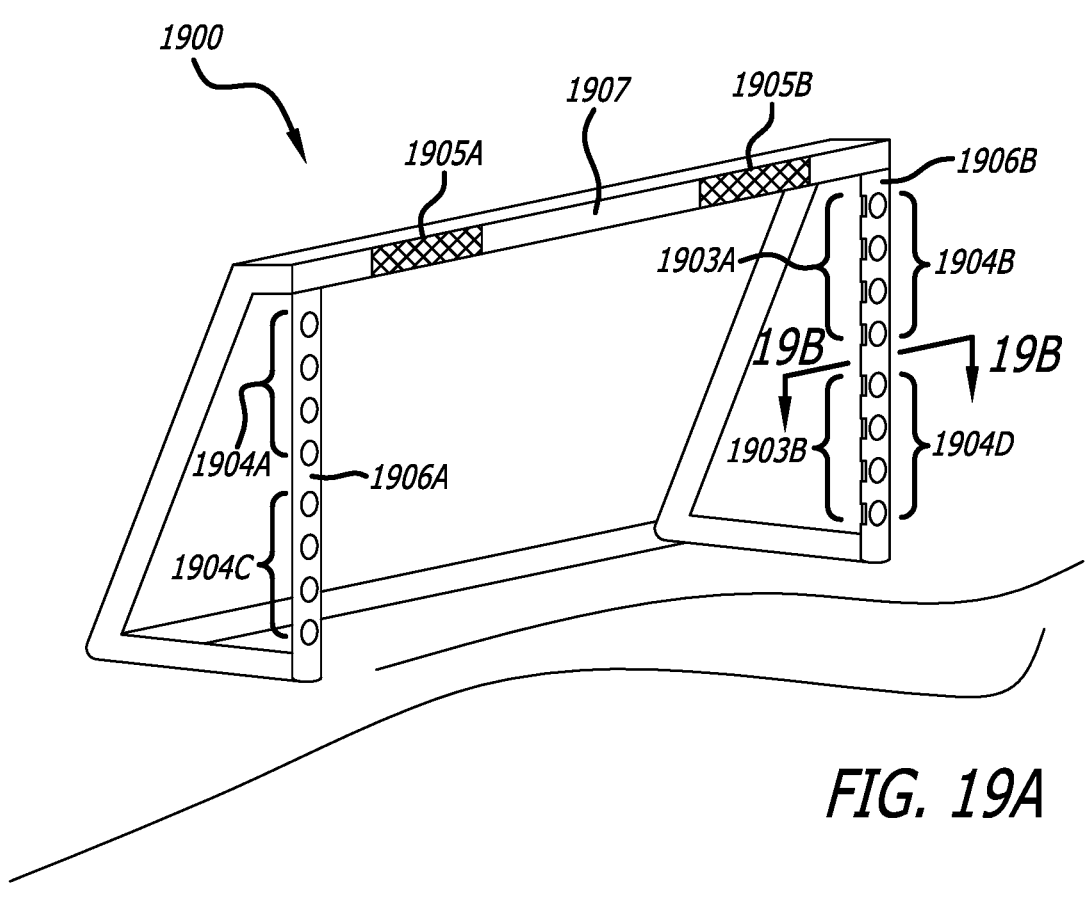
FIG. 19A is a front side view of an embodiment of an intelligent goal.
Figure 19B:
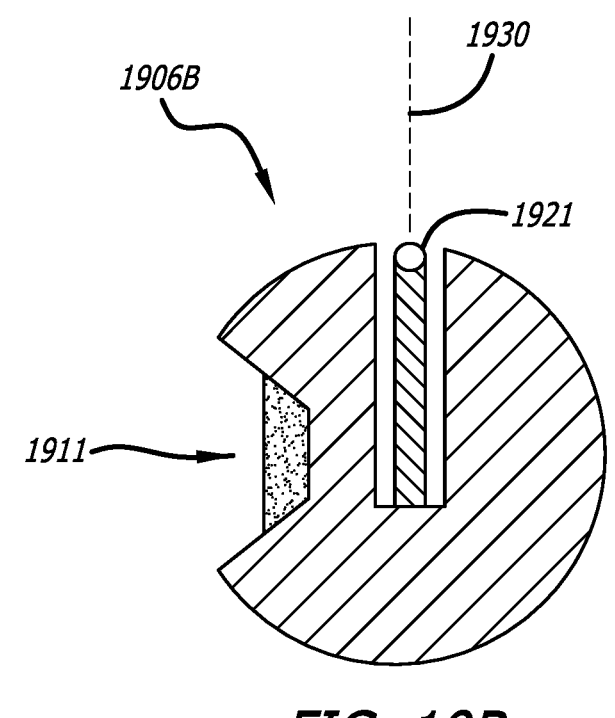
FIG. 19B is a top cross-sectional view of an embodiment of the intelligent goal as seen in FIG. 19A, which includes the side post having a plurality of lights and a plurality of sensors integrated therein.

Referring to FIG. 19A, a front side view of an embodiment of an intelligent goal is shown. The goal 1900 is structurally comprised of a crossbar 1907, side posts 1906A-1906B and additional supporting posts (collectively referred to hereinafter as "posts"), wherein the crossbar 1907 and side posts 1906A-1906B form a plane (e.g., a "goal plane"). The goal 1900, as illustrated, also includes a plurality of sensors 1903A-903B (e.g., photoelectric sensors), a plurality of lights 1904A-1904D (e.g., LED lights) and speakers 1905A-1095B. It should be understood that one or more of the plurality of lights 1904A-1904D and the speakers 1905A-1905B are optionally included in the goal 1900. In one embodiment, as shown in FIG. 19F, the plurality of lights may be located on the crossbar instead of on the sideposts and/or may be located on both the crossbar and on one or more sideposts. In the embodiment illustrated in FIG. 19A, the sensors 1903A-1903B, the plurality of lights 1904A-1904D and the speakers 1905A-1905B are integrated into the posts. As one example, the plurality of sensors 1903A-1903B is located within a side post 1906A or 1906B (corresponding sensors are located in the opposing side post but cannot be seen). Specifically, the front side of each of the plurality of sensors 1903A-1903B may be flush with the side post, the front side of each of the plurality of sensors 1903A-1903B may be recessed within the side post (e.g., allowing a cover to slide over each of the plurality of sensors 1903A-1903B are not in use), or the front side of each of the plurality of sensors 1903A-1903B may be partially extended from the side post. The plurality of lights 1904A-1904D and the speakers 1905A-1905B may be configured similarly to the plurality of sensors 1903A-1903B as discussed above. Referring to FIG. 19B, a top cross-sectional view of an embodiment of the intelligent goal 1900 as seen in FIG. 19A, which includes the side post 1906B having a plurality of lights and a plurality of sensors integrated therein is shown. The light 1911 faces the user (e.g., front-facing) and is recessed within the side post 1906B. The side post 1906B also includes a sensor 1921 integrated therein. The goal plane 1930 is shown to extend perpendicular to the front of the goal (e.g., the direction facing the user) and in a direction toward a corresponding sensor in a corresponding side post, e.g., the side post 1906A (not shown).

Figure 19C:
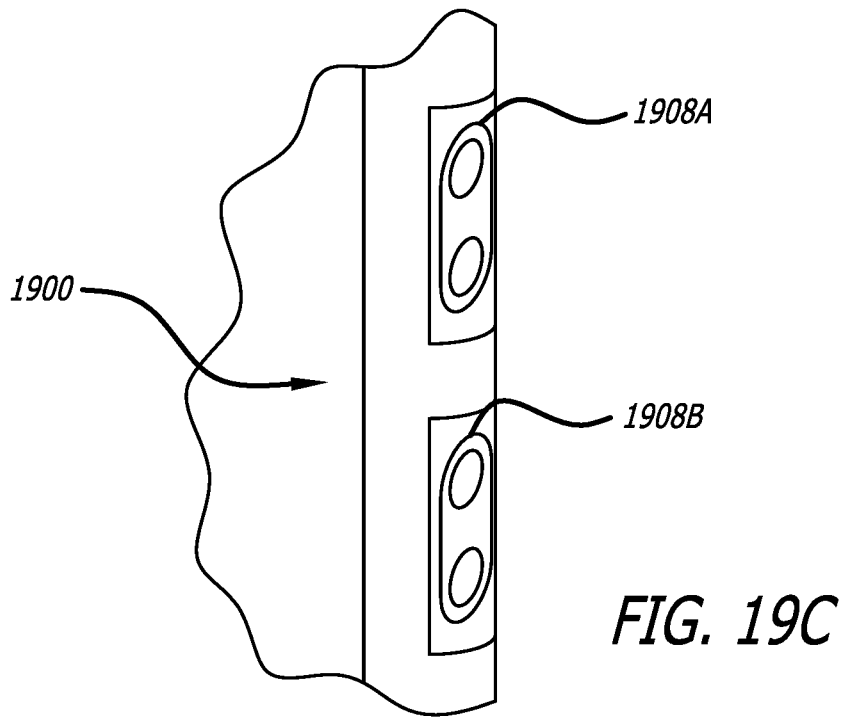
FIG. 19C is a side view of a sectional portion of a side post of the goal 1900 including a plurality of sensors.

Referring to FIG. 19C, a side view of a sectional portion of a side post of the goal 1900 including a plurality of sensors is shown. FIG. 19C illustrates sensors 1908A-1908B integrated into a side post 1906A or 1906B of the goal 1900. The sensors 1908A-1908B are illustrated as dual-beam photoelectric sensors (e.g., each having two optical sensors); however, alternative sensors may be used.

Figure 19D:
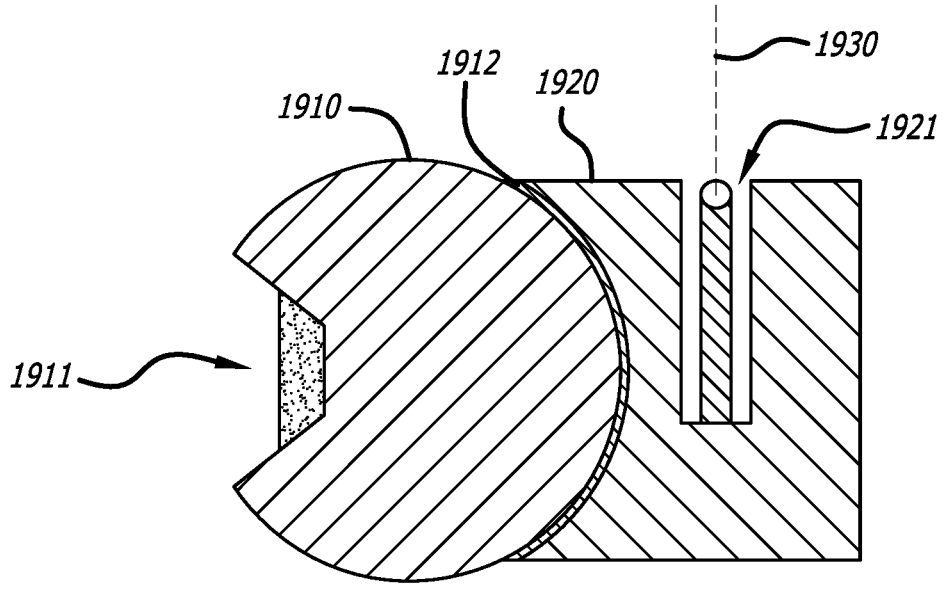
FIG. 19D is a top perspective of an embodiment of an intelligent goal including a front set of side posts having a plurality of lights integrated therein and a back set of side posts having a plurality of sensors integrated therein.
Figures 19E, 19F, 20:
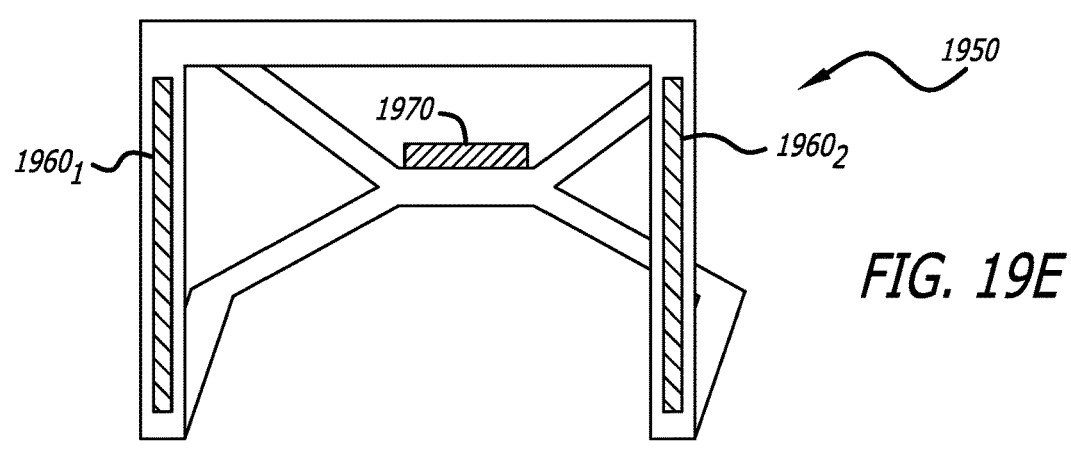
FIG. 19E is front view of an embodiment of an intelligent goal including a housing including one or more speakers.
FIG. 19F is a front side view of an embodiment of an intelligent goal including a plurality of sensors located proximate to upper corners of the intelligent goal.
FIG. 20 is a front side view of a sectional portion of a side post, the crossbar and additional supporting posts of the goal 2000 including a plurality of attachable sensors and an attachable speaker.

Referring now to FIG. 19D, a top perspective of an embodiment of an intelligent goal including a front set of side posts having a plurality of lights integrated therein and a back set of side posts having a plurality of sensors integrated therein is shown. In the perspective view of FIG. 19D, a front side post 1910 and a back side post 1920 of the goal 1900 are shown. The front side post 1910 includes a light 1911 integrated therein. The light 1911 faces the user (e.g., front-facing) and is recessed within the front side post 1910. The back side post 1920 is positioned behind the front side post 1910 with respect to the user and includes a sensor 1921 integrated therein. The goal plane 1930 is shown to extend perpendicular to the front of the goal (e.g., the direction facing the user) and in a direction toward a corresponding sensor in a corresponding side post (not shown). In some embodiments, a dampening material 1912 may be included between at least a portion of the front side post 1910 and the back side post 1920 to absorb some of the impact when a ball hits the front side post 1910. Additionally, in some embodiments, the back side post 1920 may be designed to conform to the shape of the front side post 1910.

Referring now to FIG. 19E, a front view of an embodiment of an intelligent goal including a housing that includes one or more speakers is shown. A goal 1950 is comprised of crossbar, side posts and supporting posts. The goal 1950 may include light strips $1960_1$-$1960_2$ and a housing 1970 that may include one or more of a circuit board (e.g., including circuitry, a processor, and non-transitory computer-readable medium having stored thereon logic), a battery and/or one or more speakers.

Referring now to FIG. 19F, a front side view of an embodiment of an intelligent goal including a plurality of sensors located proximate to upper corners of the intelligent goal is shown. The goal 1980 may include a plurality of lights $1981_1$-$1981_4$ on one or more of the side posts and/or the crossbar. In addition, the goal 1980 includes a plurality of sensors $1990_1$-$1990_2$ coupled to the crossbar and sideposts proximate to the upper corners of the goal 1980. The sensors $1990_1$-$1990_2$ may be any type of sensor as discussed above. One purpose of the sensors $1990_1$-$1990_2$ is to detect balls that break the goal plane in the upper corners of the goal 1980 (often referred to as the "upper 90"). A sensor pair of the sensors 1990₁-1990₂ may be placed at predetermined angles relative to the crossbar and sideposts to include a detection space within each upper 90. For example, a first sensor of a sensor pair of the sensors 1990₁-1990₂ may be placed at a 45° angle relative to the crossbar and a second sensor of a sensor pair of the sensors 1990₁-1990₂ may be placed at a 45° angle relative to a sidepost. One or more sensor pairs may be included in each of the sensors 1990₁-1990₂.

Referring now to FIG. 20, a front side view of a sectional portion of a side post, the crossbar and additional supporting posts of the goal 2000 including a plurality of attachable sensors and an attachable speaker is shown. As illustrated, the attachable sensors 2001A-2001B are coupled to a side post of the goal 2000 and include attachment mechanisms 2002A-2002B, respectively. The attachment mechanisms 2002A-2002B may include straps (e.g., Velcro® straps), plastic components with an interlocking mechanism or straps/coupling components of alternative materials. Similarly, the attachable speaker 2003 is coupled to the crossbar of the goal 2000 and includes an attachment mechanism 2004, which may include any of the embodiments discussed with respect to the attachable sensors 2001A-2001B. Advantages to the attachable sensors 2001A-2001B include an ease of physical configuration and compatibility with multiple goals. For example, a user may utilize one or more sensor pairs with a first standard goal (i.e., no sensor integration within the goal posts) and thereby physically configure one or more zones within the goal plane. The attachable sensors 2001A-2001B may then be detached from the goal posts and attached to a second standard goal at a location remote from the first standard goal. Similarly, the attachable speaker 2003 and/or the attachable lights 2005A-2005B may be attached and detached to a plurality of goals (standard or those with integrated sensors and or lights) using the attachment mechanisms 2004 and 2006A-2006B, respectively. Additionally, with respect to battery-operated sensors, lights and/or speakers, the ability to detach the sensor, light and/or speaker provides for ease in changing a battery. It should be noted that the sensors, lights and/or speakers (attachable and/or integrated into a goal) may be battery operated and/or provided power through an external power source.

Although embodiments described herein focus on the sport of soccer, embodiments pertaining to other sports have been contemplated. The invention described herein is applicable to any sport that is centered around the accuracy of a player to place a ball at a particular location. As a first example, a receiving device may take the shape of a square (or alternative shape) that simulates a "strike zone" in baseball wherein the receiving device includes a plurality of sensors that establishes zones within the strike zone and the lights indicate whether the player placed a baseball (via a pitch) in a particular zone. As a second example, a football goal post may include a plurality of sensors that establishes zones within the plane of the goal post and the plurality of lights indicate whether the player placed a football in a particular zone. Alternatively, a receiving device may take the shape of a square (or alternative shape) that simulates a target area for a quarterback wherein the receiving device includes a plurality of sensors that establishes zones within the plane created by the square shape and the lights indicate whether the player placed a football (via a throw) in a particular zone. Similar goals or training aids have been contemplated for sports such as, but not limited or restricted to, softball, basketball, hockey, tennis, golf, lacrosse, and/or basketball.

B. Intelligent Goal Logic

A goal may also include non-transitory computer-readable medium (e.g., memory) and one or more processors. The goal may alternatively be communicatively coupled to memory and one or more processors (e.g., communicate via a wired or wireless network). The memory may store logic that includes executable instructions (e.g., software), that when executed by the one or more processors, cause predetermined functions of the sensors, one or more of the plurality of lights and/or the speakers. In one embodiment wherein the goal includes non-transitory computer-readable medium (e.g., memory) and one or more processors, the logic of the goal may communicate directly with a coach's device to receive instructions regarding a selected training drill. In a second embodiment wherein the goal is communicatively coupled to the memory and the one or more processors that are both located on a remote electronic device (e.g., a computer, a server or other electronic device), the goal may receive instructions regarding a selected training drill from the remote electronic device, which communicates directly with the coach's device.

The logic of the goal may include: (i) a sensor logic, (ii) a light logic, (iii) a speaker logic, (iv) an integration logic, (v) a configuration logic, (vi) a timer logic, (vii) image recognition logic, (viii) recommendation logic and/or (ix) player proficiency projection logic. The sensor logic may receive input from one or more sensor pairs. As discussed above, a sensor pair comprises a first sensor and a second sensor positioned opposite each other and aligned with the goal plane. The sensor logic receives a signal from one or more sensor pairs that the through-beam corresponding to the sensor pair was interrupted, thus indicating the goal plane was broken (i.e., a goal was scored). The sensor logic determines from which sensor pair the signal was received and determines the zone corresponding to the sensor pair. The sensor logic may determine from which sensor pair the signal was received by, for example, parsing the received signal for an identifier corresponding to a specific sensor pair included in the received signal. The sensor logic may provide information associated with the signal (e.g., from which sensor pair the signal was received, the zone corresponding to the sensor pair, etc.) to the integration logic. The sensor logic may include the ability to detect the speed of a ball via detection of a through-beam interrupt. For example, the sensor logic may determine the time duration of the through-beam interrupt, and based on the size of the ball (e.g., included in the instructions regarding the selected training drill), determine the speed at which the ball was traveling. Alternatively, such a determination may be performed in combination with the timer logic. Furthermore, the sensor logic may include the ability to detect the trajectory of a ball upon the detection of a goal. Particularly, the sensor logic may detect two or more through-beam interrupts within a predetermined amount of time (e.g., milliseconds) such that the two or more through-beam interrupts correspond to a single ball breaking the plane of the intelligent goal. The trajectory of the ball may be determined according to the order in which the through-beam interrupts were detected. For example, in the scenario in which a through-beam interrupt corresponding to a lower sensor was detected prior to a through-beam interrupt corresponding to an upper sensor, the sensor logic may determine the ball had an upward trajectory while breaking the goal plane (e.g., that the ball bounced immediately prior to the breaking the plane of the intelligent goal). Similar determinations may be made when (i) a through-beam interrupt of an upper sensor is detected immediately prior to detection of a through-beam interrupt of a lower sensor (e.g., ball had a downward trajectory), (ii) two through-beam interrupts were detected simultaneously (e.g., ball had approximately a straight trajectory through the goal plane), etc.

The light logic may receive at least a portion of instructions associated with a selected training drill, and provide input, according to instructions associated with the selected training drill, to one or more lights integrated with or attached to the goal. In one embodiment, the light logic may parse the instructions associated with the selected training drill to determine whether one or more lights are to be turned on and if so, for what duration. In a second embodiment, the light logic receives input from the integration logic that has parsed the instructions associated with the selected training drill, which provides the light logic with the information required to turn on one or more lights, and for what duration, if necessary. The light logic is communicatively coupled to the timer logic such that the light logic provides the timer logic with the required time intervals and receives a notification from the timer logic when a time interval expires. Based on either (i) parsing instructions associated with the training drill, or (ii) instructions received from the integration logic or the timer logic, the light logic may turn on or off one or more lights. For example, a selected training drill may begin with each of the lights included in the goal turned on and when a player scores a goal, one light turns off such that the purpose of the training drill is to turn off all of the lights (additionally, a time component may be incorporated wherein the player has a predetermined amount of time to turn off all of the lights). Although the example includes turning off the lights, it should be understood that the lights may be turned on instead and the training drill maintain the same purpose. In some embodiments, the light logic may cause one or more lights to turn on or off, wherein the one or more lights may remain illuminated or may blink in a periodic manner.

As discussed above with respect to the sensor logic and the light logic, the speaker logic may receive at least a portion of instructions associated with a selected training drill and provide input, according to the instructions associated with the selected training drill, to one or more speakers integrated with or attached to the goal. The speaker logic may include, but is not limited or restricted to the following functionality, provide audible cues as to the beginning and end of a training drill, and/or provide audible cues during a training drill pertaining to timing, scoring, and player-instructions (e.g., with which foot to kick the ball, at which goal to shoot, at which zone to shoot, etc.). The speaker logic may receive input from the configuration logic that causes the speaker to provide audible cues as to the configuration settings of one or more zones according to a selected training drill. The speaker logic may also receive input from the integration logic and the timer logic that cause the speaker to provide audible cues as to scoring and timing, respectively. Additionally, the speaker logic may cause music to play from the speakers. The music may be retrieved from an electronic device, e.g., a phone, tablet, coach's device, etc., via a wired or wireless connection, or from a storage device of the goal, if applicable.

The integration logic receives input from the sensor logic and, responsive to the selected training drill and the received input, provides input to the light logic and/or the speaker logic. For example, the integration logic may provide input to the light logic that a ball has interrupted a through-beam of a sensor pair in a required zone as set forth by the selected training drill. Accordingly, the light logic may turn on a predetermined light (or turn off, as discussed above) and select a color according to the selected training drill. For example, the light logic may turn on and turn off one or more lights (e.g., blink) as a form of feedback when a goal is scored and/or change a color of one or more lights (e.g., briefly and return to a previous color or for at least a portion of the remainder of the drill). Similarly, responsive to the selected training drill and received input from the sensor logic, the integration logic may provide input to the speaker logic pertaining to an audible cue that is to be provided by the speakers. Furthermore, the integration logic may receive input from the configuration logic pertaining to the configuration, or reconfiguration, of one or more zones. The integration logic may subsequently provide input to the sensor logic, the light logic and/or the speaker, wherein the input may cause reconfiguration of one or more zones, adjustment of one or more lights, and/or an audible cue to be provided to a user. The integration logic, in communication with the sensor logic, may record the color of a light corresponding to the through-beam that was interrupted (e.g., of the zone or goal) upon detection of a through-beam interrupt by the sensor logic.

A configuration logic may receive instructions associated with the selected training drill, parse the instructions, and provide input to one or more of the sensor logic, the light logic and/or the speaker logic. In particular, the configuration logic may determine, based on the selected training drill, which sensor pairs correspond to each zone and provide the determination to the sensor logic. Similarly, the configuration logic may determine, based on the selected training drill, which lights correspond to each zone and provide the determination to the light logic. Furthermore, information of the zones established according to the selected training drill may be provided to a user via an audible cue according to input provided by the configuration logic to the speaker logic. In one embodiment, the selected training drill may include reconfiguration of one or more zones during the training drill (referred to herein as "dynamic reconfiguration"). For example, in one exemplary training drill, after a first predetermined number of goals are scored in a first zone (e.g., upper half of the goal plane), the training drill may require a second predetermined number of goals to be scored in a second zone (e.g., upper quarter of the goal plane). In such an example, responsive to receiving input from the sensor logic and/or integration logic signifying the first predetermined number of goals have been scored in the first zone, the configuration logic provides input to the sensor logic and/or the light logic to dynamically reconfigure the sensors and/or the lights to establish the second zone. The configuration logic may be in communication with the sensor logic and, upon detection of a through-beam interrupt by the sensor logic, record the zone corresponding to the through-beam that was interrupted (e.g., through which zone a goal was scored).

A timer logic may maintain one or more timers corresponding to one or more portions of a training drill (e.g., a first timer corresponding to a first predetermined amount of time to maintain establishment of a first set of zones and a second timer corresponding to a second predetermined amount of time to maintain establishment of a second set of zones). The timer logic may be configured to control several time intervals for, inter alia, turning on or off of one or more lights, dynamic configuration of one or more zones established by the sensors, determining a period between a first ball and a second ball being provided by a ball throwing machine, etc. As a first example, the timer logic may be configured to control a timer that indicates the time duration of a training drill wherein one or more lights turn on for the time duration of the drill and turn off following the expiration of the time duration of the drill. As a second example, the timer logic may be configured to control a plurality of timers (e.g., one timer per light) such that the timer logic instructs the light logic of a first goal to turn on a plurality of lights for a first time duration and, at the expiration of the first time duration, instructs the light logic to turn off a first light while at least a second light remains on. Continuing the example, at the expiration of a second time duration—the second time duration being longer than the first time duration—the timer logic instructs the light logic to turn off the second light. In yet another example, the timer logic may be configured to instruct the light logic of a first goal to turn on at least a first light of the first goal for a first time duration and at the expiration of the first time duration, instruct the light logic of the first goal to turn off the first light and instruct the light logic of a second goal to turn on at least a first light of the second goal for a second time duration. It has also been contemplated that the timer logic may be configured to control one or more timers for any of the sensor logic, the light logic, the speaker logic, and/or the integration logic. The timer logic may also be in communication with the sensor logic such that a timestamp is recorded for each through-beam interrupt detected by the sensor logic.

In one embodiment, the training drill database may store predetermined training drills (e.g., input or instructions) for retrieval by one or more of the sensor logic, the light logic, the speaker logic, the integration logic, the configuration logic, the timer logic and/or the image recognition logic ("the intelligent goal logic"). Notification of a selected training drill may be provided to the intelligent goal logic by, for example, a coach's device using an identifier of the selected training drill. One or more components of the intelligent goal logic may retrieve the selected training drill, or instructions associated therewith, based on the provided identifier.

The training drill database may also store all of the input and/or feedback associated with a training session (e.g., one or more training drills encompassing one instance in which user utilizes the goal) and provides the input and/or feedback to the coach's device and/or a cloud server for storage. Such input and/or feedback may be connected to a user's profile and used to provide customized feedback to the user, rank the user based on the input and/or feedback against predetermined goals or statuses (e.g., "beginner," "amateur," "professional") and/or other users (based on age, gender, drill, overall, etc.), and/or used, at least as a factor, in determining future training sessions for the player (e.g., either via logic that performs the determination automatically prior to or at the initiation of a training session or manual human determination, e.g., recommendation logic 2118 as seen in FIG. 21).

1. Logical Representation

Referring to FIG. 21, an exemplary embodiment of a logical representation of the intelligent goal logic as discussed above is shown. As discussed above, a goal may either (i) include non-transitory computer-readable medium (e.g., memory) and one or more processors, or (ii) be communicatively coupled to the memory and the one or more processors located in a remote electronic device, wherein instructions are communicated to the goal a wired or wireless network.

In the embodiment in which the intelligent goal logic is included within a goal, the goal may include a housing, which is made entirely or partially of a hardened material (e.g., hardened plastic, metal, glass, composite or any combination thereof) that protects circuitry within the housing, namely one or more processors 2101 that are coupled to a communication interface 2102 via a first transmission medium 2103. Alternatively, the intelligent goal logic may be located in an electronic device physically separate from the goal that communicates with the sensors, lights and/or speakers integrated in or attached to the goal. In such an embodiment, the electronic device includes a housing that protects circuitry within the housing, e.g., the one or more processors 2101 that are coupled to a communication interface 2102 via a first transmission medium 2103.

In either embodiment, the communication interface 2102 in combination with communication interface logic 2121 enables communications with the sensors, lights and/or speakers, one or more coach's devices and/or remote electronic devices. According to one embodiment of the disclosure, the communication interface 2102 may be implemented as a physical interface including one or more ports for wired connectors. Additionally, or in the alternative, the communication interface 2102 may be implemented with one or more radio units for supporting wireless communications with other electronic devices. The communication interface logic 2117 may include logic for performing operations of receiving and transmitting one or more objects via the communication interface 2102 to enable communication between sensors, lights and/or speakers, one or more coach's devices, remote electronic devices and/or cloud computing services.

The processor(s) 2101 is further coupled to persistent storage 2110 via a second transmission medium 2104. According to one embodiment of the disclosure, the persistent storage 2110 may include (i) the sensor logic 2111, (ii) the light logic 2112, (iii) the speaker logic 2113, (iv) the integration logic 2114, (v) the configuration logic 2115, (vi) the timer logic 2116, (vii) the image recognition logic 2117, (viii) the recommendation logic 2118, (ix) the player proficiency projection logic 2119, (x) the communication interface logic 2121, and (xi) a training drill database 2120. Of course, when implemented as hardware, one or more of these logic units could be implemented separately from each other.

2. Exemplary Methodology

Referring to FIG. 22, a flowchart illustrating an exemplary method for configuring and operating the intelligent goal according to a selected training drill is shown. Each block illustrated in FIG. 22 represents an operation performed in the method 2200 of configuring and operating the intelligent goal according to a selected training drill. As discussed above, an intelligent goal may either (i) include non-transitory computer-readable medium (e.g., memory or storage device) and one or more processors, or (ii) be communicatively coupled to the memory and the one or more processors located in a remote electronic device, wherein instructions are provided to the intelligent goal via a wired or wireless communication. Referring to block 2201, the intelligent goal system receives a selection of a training drill. For example, the intelligent goal system may receive a signal from a coach's device that identifies the selected training drill.

At block 2202, the intelligent goal system parses one or more instructions associated with the selected training drill. The intelligent goal system may (i) be provided with the one or more instructions associated with the selected training drill, or (ii) retrieve one or more instructions associated with the selected training drill from a storage device as discussed above.

At block 2203, the intelligent goal system configures one or more sensors and/or lights into one or more zones aligned with the goal plane. As discussed above, the configuration logic of the intelligent goal system may determine, based on the selected training drill, which sensor pairs correspond to one or more zones (set forth in the instructions associated with the training drill) and provide the determination to the sensor logic, which configures the sensors accordingly.

At block 2204, the intelligent goal system receives a signal from a first sensor pair signifying a through-beam has been interrupted (i.e., a goal was scored). At block 2205, the intelligent goal system determines whether the through-beam interrupt corresponds to the end of the selected training drill. For example, a through-beam interrupt may correspond to the end of the selected training drill when the through-beam interrupt a predetermined number of goals scored in a particular zone (e.g., the training drill consists of scoring five goals in a first zone, wherein the through-beam interrupt representing the fifth goal in the first zone represents the end of the training drill). Additional variations exist wherein a through-beam interrupt would signify the end of the training drill (e.g., the through-beam signifies a predetermined number of goals scored outside of a particular zone). Furthermore, input may be received from the ball throwing machine, as discussed below, that signifies the end of the training drill (e.g., a predetermined number of balls has been provided to a user), wherein the input from the ball throwing machine is used in place of the signal representing a through-beam interrupt. When the intelligent goal system determines the through-beam interrupt corresponds to the end of the selected training drill (yes at block 2205), the method 2200 ends (block 2206).

When the intelligent goal system determines the through-beam interrupt does not correspond to the end of the selected training drill (no at block 2205), the intelligent goal system determines whether the through-beam interrupt corresponds to a predetermined zone based on the selected training drill (block 2207). For example, a through-beam interrupt may correspond to a predetermined zone based on the selected training drill when the through-beam interrupt does not signify that a predetermined number of goals has been scored in a particular zone (e.g., the training drill consists of scoring five goals in a first zone, wherein the through-beam interrupt representing the third goal in the first zone does not represent the end of the training drill). When the intelligent goal system determines the through-beam interrupt does not correspond to a predetermined zone based on the selected training drill (no at block 2207), the method 2200 returns to block 2204 to receive a second signal from one or more of the sensor pairs integrated with or attached to the intelligent goal.

Optionally, when the intelligent goal system determines the through-beam interrupt corresponds to a predetermined zone based on the selected training drill (yes at block 2207), the intelligent goal system alters the state of one or more lights (block 2208). For example, when a training drill consists of scoring a predetermined number of goals in a first zone, the logic of the intelligent goal system may cause (i) a first light integrated with or attached to the intelligent goal to turn on responsive to a first goal scored in the predetermined zone, (ii) a second light integrated with or attached to the intelligent goal to turn on responsive to a second goal scored in the predetermined zone, etc.

C. Ball Throwing Machine, Coach's Device and Intelligent Goal System

Figure 23:
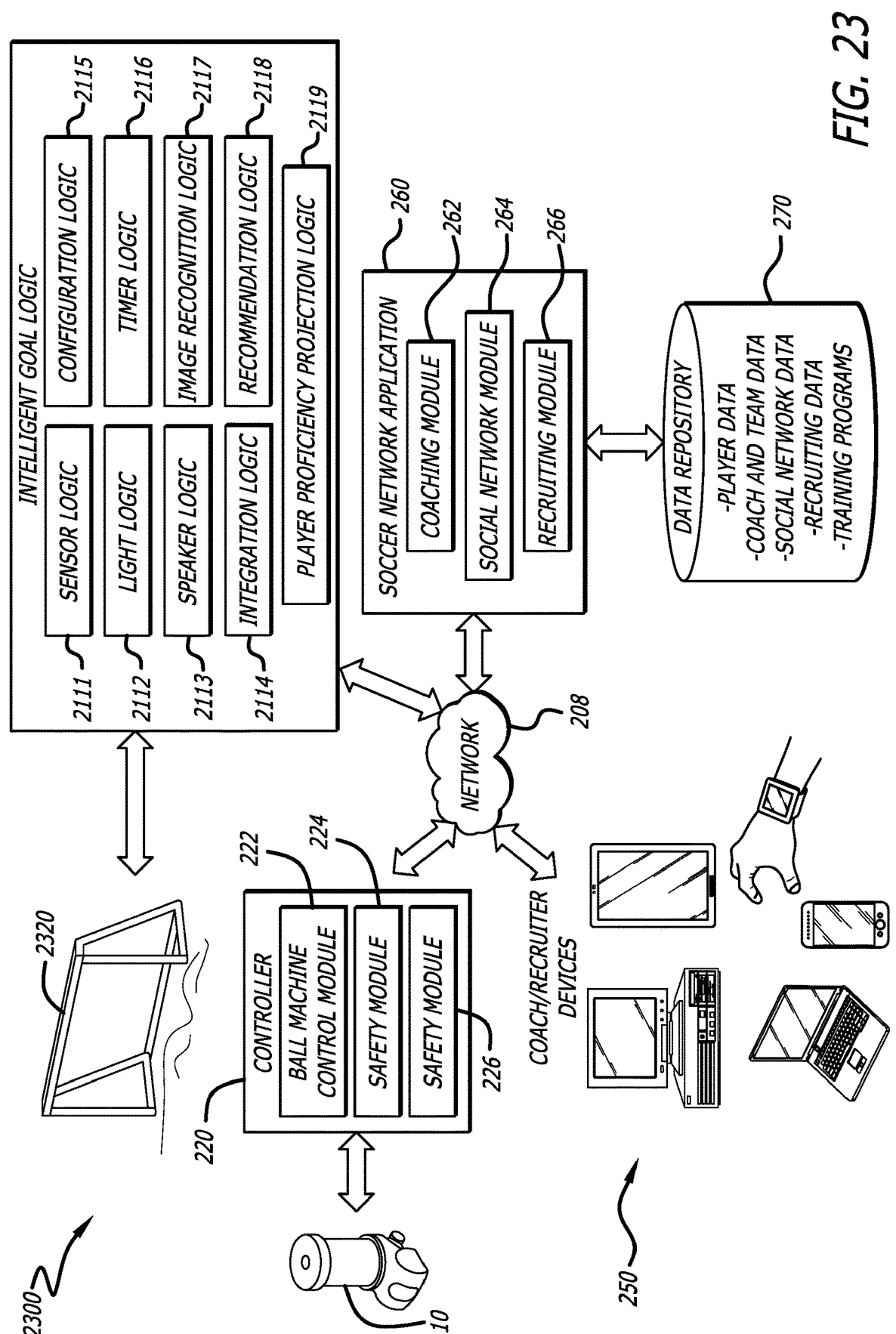
FIG. 23 is an exemplary embodiment of a computing environment for facilitating communications between the controller and a soccer network application of FIG. 7, the intelligent goal logic and an intelligent goal.

In addition, a goal may be communicatively coupled to a coach's device (e.g., s, smart phone, smart watch, iPod®, iTouch®, or any electronic device with wireless/Bluetooth® connectivity) and a ball-throwing machine. Referring to FIG. 23, an exemplary embodiment of a computing environment 2300 for facilitating communications between the controller and a soccer network application of FIG. 7, the intelligent goal logic and an intelligent goal is shown. As illustrated, a training session may include the use of one or more intelligent goals ("the intelligent goal") 2320, a coach's device 250 and a ball-throwing machine 10. Additionally, a soccer network application 260 may also be included.

In one embodiment, the coach's device 250 may be a wearable, just as a smart watch, which includes Bluetooth® connectivity capabilities (or other wireless connectivity capabilities) and software functionality enabling communication with and control of one or more of the intelligent goal 2320 and/or the ball-throwing machine 10. Upon connecting via Bluetooth® to one or more of the intelligent goal 2320 and/or the ball-throwing machine 10, the wearable may control functionality of the intelligent goal 2320 and/or the ball-throwing machine 10 related to, inter alia, the sensor logic, the light logic, the speaker logic, the integration logic, the configuration logic, the timer logic, the imagine recognition logic, the recommendation logic and/or the player proficiency logic.

In addition, the user may wear a similar wearable device which includes Bluetooth® connectivity capabilities (or other wireless connectivity capabilities) and software functionality enabling communication with and control of one or more of the intelligent goal 2320 and/or the ball-throwing machine 10. Such a wearable device worn by the user may monitor and record health-related statistics of the user (e.g., heart rate, steps, calories burned, etc.) so that the health-related statistics of the user may be correlated with the statistics of the drills/sessions completed by the user. For example, the correlation may illustrate a particular drill elevates the heart rate of a particular user more than other drills, allowing a trainer to see the conditioning of the particular user associated with the particular drill should be improved. Additionally, the correlation may influence drill and/or session recommendations, as will be discussed below. As used herein, a session refers to one or more drills.

With respect to the intelligent goal 2320, as discussed above, the processor and/or memory, e.g., storing the intelligent goal logic, may be included in the ball throwing machine, the intelligent goal 2320 and/or the coach's device. The input from the sensors of the intelligent goal 2320 may be combined with input and/or feedback from the ball throwing machine 10 (e.g., the number of soccer balls that have been provided to a user, the speed(s), the angle(s), the direction(s), etc.) such that the plurality of lights integrated with or attached to the intelligent goal 2320 may be turned on and/or turned off according to the input from the intelligent goal 2320 and/or the ball throwing machine 10. Additionally, the input and/or feedback received from the sensors of the intelligent goal 2320 may be stored in a data repository 270 according to a player profile or the like. The ball throwing machine 10 and the coach's device 250 may include the functionality as discussed above. Additionally, instructions comprising a training program, as discussed above, may include instructions corresponding to functionality of the intelligent goal 2320 as discussed herein. For example, instructions comprising the training program may include instructions corresponding to the ball throwing machine 10 and instructions corresponding to one or more logic components of the intelligent goal logic. In addition, instructions comprising the training program may also be directed to two or more intelligent goals such that a training program utilizes a ball-throwing machine and two or more intelligent goals.

1. Player Profile

Discussed above with respect to FIG. 7, the data repository 270 may store player data. More particularly, the data repository 270 may be, at least in part, cloud storage and store player data in the form of a player profile. A player profile may be created for each person (e.g., a user) that utilizes the ball-throwing machine, coach's device and/or intelligent goal system (cumulatively referred to as "the system"). A player profile may include, but is not limited or restricted to, one or more of: identifying information, statistics based on experience using the system which may be measured in points (e.g., indicating repetitions, time, accuracy, etc.), "badges" (e.g., awards based on predetermined criteria), a "player level" (e.g., score-numerical, title, etc.—based on one or more of experience, age, gender, position, session/drill history, affiliate studio, etc.), affiliate studio location, etc. A player profile may be used by a studio (e.g., trainers at a specific location) and/or a mobile application/ website to track the session/drill history and progress of a user. In particular, a player profile may include a player level that includes a numerical score or title signifying a culmination of the user's history of using the system, which may account for repetitions using the system, repetitions of particular drills, accuracy while completing particular drills, badges earned, etc. As the player continues to use the system the player level will adjust accordingly (e.g., typically increase as the user continues to complete more drills and improve his/her accuracy). For example, a user's player level may increase (e.g., increase numerically or progress along a series of titles) once a predetermined number of drills have been completed, once the player's accuracy at a particular drill exceeds a threshold, a combination thereof, etc. A badge may be earned based on predetermined criteria and also result in, or contribute to, an increase in the player level. The predetermined criteria may include, but is not limited to, utilization of the system for a predetermined number of days in a row or percentage of days (e.g., in a week, month, etc.), a predetermined accuracy level on one or more drills, a predetermined number of repetitions (e.g., overall, a particular drill, etc.). In some embodiments, an earned badge or certain player level may enable the user to try new drills. Additionally, as a player level increases or badges are earned, accuracy or timing in certain drills may need to improve to earn an additional badge or advance to the next player level. The player level may be, at least in part, determined by the experience points earned during each drill. For example, a user may earn experience points by completing a drill with a predetermined accuracy (e.g., a first amount of experience points for completing within a first accuracy threshold, and a second amount for completing within a second accuracy threshold, the second amount being greater than the first amount when the second accuracy threshold is higher than the first accuracy threshold). Timing thresholds may be used in a similar manner as accuracy thresholds to determine the amount of experience points earned by a user. Additionally, a training drill may provide a user with a predetermined number of balls and award extra experience points based on certain balls scored (e.g., 10 balls where extra experience points are awarded when any of the last 3 balls provided are scored accuratelymeaning within the required zone, if applicable). Alternatively, or in addition, extra experience points may be awarded when goals are scored accurately within a predetermined time of a drill (e.g., a first portion, a middle portion, or an end portion-thereby emphasizing certain scenarios within a game) and/or a predefined number of balls are scored accurately in a row or within a predefined time period.

The player level may be displayed on display screens (e.g., scoreboards) at a studio, accessed via a website and/or via a mobile application allowing a user to track his/her drill/session history, abilities (e.g., accuracy, timing, etc.) over time and badges earned. Additionally, upon completing a drill and/or a session, a player's statistics may be compiled, cumulatively or for the particular drill/session, so that the user may visually review the statistics and progress made, including experience points earned, whether a new player level was achieved and/or a new badge earned. Additionally, such statistics may be displayed during each drill so the user may have knowledge of such progress while attempting to complete the drill (e.g., to provide motivation to the user to continue trying as hard as possible).

The player profile may also include an avatar that may be customizable by the user. The user may "unlock" new avatars, or avatar features (skills, appearances, clothing, etc.) upon earning certain badges or advancing to certain player levels. The player profile is not tied to a particular studio but may be accessed by the user (or a trainer) at any studio (e.g., the user may visit multiple studios and want to keep track of drill/session history, accuracy, timing statistics, etc., while at each studio).

As discussed briefly above, the player profile may be linked to a scouting tool (e.g., website or alternative software, possibly of a third-party). In such an embodiment, the user (or parents) may opt in to linking the player profile to the scouting tool. By linking the player profile to the scouting tool, coaches (e.g., high school, club, college, etc.) may be able to assess a player's skill level quickly based on the player score and badges earned and have a standard format by which to compare multiple players (e.g., in assessing invitations to join a team, offer letters, scholarships, etc.). Additionally, as a player profile may include age, gender, and position, coaches may easily sort through players when looking to assess players of a particular age (or range), gender and/or position.

a. Drill and Session Recommendations

In addition to maintaining a player profile so that, inter alia, a user may review his/her metrics and drill/session history, the system may include logic, recommendation logic 2118, that recommends a drill or session for a user based, at least in part, on the player profile (e.g., experience points, player level, history of drills completed, etc.). In one embodiment, the recommendation logic 2118 may utilize a set of predetermined rules to generate a session of recommended drills (or alternatively, a single drill). For example, the recommendation logic 2118 may analyze—e.g., parse-a user's player profile and based on the information associated with the player's profile, recommend a session or individual drill for the user. The recommendation logic 2118 may use one or more of the following to recommend a session or drill according to a predetermined rule set: age, gender, position, player level, experience points, badges, session/drill history, accuracy in one or more drills, studio, timing until completion for one or more drills, etc. The recommendation logic 2118 may be stored in non-transitory computer-readable medium located in the coach's device (e.g., a mobile application) wherein the processing is performed by one or more processors of the coach's device and/or in cloud-storage wherein the processing is performed by one or more processors of one or more servers associated with the cloud storage.

Once the session or drill recommendation has been provided to the user and/or trainer, the trainer may initiate the session or drill via the coach's device. Alternatively, the trainer may adjust the recommendation to focus the drill or session on a particular aspect (e.g., headers, low shots, high shots, trapping a ball provided to the user in the air prior to shooting at the intelligent goal, etc.) In one embodiment, the recommendation logic 2118 may generate a GUI displaying the recommendation and enabling the trainer to adjust—customize—the recommendation via user input that provides the recommendation logic 2118 with information as to a preferred aspect. The recommendation logic 2118 may then adjust the recommendation according to a predetermined rule set that accounts for the player profile and the preferred aspect.

In yet another embodiment, a drill may be adjusted during the drill, prior to completion. For example, a user wearing a smart wearable that is connected wirelessly to the coach's device, the intelligent goal and/or the ball-throwing machine, may provide instructions to the ball-throwing machine and/or the intelligent goal, possibly via the coach's device, to adjust the drill. The user may increase/decrease the speed at which the ball-throwing machine provides the user with balls and/or the time duration of each interval in between balls. Additionally, a trainer may provide such instructions via the coach's device. This may be advantageous when the user is, for example, tired and needs a longer time interval between balls, or alternatively, is excelling and needs to be challenged with shorter intervals between balls. It has been contemplated that the experience points awarded to a user may be adjusted according to adjustments made during the drill (e.g., increase the amount of experience points when a user increases the speed at which the ball-throwing machine provides each ball).

b. Player Proficiency Projection

Furthermore, the system may include logic, player proficiency projection logic 2119 as seen in FIG. 21, that analyzes the information associated with the player profile to project the player's abilities (e.g., proficiency) in the future. The analysis performed by the player proficiency projection logic 2119 may include a rules-based analysis that enables the player proficiency projection logic 2119 to use stored information (e.g., statistics based on experience using the system which may be measured in points (e.g., repetitions, time, accuracy, etc.), earned badges, a player level, etc.) and correlate the stored information with for example, gender, age, height, weight, position, etc. to project, according to one or more predetermined rules, future abilities of the player. Additionally, the affiliate studio location may be used in the correlation as a pattern may develop such that players at a particular affiliate studio may develop more rapidly and to a higher degree than players at other affiliate studios. The rules-based analysis may project player proficiency in terms of a player level, accuracy statistics, earned badges, etc., to enable comparisons with other players' proficiency projections. Additionally, the player proficiency projection logic 2119 may provide projections such as projected top ball speed on shots, projected accuracy statistics (shots on goal, shots scored, accurate goals scored, time to complete one or more drills, etc.), thereby allowing a coach or scout to consider such projections when determining whether to provide the player with a roster position and/or a scholarship. As one example, the player proficiency projection logic

2119 may analyze information stored over time in a user's player profile at multiple ages (e.g., top shot speed measured at ages 9, 10 and 11 to project top shot speed at age 16, 18 and 20 based on one or more statistics within the player profile used in the rule-based analysis). The player proficiency projection logic 2119 may project any of the statistics stored in the player profile for any future age of a user when the user's player profile has stored the information necessary to perform the analysis. As an alternative to the rules-based analysis, or in addition to, the player proficiency projection logic 2119 may include a machine learning logic component that adapts its analysis based on actual, measured data. For example, the player proficiency projection logic 2119 may use machine learning logic to project a user's player proficiency and based on actual, measured statistics of the user at a future age, the machine learning logic may adjust its analysis. As one example, the player proficiency projection logic 2119 may perform an analysis for one or more users in the system while the one or more users are at a first age (e.g., age 9) and project the top shot speed of the one or more users future ages (e.g., 10, 11, 12, etc.). Upon measuring the actual top shot speed of the one or more users at the future ages, the machine learning logic component of the player proficiency projection logic 2119 may adjust its analysis to more accurately project users' statistics based on the projected statistic compared to the actual, measured statistic.

2. Diagnostics

An additional advantage to maintaining a record of all drills performed is that statistics for each ball-throwing machine and intelligent goal are known. For example, the total number of balls provided to users each machine is known. Therefore, a trainer or maintenance staff employee may diagnose the status of each ball-throwing machine. In particular, a trainer or maintenance staff employee may track the total number of balls provided by each ball-throwing machine and perform pre-emptive maintenance (e.g., replace a component within the machine, oil the machine, etc.) when predefined thresholds are met—e.g., predefined numbers of total balls provided by a machine. Similarly, a trainer or maintenance staff employee may diagnose each intelligent goal to determine the number of balls shot at the intelligent goal. Based on experiential knowledge, predefined thresholds of balls shot at an intelligent goal may be set such that, upon exceeding such predefined thresholds, a trainer or maintenance staff employee is to perform manual diagnostics on the intelligent goal including, for example, visually checking each sensor is not broken, the net is intact, etc. In some embodiments, the logic of the system may provide an alert to a trainer and/or maintenance staff employee that the thresholds discussed herein have been exceeded. The statistics used to determine whether the thresholds have been exceeded may be stored in cloud storage (e.g., the data repository 270 of FIGS. 7 and 23) along with a corresponding machine identifier for retrieval by any coach's device or via a website.

3. Trainer Evaluation and Location Data Tracking

Upon completing a session, a user may rate and/or comment on the trainer that was facilitating the session. For example, a user may rate a trainer according to a predetermined, set rating scale (e.g., one through five stars).

The coach's device may also track each drill that was initiated by each trainer via the coach's device. The trainer may be asked to log-in to access the coach's device application, which enables the trainer to initiate a session/drill. Therefore, each drill initiated by each trainer may be recorded (e.g., in the data repository 270). The metrics of each trainer (e.g., time spent at a studio, drills initiated, efficiency (a number of drills initiated according to time spent at the studios), retention rate of the trainer by a user, etc.) may be recorded and used, at least in part, in mid-year or end-year evaluations of each trainer. Additionally, improvements of users under each trainer may be compared across trainers by utilizing the player profiles of users under a trainer (e.g., to determine average change in player level, experience points, etc., of users under each trainer). The metrics of each trainer may enable a comparison of trainers at each studio. The comparisons may be displayed in a graphical format (e.g., via a graphical user interface (GUI)—in one embodiment, referred to as a "reporting dashboard") accessible by a mobile application and/or a website.

4. Mobile Application and Website

As mentioned above, the user's player profile may be viewable in a mobile application and/or website (for convenience, collectively referred to herein as "the mobile application") via an electronic device. The user may open the mobile application to view the user's player profile. In addition to reviewing player metrics, drill/session history, badges earned, player level, etc., the mobile application may be opened before or during a drill and provide audio via one or more speakers included in or coupled to the electronic device. The audio may include, but is not limited or restricted to, music, audio instructions associated with a drill (current drill or next drill), and/or feedback/motivation. In one embodiment, the mobile application may include logic that is configured to stream music via the internet, play music stored on non-transitory computer-readable medium of the electronic device and/or play music via a radio station.

The logic of the mobile application may additionally be configured to provide audible instructions associated with the drill being performed by the user. For example, the logic of the mobile application may provide instructions such as, inter alia, turn, trap, one touch, perform a particular move prior to shooting, etc. The audible instructions may enable a user to receive customized training instructions (e.g., the audible instructions may be provided according to a user's experience points, player level, badges, etc. so that users at various player levels may receive audible instructions corresponding to the user's player level, points, etc.). The audible instructions may allow a user to receive customized instructions while all other trainers are preoccupied (e.g., a session using audible instructions may cost less than a session involving a trainer). In addition, when a user wears a smart wearable that is wirelessly connected to the mobile application via the electronic device, the mobile application may receive health information of the user (heart rate, calories burned, steps, etc.) and provide audible instructions to take a break, get a drink, eat a small snack, etc. The mobile application may also provide audible instructions during the drill according to health information received from a smart wearable (e.g., audible instructions instructing a user to run a little faster in order to get heart rate to a target heart rate). The mobile application may also provide audible instructions regarding timing (e.g., countdown to end of drill or countdown to end of break between drills, etc.)

The mobile application may also include a "content feed" section that may provide the user with videos, articles, tips, etc. (the content feed may be targeted according to the player profile—e.g., age, gender, position, skill level, etc.). In one embodiment, the content feed section may be updated according to drills completed or drills to be completed (e.g., advice on trapping balls when drills to be completed include one or more drills associated with trapping balls). The drills to be completed may be determined via a predetermined rule set (and/or in conjunction with the recommendations as discussed above, wherein the recommendations for future training sessions/drills are determined following a completed drill/session).

Additionally, the mobile application may include a booking/reservation system section. For example, a calendar may be displayed allowing a user (or parent) to schedule a training session time via input to the mobile application. Bookings may also be suggested based on previous bookings or other factors such as bookings of other users of a similar age, gender, player level, preferred trainer, etc.

In yet another embodiment, the mobile application may be configured to generate custom drills according to received user input of particular aspects of a drill. In such an embodiment, the mobile application receives user input corresponding to one or more aspects of a drill, wherein an aspect of a drill may be an instruction to a ball-throwing machine or an intelligent goal. The instruction may correspond to, inter alia, a time period for the custom drill, a zone establishment pattern (e.g., when zones are established-based on one or more timers and/or goals scored), a number of balls to provide to the user, characteristics of providing a ball to a user (angle, speed, direction, etc.), characteristics of one or more lights of one or more goals (e.g., color characteristics, timing of turning on or turning off one or more lights-based on one or more timers and/or goals scored), a pattern for scoring an "accurate goal," as discussed above, etc.

Although the examples and figures discussed above focus on the use of an intelligent goal, an "intelligent hurdle" and/or "intelligent cone" may be used in a similar manner and include similar logic. For example, an intelligent hurdle or intelligent cone may include wireless connectivity capabilities and be configured to connect to a coach's device in order to receive information associated with one or more training drills. The intelligent hurdle or intelligent cone may include one more sensors and/or one or more lights as discussed above with respect to the intelligent goal. Additionally, it has been contemplated that training drills may also include scenarios in which the user triggers an interrupt of a sensor beam with his/her hand or foot, in contrast to a ball. Such a drill may be designed to work on the players quickness (e.g., back and forth between two or more intelligent goals, hurdles and/or cones) or exercises such as checking back to the ball or bringing a defender away and sprinting toward the ball.

VIII. Terminology

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together. Although certain computer-implemented tasks are described as being performed by a particular entity, other embodiments are possible in which these tasks are performed by a different entity.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CDROM, or any other form of non-transitory computer-readable storage medium, media, or physical computer storage known in the art. An exemplary storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A computerized method comprising:
detecting a through-beam between a first sensor and a second sensor of a first sensor pair, the first sensor being located at a first goal post of a goal apparatus, the second sensor being located at a second goal post of the goal apparatus, wherein the first goal post and the second goal post form a goal plane;
detecting an interrupt in the through-beam between the first sensor and the second sensor; and
responsive to detecting the interrupt:
determining an object has passed through the goal plane,
determining a speed of the object as the object passed through the goal plane by determining a time duration of the interrupt in the through-beam and correlating the time duration of the interrupt with a known size of the object.

2. The computerized method of claim 1, further comprising:
recording an indication of the object passing through the goal plane and the speed of the speed of the object as the objected passed through the goal plane in a player profile.

3. The computerized method of claim 1, further comprising:
determining a trajectory of the object as the object passes through the goal plane based on timings of interrupts detected at a plurality of sensor pairs of the goal apparatus.

4. The computerized method of claim 1, further comprising:
determining a zone of the goal plane through which the object passed based on a position of the first sensor along the first goal post.

5. The computerized method of claim 1, further comprising:
responsive to determining the object has passed through the goal plane, altering a state of a light of the goal apparatus from a first state to a second state.

6. The computerized method of claim 1, further comprising:
obtaining user input corresponding to a selected training drill.

7. A goal apparatus comprising:
a first goal post having a first sensor located thereon;
a second goal post having a second sensor located thereon, wherein the first sensor and second sensor form a first sensor pair, and wherein the first goal post and the second goal post form a goal plane; and
a housing having one or more processors stored therein; and a storage device stored in the housing and communicatively coupled to the one or more processors, the storage device having stored thereon logic that, when executed by the one or more processors causes operations to be performed including:

detecting a through-beam between the first sensor and the second sensor, detecting an interrupt in the through-beam between the first and second sensors, and responsive to detecting the interrupt:

determining an object has passed through the goal plane, and determining a speed of the object as the object passed through the goal plane by determining a time duration of the interrupt in the through-beam and correlating the time duration of the interrupt with a known size of the object.

8. The goal apparatus of claim 7, wherein the operations to be performed further include:

recording an indication of the object passing through the goal plane and the speed of the speed of the object as the objected passed through the goal plane in a player profile.

9. The goal apparatus of claim 7, wherein the operations to be performed further include:

determining a trajectory of the object as the object passes through the goal plane based on timings of interrupts detected at a plurality of sensor pairs of the goal apparatus.

10. The goal apparatus of claim 7, wherein the operations to be performed further include:

determining a zone of the goal plane through which the object passed based on a position of the first sensor along the first goal post.

11. The goal apparatus of claim 7, wherein the operations to be performed further include:

responsive to determining the object has passed through the goal plane, altering a state of a light of the goal apparatus from a first state to a second state.

12. The goal apparatus of claim 7, wherein the operations to be performed further include:

obtaining user input corresponding to a selected training drill.

13. A non-transitory computer-readable medium having stored thereon logic, the logic being executable by one or more processors to perform operations including:

detecting a through-beam between a first sensor and a second sensor of a first sensor pair, the first sensor being located at a first goal post of a goal apparatus, the second sensor being located at a second goal post of the goal apparatus, wherein the first goal post and the second goal post form a goal plane;

detecting an interrupt in the through-beam between the first sensor and the second sensor; and responsive to detecting the interrupt:

determining an object has passed through the goal plane, and determining a speed of the object as the object passed through the goal plane by determining a time duration of the interrupt in the through-beam and correlating the time duration of the interrupt with a known size of the object.

14. The non-transitory computer-readable medium of claim 13, wherein the operations further include:

recording an indication of the object passing through the goal plane and the speed of the speed of the object as the objected passed through the goal plane in a player profile.

15. The non-transitory computer-readable medium of claim 13, wherein the operations further include:

determining a trajectory of the object as the object passes through the goal plane based on timings of interrupts detected at a plurality of sensor pairs of the goal apparatus.

16. The non-transitory computer-readable medium of claim 13, wherein the operations further include:

determining a zone of the goal plane through which the object passed based on a position of the first sensor along the first goal post.

17. The non-transitory computer-readable medium of claim 13, wherein the operations further include:

obtaining user input corresponding to a selected training drill.

* * * * *